US006270973B1

(12) United States Patent
Lewis et al.

(10) Patent No.: US 6,270,973 B1
(45) Date of Patent: *Aug. 7, 2001

(54) MULTIPLEX METHOD FOR NUCLEIC ACID DETECTION

(75) Inventors: Martin K. Lewis, Madison; Daniel Kephart, Cottage Grove; Richard Byron Rhodes, Madison; John William Shultz, Verona; Donna Leippe, Middleton; Michelle Mandrekar, Oregon; Christine Ann Andrews, Cottage Grove; James Robert Hartnett, Madison; Trent Gu, Madison; Keith V. Wood, Madison, all of WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,064

(22) Filed: Sep. 27, 1999

Related U.S. Application Data

(63) Continuation-in-part of application No. 09/358,972, filed on Jul. 21, 1999, which is a continuation-in-part of application No. 09/252,436, filed on Feb. 18, 1999, which is a continuation-in-part of application No. 09/042,287, filed on Mar. 13, 1998.

(51) Int. Cl.[7] .............................. C12Q 1/68; C12P 19/34; G01N 24/00; C07H 19/04
(52) U.S. Cl. ................................ 435/6; 435/7; 435/91.2; 435/91.5; 436/173; 436/501; 536/26; 536/27; 536/28; 935/77; 935/82
(58) Field of Search ........................ 435/6, 91.2, 91.5, 435/7; 436/173, 501; 536/26, 27, 28; 935/77, 82

(56) References Cited

U.S. PATENT DOCUMENTS

| | | |
|---|---|---|
| 4,303,752 | 12/1981 | Kolehmainen et al. ............... 435/8 |
| 4,331,762 | 5/1982 | Nakajima et al. .................. 435/190 |
| 4,338,395 | 7/1982 | Leon et al. ........................ 435/17 |
| 4,352,881 | 10/1982 | Inagawa et al. .................... 435/17 |
| 4,357,420 | 11/1982 | Bostick et al. ...................... 435/8 |
| 4,368,261 | 1/1983 | Klose et al. ....................... 435/15 |
| 4,371,611 | 2/1983 | Fusee ............................... 435/14 |
| 4,394,445 | 7/1983 | Nix et al. .......................... 435/19 |
| 4,415,655 | 11/1983 | De Castro et al. .................. 435/17 |
| 4,438,124 | 3/1984 | Melster et al. .................... 424/270 |
| 4,443,594 | 4/1984 | Buckmann ......................... 536/27 |
| 4,446,231 | 5/1984 | Self ................................... 435/7 |
| 4,460,684 | 7/1984 | Bauer ............................... 435/14 |
| 4,485,177 | 11/1984 | Siedel et al. ..................... 436/547 |
| 4,595,655 | 6/1986 | Self ................................... 435/7 |
| 4,683,195 | 7/1987 | Mullis et al. ....................... 435/6 |
| 4,683,202 | 7/1987 | Mullis et al. ...................... 435/91 |
| 4,735,897 | * 4/1988 | Vary et al. .......................... 435/6 |

(List continued on next page.)

FOREIGN PATENT DOCUMENTS

| | | | |
|---|---|---|---|
| 0 229 601 | 11/1986 | (EP) . | |
| 639 647 | 7/1994 | (EP) . | |
| 0 663 447 | 12/1994 | (EP) . | |
| 0 894 867 | 11/1997 | (EP) . | |
| 2055200 | 12/1981 | (GB) | ............... G01N/21/76 |
| WO 90/05530 | 5/1990 | (WO) . | |
| WO 91/17264 | 11/1991 | (WO) . | |
| WO 92/13963 | 8/1992 | (WO) . | |
| WO 94/25619 | 11/1994 | (WO) | ............... C12Q/1/00 |
| WO 95/21938 | 8/1995 | (WO) . | |
| WO 96/41014 | 12/1996 | (WO) . | |
| WO 97/41256 | 11/1997 | (WO) . | |
| WO 98/13523 | 4/1998 | (WO) | ............... C12Q/1/68 |
| WO 98/54362 | 4/1998 | (WO) . | |
| WO 98/28440 | 7/1998 | (WO) | ............... C12Q/1/68 |

OTHER PUBLICATIONS

A.E. Sippel, "Purification and Characterization of Adenosine Triphosphate: Ribonucleic Acid Adenyltransferase from *Escherichia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry,* 35:16610–16620 (1996).

(List continued on next page.)

*Primary Examiner*—Jeffrey Fredman
*Assistant Examiner*—Arun Kr. Chakrabarti
(74) *Attorney, Agent, or Firm*—Welsh & Katz, Ltd.

(57) ABSTRACT

Processes are disclosed using the depolymerization of a nucleic acid hybrid to qualitatively and quantitatively analyze for the presence of predetermined nucleic acid target sequences using a multiplex assay format. Applications of those processes include the detection of single nucleotide polymorphisms, identification of single base changes, speciation, genotyping, medical marker diagnostics, and the like.

74 Claims, 2 Drawing Sheets

U.S. PATENT DOCUMENTS

| | | |
|---|---|---|
| 4,743,561 | 5/1988 | Shaffar .................................. 436/501 |
| 4,755,458 | 7/1988 | Rabbani et al. ......................... 435/5 |
| 4,800,159 | 1/1989 | Mullis et al. ...................... 435/172.3 |
| 5,356,776 | 10/1994 | Kambara et al. ........................ 435/6 |
| 5,389,512 | 2/1995 | Sninsky et al. .......................... 435/5 |
| 5,391,480 | 2/1995 | Davis et al. ............................. 435/6 |
| 5,399,491 | 3/1995 | Kacian et al. ........................... 435/6 |
| 5,403,711 | 4/1995 | Walder et al. ........................... 435/6 |
| 5,445,933 | 8/1995 | Eadie et al. ............................. 435/6 |
| 5,494,810 | 2/1996 | Barany et al. ..................... 435/91.52 |
| 5,498,523 | 3/1996 | Tabor et al. ............................. 435/6 |
| 5,512,439 | 4/1996 | Hornes et al. ........................... 435/6 |
| 5,516,663 | 5/1996 | Backman et al. .................... 435/91.2 |
| 5,530,192 | 6/1996 | Murase et al. ....................... 800/205 |
| 5,541,311 | 7/1996 | Dahlberg et al. ................... 536/23.7 |
| 5,561,044 | 10/1996 | Walker et al. ........................... 435/6 |
| 5,573,906 | 11/1996 | Bannwarth et al. ..................... 435/6 |
| 5,622,824 | 4/1997 | Koster et al. ............................ 435/6 |
| 5,648,232 | 7/1997 | Squirrell ................................. 435/34 |
| 5,660,988 | 8/1997 | Duck et al. .............................. 435/6 |
| 5,667,964 | 9/1997 | Ho ............................................ 435/5 |
| 5,683,877 | 11/1997 | Lu-Chang et al. ...................... 435/6 |
| 5,691,146 | 11/1997 | Mayrand ................................. 435/6 |
| 5,723,591 | 3/1998 | Livak et al. ........................ 536/22.1 |
| 5,731,146 | 3/1998 | Duck et al. .............................. 435/6 |
| 5,736,365 | 4/1998 | Walker et al. ....................... 435/91.2 |
| 5,741,635 | 4/1998 | Boss et al. ............................... 435/4 |
| 5,759,820 | 6/1998 | Hornes et al. ....................... 435/91.1 |
| 5,763,181 | 6/1998 | Han et al. ................................. 435/6 |
| 5,766,849 | 6/1998 | McDonough et al. .................. 435/6 |
| 5,786,139 | 7/1998 | Burke et al. ............................. 435/6 |
| 5,786,183 | 7/1998 | Ryder et al. ......................... 435/91.2 |
| 5,814,491 | 9/1998 | Vijg et al. ........................... 435/91.2 |
| 5,824,517 | 10/1998 | Cleuziat et al. ..................... 435/91.2 |
| 5,834,202 | 10/1998 | Auerbach ................................. 435/6 |
| 5,840,873 | 11/1998 | Nelson et al. ....................... 536/24.3 |
| 5,843,660 | 12/1998 | Schumm et al. ......................... 435/6 |
| 5,849,547 | 12/1998 | Cleuziat et al. .................... 435/91.21 |
| 5,853,981 | 12/1998 | Kondo et al. ............................ 435/5 |
| 5,854,033 | 12/1998 | Lizardi ................................ 435/91.2 |
| 5,861,242 | 1/1999 | Chee et al. ............................... 435/5 |
| 5,863,736 | 1/1999 | Haaland ................................... 435/6 |
| 5,866,337 | 2/1999 | Schon ....................................... 435/6 |
| 5,869,252 | 2/1999 | Bouma et al. ........................... 435/6 |
| 5,871,902 | 2/1999 | Weininger et al. ...................... 435/5 |
| 5,876,924 | 3/1999 | Zhang et al. ............................. 435/5 |
| 5,876,930 | 2/1999 | Livak et al. ............................. 435/6 |
| 5,876,978 | 3/1999 | Willey et al. ....................... 435/91.2 |
| 5,880,473 | 3/1999 | Ginestet ............................ 250/458.1 |
| 5,882,856 | 3/1999 | Shuber ..................................... 435/6 |
| 5,885,775 | 3/1999 | Haff et al. ................................ 435/6 |
| 5,888,819 | 3/1999 | Goelet et al. ............................ 435/5 |
| 5,902,722 | 5/1999 | Di Cesare et al. ...................... 435/4 |
| 6,007,987 | 12/1999 | Cantor et al. ............................ 435/6 |
| 6,066,483 | 5/2000 | Riggs et al. ........................... 435/194 |

OTHER PUBLICATIONS

S. Karamohamed, M. Ronaghi and P. Nyren, "Bioluminometric Method for Real–Time Detection of Reverse Transcriptase Activity", *Biotechniques*, 24:302–306 (Feb., 1998).

B. Hove–Jensen, K. W. Harlow, C.J. King, R.L. Switzer, "Phosphoribosylpyrophosphate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M. Y. Karpeisky, N.B. Tarusova, R.M. Khomutov, H.B.F. Dixon, "The Mechanism of Pyrophosphorolysis of RNA by RNA Polymerase", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriophage T7 DNA Polymerase", *J. Biol. Chem.*, 264(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation of Total DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem.*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5' exonuclease site of __ 29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin—Madison, http://www.bact.wisc.edu/bact102/102dil3.html undated.

J. Lindquist, Dept. of Bacteriology, University of Wisconsin—Madison, http://www.bact.wisc.edu/bact102/102dil3a.html undated.

Most Probable Number (MPN), WQA Glossary of Terms, 3rd Ed., Water Quality Association undated.

P. Nyren, B. Pettersson, and M. Uhlen. "Solid Phase DNA Minisequencing by an Enzymatic Luminometric Inorganic Pyrophosphate Release," *Anal. Biochem.*, 242:84–89 (1996).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV –C/HGV injection by multiplex PCR in plasma samples of transfused subjects", *J. Virol Meth.*, 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2):237–243.

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., *Anal. Biochem.*, 244:367–373 (1997).

S. Borman, "Developers of Novel DNA Sequencers Claim Major Performance Advances", *C & EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci., USA*, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci., USA*, 88:7276–7280 (1991).

R. Kramer, et al., *Nat. Biotechnol.*, 14:303–308 (1996).

J. Shultz, D. Leippe, K. Lewis and M. Nelson, "Non–radioactive Measurement of DNA Using Coupled Enzymatic Reactions", Presentation Mar. 16–20, 1998 at a Parenteral Drug Association meeting in San Francisco, California.

Seq ID No. 1, "Blast Archaeal Gemone Sequences at Center of Marine Biotechnology" Online, May 21, 1999, Retrieved on Aug. 7, 200 @ http://Combdna.umbi.umd.edu/bags.html.

http://Comb5–156 umbi.umd.edu/cgi–bin/PfurGene.PL?GeneID=894645&Dataset=Nayb&Genei dtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genome of hyper–thermophilic Archaebacterium, *Pyrococcus horikoshii* OT3", *DNA Research*, 5:55–76 (1998).

* cited by examiner

Fig. 1

A    Wild Type Template

3'    CTGAGCAGTACAGAGTCGAAATC 5'    10866(SEQ ID NO:99)
      TCTGACTCGTCATGTCTCAGCTTTAGTTTAATACGACTCACTATAG
      T                                           G
      A                                           G
      GTCTCTTTCTGTTATATCAAG 5'    3' TCCACCTTAGTGTGACTC    10865(SEQ ID NO:82)
5' TTGCAGAGAAAGACAATATAGTTCTTGGAGAAGGTGGAATCACACTGAGTGGA 10870(SEQ ID NO:83)
                        3' CCACTTCCACCTTAGTGTGACTC 5'    10869(SEQ ID NO:85)

B    Mutant Template

3'    CTGAGCAGTACAGAGTCGAAATC 5'    10866(SEQ ID NO:99)
      TCTGACTCGTCATGTCTCAGCTTTAGTTTAATACGACTCACTATAG
      T                                           G
      A                                           G
      GTCTCTTTCTGTTATATCAAG 5'    3' TCCACCTTAGTGTGACTC    10865(SEQ ID NO:82)
5' TTGCAGAGAAAGACAATATAGTTCTTTGAGAAGGTGGAATCACACTGAGTGA 10994(SEQ ID NO:83)
                      3' ACACTTCCACCTTAGTGTGACTC 5'    10989(SEQ ID NO:85)

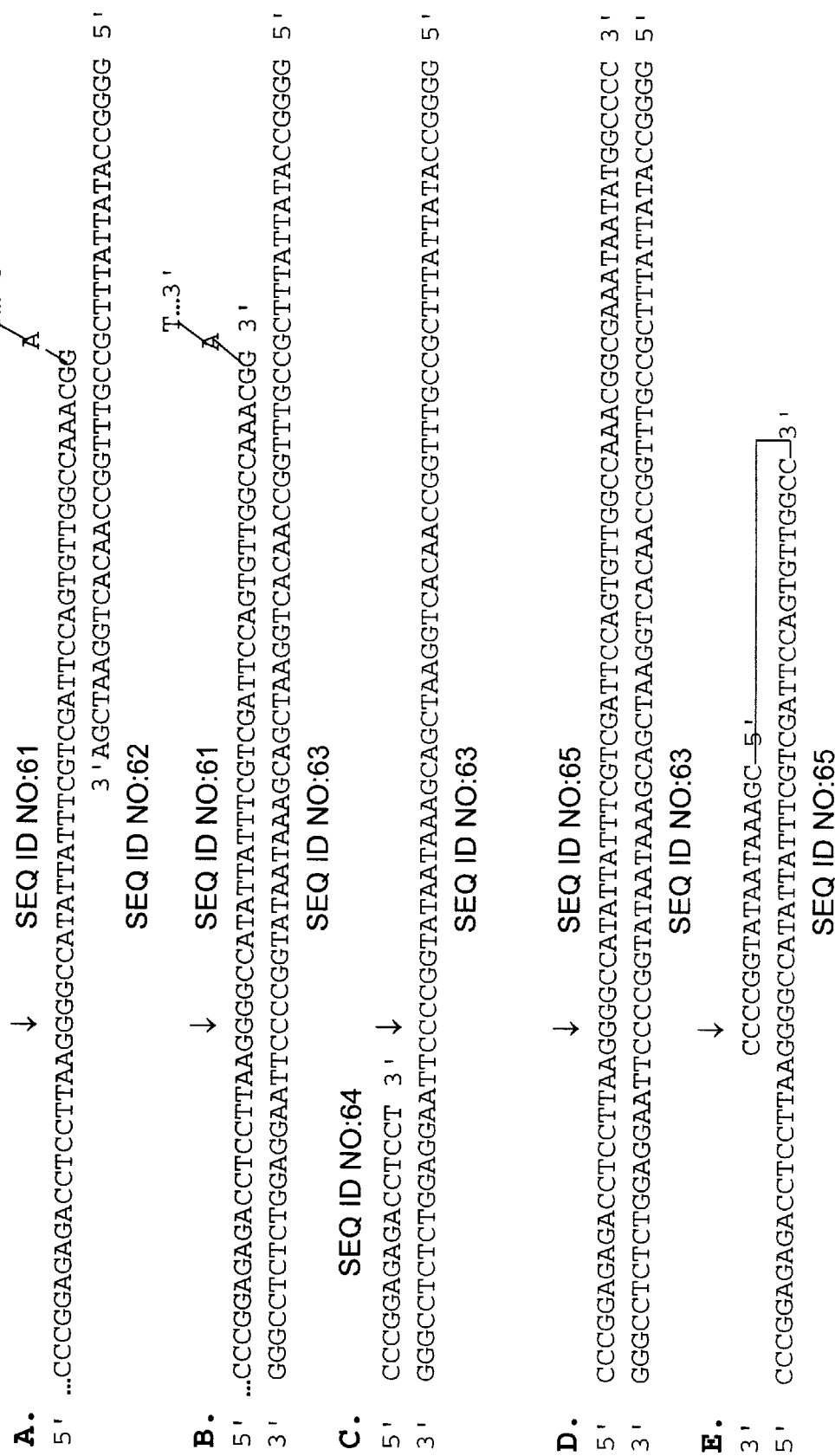

MULTIPLEX METHOD FOR NUCLEIC ACID DETECTION

CROSS-REFERENCE TO RELATED APPLICATION

This application is a continuation-in-part of U.S. Ser. No. 09/358,972, filed on Jul. 21, 1999, which is a continuation-in-part of U.S. Ser. No. 09/252,436, filed on Feb. 18, 1999, which is a continuation-in-part of U.S. Ser. No. 09/042,287, filed Mar. 13, 1998, all of which are incorporated herein by reference.

TECHNICAL FIELD

The invention relates to nucleic acid detection. More specifically, the invention relates to the determination of the presence or absence of multiple targeted, predetermined nucleic acid sequences in nucleic acid target/probe hybrids, and the various applications of their detection.

BACKGROUND OF THE INVENTION

Methods to detect nucleic acids and to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, the need to detect multiple nucleic acids in one sample, or the ability to automate the process.

The detection of nucleic acids or specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as medical diagnostics.

Some general methods to detect nucleic acids are not dependent upon a priori knowledge of the nucleic acid sequence. A nucleic acid detection method that is not sequence specific, but is RNA specific is described in U.S. Pat. No. 4,735,897, where RNA is depolymerized using a polynucleotide phosphorylase (PNP) in the presence of phosphate or using a ribonuclease. PNP stops depolymerizing at or near a double-stranded RNA segment. Sometimes double-stranded RNA can occur as a type of secondary structure RNA, as is common in ribosomal RNA, transfer RNA, viral RNA, and the message portion of mRNA. PNP depolymerization of the polyadenylated tail of mRNA in the presence of inorganic phosphate forms ADP. Alternatively, depolymerization using a ribonuclease forms AMP. The formed AMP is converted to ADP with myokinase, and ADP is converted into ATP by pyruvate kinase or creatine phosphokinase. Either the ATP or the byproduct from the organophosphate co-reactant (pyruvate or creatine) is detected as an indirect method of detecting mRNA.

In U.S. Pat. No. 4,735,897, ATP is detected by a luciferase detection system. In the presence of ATP and oxygen, luciferase catalyzes the oxidation of luciferin, producing light that can then be quantified using a luminometer. Additional products of the reaction are AMP, pyrophosphate and oxyluciferin.

Duplex DNA can be detected using intercalating dyes such as ethidium bromide. Such dyes are also used to detect hybrid formation.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Multiplex PCR assays are well known in the art. For example, U.S. Pat. No. 5,582,989 discloses the simultaneous detection of multiple known DNA sequence deletions. The technique disclosed therein uses a first set of probes to hybridize to the targets. Those probes are extended if the targets are present. The extension products are amplified using PCR.

Fluorescence techniques are also known for the detection of nucleic acid hybrids, U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5'→3' direction to release a fluorescent signal from proximity to a fluorescence quencher, for example, TaqMan® (Perkin Elmer; U.S. Pat. No. 5,691,146 and No. 5,876,930).

Enzymes having template-specific polymerase activity for which some 3'→5' depolymerization activity has been reported include *E. coli* DNA Polymerase (Deutscher and Kornberg, *J. Biol. Chem.,* 244(11):3019–28 (1969)), T7 DNA Polymerase (Wong et al., *Biochemistry* 30:526–37 (1991); Tabor and Richardson, *J. Biol. Chem.* 265: 8322–28 (1990)), *E. coli* RNA polymerase (Rozovskaya et al., *Biochem. J.* 224:645–50 (1994)), AMV and RLV reverse transcriptases (Srivastava and Modak, *J. Biol. Chem.* 255: 2000–4 (1980)), and HIV reverse transcriptase (Zinnen et al., *J. Biol. Chem.* 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.,* 15:1182–1192, 1996).

A variety of methodologies currently exist for the detection of single nucleotide polymorphisms (SNPs) that are present in genomic DNA. SNPs are DNA point mutations or insertions/deletions that are present at measurable frequencies in the population. SNPs are the most common variations in the genome. SNPs occur at defined positions within genomes and can be used for gene mapping, defining population structure, and performing functional studies. SNPs are useful as markers because many known genetic diseases are caused by point mutations and insertions/deletions. Some SNPs are useful as markers of other disease genes because they are known to cosegregate.

In rare cases where an SNP alters a fortuitous restriction enzyme recognition sequence, differential sensitivity of the amplified DNA to cleavage can be used for SNP detection. This technique requires that an appropriate restriction enzyme site be present or introduced in the appropriate sequence context for differential recognition by the restriction endonuclease. After amplification, the products are cleaved by the appropriate restriction endonuclease and products are analyzed by gel electrophoresis and subsequent staining. The throughput of analysis by this technique is limited because samples require processing, gel analysis, and significant interpretation of data before SNPs can be accurately determined.

Single strand conformational polymorphism (SSCP) is a second technique that can detect SNPs present in an amplified DNA segment (Hayashi, K. *Genetic Analysis: Techniques and Applications* 9:73–79, 1992). In this method, the double stranded amplified product is denatured and then both strands are allowed to reanneal during electrophoresis in non-denaturing polyacrylamide gels. The separated strands assume a specific folded conformation based on intramolecular base pairing. The electrophoretic properties of each strand are dependent on the folded conformation. The presence of single nucleotide changes in the sequence can cause a detectable change in the conformation and electrophoretic migration of an amplified sample relative to wild type samples, allowing SNPs to be identified. In addition to the limited throughput possible by gel-based techniques, the design and interpretation of SSCP based experiments can be difficult. Multiplex analysis of several samples in the same SSCP reaction is extremely challenging. The sensitivity required in mutation detection and analysis has led most investigators to use radioactively labeled PCR products for this technique.

In the amplification refractory mutation system (ARMS, also known as allele specific PCR or ASPCR), two amplification reactions are used to determine if a SNP is present in a DNA sample (Newton et al. *Nucl Acids Res* 17:2503, 1989; Wu et al. PNAS 86:2757, 1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. This technique requires duplicate amplification reactions to be performed and analyzed by gel electrophoresis to ascertain if a mutated form of a gene is present. In addition, the data must be manually interpreted.

Single base extension (GBA®) is a technique that allows the detection of SNPs by hybridizing a single strand DNA probe to a captured DNA target (Nikiforov, T. et al. *Nucl Acids Res* 22:4167–4175). Once hybridized, the single strand probe is extended by a single base with labeled dideoxynucleotides. The labeled, extended products are then detected using colorimetric or fluorescent methodologies.

A variety of technologies related to real-time (or kinetic) PCR have been adapted to perform SNP detection. Many of these systems are platform based, and require specialized equipment, complicated primer design, and expensive supporting materials for SNP detection. In contrast, the process of this invention has been designed as a modular technology that can use a variety of instruments that are suited to the throughput needs of the end-user. In addition, the coupling of luciferase detection sensitivity with standard oligonucleotide chemistry and well-established enzymology provides a flexible and open system architecture. Alternative analytical detection methods, such as mass spectroscopy, HPLC, and fluorescence detection methods can also be used in the process of this invention, providing additional assay flexibility.

SNP detection using real-time amplification relies on the ability to detect amplified segments of nucleic acid as they are during the amplification reaction. Three basic real-time SNP detection methodologies exist: (i) increased fluorescence of double strand DNA specific dye binding, (ii) decreased quenching of fluorescence during amplification, and (iii) increased fluorescence energy transfer during amplification (Wittwer, C. et al. *Biotechniques* 22:130–138, 1997). All of these techniques are non-gel based and each strategy will be briefly discussed.

A variety of dyes are known to exhibit increased fluorescence in response to binding double stranded DNA. This property is utilized in conjunction with the amplification refractory mutation system described above to detect the presence of SNP. Production of wild type or mutation containing PCR products are continuously monitored by the increased fluorescence of dyes such as ethidium bromide or Syber Green as they bind to the accumulating PCR product. Note that dye binding is not selective for the sequence of the PCR product, and high non-specific background can give rise to false signals with this technique.

A second detection technology for real-time PCR, known generally as exonuclease primers (TaqMan® probes), utilizes the 5' exonuclease activity of thermostable polymerases such as Taq to cleave dual-labeled probes present in the amplification reaction (Wittwer, C. et al. *Biotechniques* 22:130–138, 1997; Holland, P et al *PNAS* 88:7276–7280, 1991). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal.

An additional form of real-time PCR also capitalizes on the intramolecular quenching of a fluorescent molecule by use of a tethered quenching moiety. The molecular beacon technology utilizes hairpin-shaped molecules with an internally-quenched fluorophore whose fluorescence is restored by binding to a DNA target of interest (Kramer, R. et al. *Nat. Biotechnol.* 14:303–308, 1996). Increased binding of the molecular beacon probe to the accumulating PCR product can be used to specifically detect SNPs present in genomic DNA.

A final, general fluorescent detection strategy used for detection of SNP in real time utilizes synthetic DNA segments known as hybridization probes in conjunction with a process known as fluorescence resonance energy transfer (FRET) (Wittwer, C. et al. Biotechniques 22:130–138, 1997; Bernard, P. et al. *Am. J. Pathol.* 153:1055–1061, 1998). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

There is a need for alternative methods for the detection of a plurality of nucleic acid hybrids in a single sample. There is a demand for such methods that are highly sensitive. For example methods to determine viral load of multiple viruses in a single sample that are able to reliably detect as few as 10 copies of a virus present in a body, tissue, fluid, or other biological sample would be in high demand. There is a great demand for methods to determine the presence or absence of nucleic acid sequences that differ slightly from sequences that might otherwise be present. There is a great demand for methods to determine the presence or absence of sequences unique to a particular species in a sample. There is also a great demand for methods that are more highly sensitive than the known methods, quantitative, highly reproducible and automatable.

It would be beneficial if another method were available for detecting the presence of a sought-after, predetermined target nucleotide sequence or allelic or polynucleotide variant. It would also be beneficial if such a method were operable using a sample size of the microgram to picogram scale. It would further be beneficial if the various methods listed above were capable of providing multiple analyses in a single assay (multiplex assays). The disclosure that follows provides one such method.

BRIEF SUMMARY OF THE INVENTION

A method of this invention is used to determine the presence or absence of a plurality of predetermined (known) nucleic acid target sequences in a nucleic acid sample. Such a method utilizes an enzyme that can depolymerize the 3'-terminus of an oligonucleotide probe hybridized to a nucleic acid target sequence to release one or more identifier nucleotides whose presence or absence can then be determined.

One embodiment of the invention contemplates a method for determining the presence or absence of a plurality of predetermined nucleic acid target sequences in a nucleic acid sample. Thus, the presence or absence of at least two predetermined nucleic acid target sequence is sought to be determined. This embodiment comprises the following steps.

A treated sample is provided that may contain a plurality of predetermined nucleic acid target sequences hybridized with their respective nucleic acid probes that include an identifier nucleotide in the 3'-terminal region. The treated sample is admixed with a depolymerizing amount of an enzyme whose activity is to release one or more identifier nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom.

An analytical output is obtained by analyzing for the presence or absence of released identifier nucleotides, preferably such that the probe from which the nucleotide was released is distinguishable. The analytical output indicates the presence or absence of the nucleotide at the predetermined regions of the nucleic acid targets, and, thereby, the presence or absence of the nucleic acid targets.

It is contemplated that an analytical output of the methods of the invention can be obtained in a variety of ways. The analytical output can be ascertained by luminescence. In some preferred embodiments, analysis for released 3'-terminal region identifier nucleotides comprises the detection of ATP, either by a luciferase detection system (luminescence) or an NADH detection system (absorbance spectroscopy). In particularly preferred embodiments, ATP molecules are formed from the nucleotide triphosphates released by the depolymerizing step by a phosphate transferring step, for example using an enzyme such as NDPK (Nucleotide Diphosphate Kinase) in the presence of ADP. In some embodiments the ATP is amplified to form a plurality of ATP molecules. In the ATP detection embodiments, typically the enzyme (NDPK) for converting nucleotides and added ADP into ATP is present in the depolymerization reaction, and thus they are denoted as a "one pot" method.

In an alternative embodiment, the analytical output is obtained by fluorescence spectroscopy. Use of a wide variety of fluorescence detection methods is contemplated. In one exemplary contemplated method, an identifier nucleotide includes a fluorescent label. In a multiplex analysis where it is desirable to distinguish which nucleic acid target sequences are present and which are absent, multiple types of labels can be used. An identifier nucleotide can be fluorescently labeled prior to, or after, release of the identifier nucleotide. It is also contemplated that other than a released identifier nucleotide contains a fluorescent tag. In such an embodiment, the release of nucleotides in a process of the invention is ascertained by a determination of a difference in the length of the polynucleotide probe, for example by capillary electrophoresis imaged by a fluorescent tag at the 5' terminus of the probe or in a region other than the 3' terminal region.

In an alternative embodiment, the analytical output is obtained by mass spectrometry. It is preferred here that an identifier nucleotide be a nucleotide analog or a labeled nucleotide and have a molecular mass that is different from the mass of a usual form of that nucleotide, although a difference in mass is not required. It is also noted that with a fluorescently labeled identifier nucleotide, the analytical output can also be obtained by mass spectrometry. It is also contemplated that the analysis of released nucleotides be conducted by ascertaining the difference in mass of the probe after a depolymerization step of a process of the invention.

In another alternative embodiment, the analytical output is obtained by absorbance spectroscopy. Such analysis monitors the absorbance of light in the ultraviolet and visible regions of the spectrum to determine the presence of absorbing species. In one aspect of such a process, released nucleotides are separated from hybridized nucleic acid and other polynucleotides by chromatography (e.g. HPLC or GC) or electrophoresis (e.g. PAGE or capillary electrophoresis). Either the released identifier nucleotides or the remainder of the probe can be analyzed for to ascertain the release of the identifier nucleotide in a process of the invention. In another aspect of such a process a label may be incorporated in the analyzed nucleic acid.

In another contemplated embodiment, a sample to be assayed is admixed with two or more nucleic acid probes under hybridizing conditions to form a hybridization composition. The 3'-terminal region of a nucleic acid probe hybridizes with partial or total complementarity to the nucleic acid target sequence when that sequence is present in the sample. The 3'-terminal region of the nucleic acid probe includes an identifier nucleotide.

The hybridization composition is maintained under hybridizing conditions for a time period sufficient to form a treated sample that may contain said predetermined nucleic acid target sequence hybridized with a nucleic acid probe. The treated sample is admixed with a depolymerizing amount of an enzyme whose activity is to release one or more nucleotides from the 3'-terminus of a hybridized nucleic acid probe to form a treated reaction mixture. The treated reaction mixture is maintained under depolymerizing conditions for a time period sufficient to permit the enzyme to depolymerize hybridized nucleic acid and release identifier nucleotides therefrom.

The presence of released identifier nucleotides is analyzed to obtain an analytical output, the analytical output indicating the presence or absence of the nucleic acid target sequence. The analytical output may be obtained by various techniques as discussed above.

One method of the invention contemplates interrogating the presence or absence of a specific bases in their nucleic acid target sequences in a sample to be assayed, and comprises the following steps. Here, a hybridization composition is formed by admixing a sample to be assayed with a plurality of nucleic acid probes under hybridizing conditions. The sample to be assayed may contain a nucleic acid target sequence to be interrogated. The nucleic acid target comprises at least one base whose presence or absence is to be identified. The hybridization composition includes a plurality of nucleic acid probes that are each substantially complementary to a nucleic acid target sequence of interest and each probe comprises at least one predetermined nucleotide at an interrogation position, and an identifier nucleotide in the 3'-terminal region.

A treated sample is formed by maintaining the hybridization composition under hybridizing conditions for a time period sufficient for base pairing to occur for all probes when a probe nucleotide at an interrogation position is aligned with a base to be identified in its target sequence. A treated reaction mixture is formed by admixing the treated sample with an enzyme whose activity is to release one or more identifier nucleotides from the 3'-terminus of a hybridized nucleic acid probe to depolymerize the hybrid. The enzymes that can be used in this reaction are further discussed herein. The treated reaction mixture is maintained under depolymerizing conditions for a time period sufficient to permit the enzyme to depolymerize the hybridized nucleic acid and release an identifier nucleotide.

An analytical output is obtained by analyzing for the presence or absence of released identifier nucleotides. The analytical output indicates the presence or absence of the specific base or bases to be identified. The analytical output is obtained by various techniques, as discussed herein. Preferably, an identifier nucleotide is at the interrogation position. In one preferred embodiment, one is able to determine if at least one of the plurality of targets is present in the sample. In an alternative preferred embodiment, one is able to determine which of the plurality of targets are present and which are absent.

A method that identifies the particular base present at an interrogation position, optionally comprises a first probe, a second probe, a third probe, and a fourth probe. An interrogation position of the first probe comprises a nucleic acid residue that is a deoxyadenosine or adenosine residue. An interrogation position of the second probe comprises a nucleic acid residue that is a deoxythymidine or uridine residue. An interrogation position of the third probe comprises a nucleic acid residue that is a deoxyguanosine or guanosine residue. An interrogation position of the fourth nucleic acid probe comprises a nucleic acid residue that is a deoxycytosine or cytosine residue. Preferably, all four probes can be used in a single depolymerization reaction, and their released identifier nucleotides are distinguishable.

In another aspect of the invention, the sample containing a plurality of target nucleic acid sequences is admixed with a plurality of the nucleic acid probes. Several analytical outputs can be obtained from such multiplexed assays. In a first embodiment, the analytical output obtained when at least one nucleic acid probes hybridizes with partial complementarity to one target nucleic acid sequence is greater than the analytical output when all of the nucleic acid probes hybridize with total complementarity to their respective nucleic acid target sequences. In a second embodiment, the analytical output obtained when at least one nucleic acid probe hybridizes with partial complementarity to one target nucleic acid sequence is less than the analytical output when all of the nucleic acid probes hybridize with total complementarity to their respective nucleic acid target sequences. In a third embodiment, the analytical output obtained when at least one nucleic acid probe hybridizes with total complementarity to one nucleic acid target sequence is greater than the analytical output when all of the nucleic acid probes hybridize with partial complementarity to their respective nucleic acid target sequences. In a fourth embodiment, the analytical output obtained when at least one nucleic acid probe hybridizes with total complementarity to one target nucleic acid sequence is less than the analytical output when all of the nucleic acid probes hybridize with partial complementarity to their respective nucleic acid target sequences. The depolymerizing enzymes for use in these four embodiments are as described herein.

Yet another embodiment of the invention contemplates a method for determining the presence or absence of a first nucleic acid target in a nucleic acid sample that may contain that target or may contain a substantially identical second target. For example, the second target may have a single base substitution, deletion or addition relative to the first nucleic acid target. This embodiment comprises the following steps.

A sample to be assayed is admixed with a plurality of nucleic acid probes under hybridizing conditions to form a hybridization composition. The first and second nucleic acid targets each comprise a region of sequence identity except for at least a single nucleotide at a predetermined position that differs between the targets. Each of the nucleic acid probes is substantially complementary to a nucleic acid target region of sequence identity and comprises at least one identifier nucleotide at an interrogation position. An interrogation position of the probe is aligned with the predetermined position of a target when a target and probe are hybridized. Each probe also includes an identifier nucleotide in the 3'-terminal region.

The hybridization composition is maintained under hybridizing conditions for a time period sufficient to form a treated sample wherein the nucleotide at the interrogation position of the probe is aligned with the nucleotide at the predetermined position in the region of identity of the target.

A treated reaction mixture is formed by admixing the treated sample with a depolymerizing amount of an enzyme whose activity is to release one or more nucleotides from the 3'-terminus of a hybridized nucleic acid probe. The reaction mixture is maintained under depolymerization conditions for a time period sufficient to permit the enzyme to depolymerize the hybridized nucleic acid and release the identifier nucleotides.

An analytical output is obtained by analyzing for the presence or absence of identifier nucleotides released from the 3' terminus of the hybridized probe. The analytical output indicates the presence or absence of released identifier nucleotide at the predetermined region, and; thereby, the presence or absence of a corresponding nucleic acid target.

One aspect of the above method is comprised of a first probe and a second probe in the same hybridization composition. The first probe comprises a nucleotide an interrogation position that is complementary to a first nucleic acid target at a predetermined position. The second probe comprises a nucleotide at an interrogation position that is complementary to a second nucleic acid target at a predetermined position.

Another aspect of the above method, the presence or absence of a third nucleic acid target, which is different from the first and second targets, is assayed for in the same sample that may further contain a fourth target that is substantially identical to the third target.

In one aspect of a process of the invention, the depolymerizing enzyme, whose activity is to release nucleotides, is a template-dependent polymerase, whose activity is to depolymerize hybridized nucleic acid, whose 3'-terminal nucleotide is matched, in the 3' to 5' direction in the presence of pyrophosphate ions to release one or more nucleotides. Thus, the enzyme's activity is to depolymerize hybridized nucleic acid to release identifier nucleotides under depolymerizing conditions. Preferably, this enzyme depolymerizes hybridized nucleic acids whose bases in the 3'-terminal region of the probe are matched with total complementarity to the corresponding bases of the nucleic acid target. The enzyme will continue to release properly paired bases from the 3'-terminal region and will stop at or near the location where the enzyme arrives at a base that is mismatched.

In an alternative aspect of the process, the depolymerizing enzyme, whose activity is to release nucleotides, exhibits a 3' to 5' exonuclease activity in which hybridized nucleic acids having one or more mismatched bases at the 3'-terminus of the hybridized probe are depolymerized. Thus, the enzyme's activity is to depolymerize hybridized nucleic acid to release nucleotides under depolymerizing conditions. In this embodiment, the hybrid may be separated from the free probe prior to enzyme treatment. In some embodiments, an excess of target may be used so that the concentration of free probe in the enzyme reaction is extremely low.

In still another alternative aspect of a process of the invention, the depolymerizing enzyme exhibits a 3' to 5' exonuclease activity on a double-stranded DNA substrate having one or more matched bases at the 3' terminus of the hybrid. The enzyme's activity is to depolymerize hybridized nucleic acid to release nucleotides containing a 5' phosphate under depolymerizing conditions.

In a further aspect of the invention, the nucleic acid sample to be assayed is obtained from a biological sample that is a solid or liquid. Exemplary solid biological samples include animal tissues such as those obtained by biopsy or post mortem, and plant tissues such as leaves, roots, stems, fruit and seeds. Exemplary liquid samples include body fluids such as sputum, urine, blood, semen and saliva of an animal, or a fluid such as sap or other liquid obtained when plant tissues are cut or plant cells are lysed or crushed.

In one aspect of the method, the predetermined nucleic acid target sequence is a microbial or viral nucleic acid and nucleic acid probes comprise sequences complementary to those microbial or viral nucleic acid sequences.

In another aspect of the invention, the predetermined nucleic acid target sequence is a gene or region of a gene that is useful for genomic typing. Exemplary target sequences include the Leiden V mutation, a mutant P-globin gene, the cystic fibrosis-related gene in the region of the delta 508 allele, a mutation in a prothrombin gene, congenital adrenal hyperplasia-associated genes, a translocation that takes place in the region of the bcr gene along with involvement of a segment of the abl gene, as well as the loss of heterozygosity of the locus of certain alleles as is found in certain cancers and also allelic trisomy.

Genomic typing can also be used to assay plant genomes such as that of rice, soy or maize, and the genomes of microbes such as *Campylobacter jejuni,* Listeria, *E. coli* OH157, and the genomes of viruses such as cytomegalovirus (CMV) or human immunodeficiency virus (HIV).

A still further embodiment of the invention contemplates a method using thermostable DNA polymerase as a depolymerizing enzyme for determining the presence or absence of a plurality of predetermined nucleic acid target sequences in a nucleic acid sample, and comprises the following steps.

A treated sample is provided that may contain a plurality of predetermined nucleic acid target sequences hybridized to their respective nucleic acid probes whose 3'-terminal regions are complementary to their predetermined nucleic acid target sequences and include an identifier nucleotide in the 3'-terminal region. A treated depolymerization reaction mixture is formed by admixing a treated sample with a depolymerizing amount of a enzyme whose activity is to release an identifier nucleotide from the 3'-terminus of a hybridized nucleic acid probe. In a preferred one-pot embodiment, the depolymerizing enzyme is thermostable and more preferably, the treated reaction mixture also contains (i) adenosine 5' diphosphate, (ii) pyrophosphate, and (iii) a thermostable nucleoside diphosphate kinase (NDPK).

The treated sample is maintained under depolymerizing conditions at a temperature of about 4° C. to about 90° C., more preferably at a temperature of about 20° C. to about 90° C., and most preferably at a temperature of about 25° C. to about 80° C., for a time period sufficient to permit the depolymerizing enzyme to depolymerize the hybridized nucleic acid probe and release an identifier nucleotide as a nucleoside triphosphate. In preferred one-pot reactions, the time period is also sufficient to permit NDPK enzyme to transfer a phosphate from the released nucleoside triphosphate to added ADP, thereby forming ATP. The presence or absence of a nucleic acid target sequence is determined from the analytical output obtained using ATP. In a preferred method of the invention, analytical output is obtained by luminescence spectrometry.

In another aspect of the thermostable enzyme one-pot method for determining the presence or absence of a predetermined nucleic acid target sequence in a nucleic acid sample, the treated sample is formed by the following further steps. A hybridization composition is formed by admixing the sample to be assayed with a plurality of nucleic acid probes under hybridizing conditions. The 3'-terminal region of the nucleic acid probe (i) hybridizes with partial or total complementarity to a nucleic acid target sequence when that sequence is present in the sample, and (ii) includes an identifier nucleotide. A treated sample is formed by maintaining the hybridization composition under hybridizing conditions for a time period sufficient for the predetermined nucleic acid target sequence to hybridize with the nucleic acid probe.

Preferably, for the thermostable enzyme method, the depolymerizing enzyme is from a group of thermophilic DNA polymerases comprising Tne triple mutant DNA polymerase, Tne DNA polymerase, Taq DNA polymerase, Ath DNA polymerase, Tvu DNA polymerase, Bst DNA polymerase, and Tth DNA polymerase. In another aspect of the method, the NDPK is that encoded for by the thermophilic bacteria *Pyrococcus furiosis* (Pfu)

A still further embodiment of the invention contemplates determining the presence or absence of a plurality of nucleic acid target sequences in a nucleic acid sample using a plurality of special nucleic acid probes. These special probes hybridize to the target nucleic acid and are then modified to be able to form a hairpin structure. This embodiment comprises the following steps.

A treated sample is provided that contains a nucleic acid sample that may include a plurality of nucleic acid target sequences, each having an interrogation position, and each hybridized with its respective nucleic acid probe. The probes are comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, and preferably about zero to about 20 nucleotides in length and comprising a sequence that does not hybridize with either the first or second section, is located between the first and second sections of the probe.

The hybridized probes of the treated sample are extended in a template-dependent manner, as by admixture with dNTPs and a template-dependent polymerase, at least through the interrogation position, thereby forming an extended probe/target hybrid. In a preferred embodiment, the length of the probe extension is limited by omission from the extension reaction of a dNTP complementary to a nucleotide of the target sequence that is present upstream of the interrogation position and absent between the nucleotide complementary to the 3'-end of the interrogation position.

The extended probe/target hybrids are separated from any unreacted dNTPs. The extended probe/target hybrid is denatured to separate the strands. The extended probe strands are permitted to form hairpin structures.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequences. In a preferred embodiment, the analytical output for the various targets are distinguishable.

A still further embodiment of the invention, termed REAPER™, also utilizes hairpin structures. This method contemplates determining the presence or absence of a plurality of nucleic acid target sequences, or a specific base within a target sequence, in a nucleic acid sample, and comprises the following steps. A treated sample is provided that contains a nucleic acid sample that may include a plurality of nucleic acid target sequences hybridized with their respective first nucleic acid probe strands.

The hybrid is termed the first hybrid. The first probes are comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of the first probe contains about 5 to about 30 nucleotides that are a repeat of the target sequence from the interrogation position to about 10 to about 30 nucleotides downstream of the interrogation position, and does not hybridize to the first section of the probe. An optional third section of the probe, located between the first and second sections of the probe, is zero to about 50, preferably up to about 20, nucleotides in length and comprises a sequence that does not hybridize to either the first or second section.

The first hybrid in the treated sample is extended at the 3'-end of the first probes, thereby extending the first probes past the interrogation position and forming an extended first hybrid whose sequence includes an interrogation position. The extended first hybrid is comprised of the original target nucleic acids and extended first probes. The extended first hybrid is then denatured in an aqueous composition to separate the two nucleic acid strands of the hybridized duplexes and form an aqueous solution containing separated target nucleic acids and a separated extended first probes.

Second probes that are about 10 to about 2000, preferably about 10 to about 200, most preferably about 10 to about 30 nucleotides in length and is complementary to the extended first probes at a position beginning about 5 to about 2000, preferably about 5 to about 200, nucleotides downstream of the interrogation position in extended first probe, is annealed to the extended first probe, thereby forming the second hybrid. The second hybrids is extended at the 3'-end of the second probes until that extension reaches the 5'-end of the extended first probes, thereby forming a second extended hybrid whose 3'-region includes an identifier nucleotide. In preferred embodiments the extending polymerase for both extensions does not add a nucleotide to the 3' end that does not have a corresponding complementary nucleotide in the template.

An aqueous composition of the extended second hybrid is denatured to separate the two nucleic acid strands. The aqueous composition so formed is cooled to form a "hairpin structure" from the separated extended second probes when its respective target sequence is present in the original nucleic acid sample.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotide. The analytical output indicates the presence or absence of the various nucleic acid target sequences.

The present invention has many benefits and advantages, several of which are listed below.

One benefit of the invention is that, in some embodiments, a plurality of nucleic acid hybrids can be detected with very high levels of sensitivity without the need for radiochemicals or electrophoresis.

An advantage of the invention is that the presence or absence of a plurality of target nucleic acid(s) can be detected reliably, reproducibly, and with great sensitivity.

A further benefit of the invention is that quantitative information can be obtained about the amount of a target nucleic acid sequence present in a sample.

A further advantage of the invention is that very slight differences in nucleic acid sequence are detectable, including single nucleotide polymorphisms (SNPs).

Yet another benefit of the invention is that the presence or absence of a number of target nucleic acid sequences can be determined in the same assay.

Yet another advantage of the invention is that the presence or absence of target nucleic acids can be determined with a small number of reagents and manipulations.

Another benefit of the invention is that the processes lend themselves to automation.

Still another benefit of the invention is its flexibility of use in many different types of applications and assays including, but not limited to, detection of mutations, translocations, and SNPs in nucleic acid (including those associated with genetic disease), determination of viral load, species identification, sample contamination, and analysis of forensic samples.

Still further benefits and advantages of the invention will become apparent from the specification and claims that follow.

BRIEF DESCRIPTION OF THE DRAWING

In the drawings forming a portion of this disclosure,

FIG. 1 illustrates the annealing of the 10865 oligonucleotide (SEQ ID NO:82) to 10870 wild type (SEQ ID NO:83) and 10994 mutant (SEQ ID NO:84) oligonucleotides utilized in rolling circle amplification as FIG. 1A and FIG. 1B, respectively. Also shown are the annealing (hybridization) of oligonucleotide 10866 to oligonucleotide 10865, as well as the hybridization of oligonucleotide probe 10869 (SEQ ID NO:85) to oligonucleotide 10870 and of oligonucleotide probe 10989 (SEQ ID NO:86) to oligonucleotide 10994 as representations of the binding of those probes to the respective amplified sequences. Arcuate lines in oligonucleotide 10865 are used to help illustrate the shape that oligonucleotide 10865 can assume when hybridized with either of oligonucleotides 10870 or 10994.

FIG. 2. illustrates the Reaper™ assay as illustrated in Example 89. FIG. 2A illustrates the first hybrid formed by the annealing of nucleic acid target SEQ ID NO: 61 (61) to first probe SEQ ID NO:62 (62). An arrow points to an interrogation position in 286.

FIG. 2B illustrates the first extended hybrid formed by the annealing of 61 to the extended 62. Extended 287 is first extended probe SEQ ID NO:63 (63).

FIG. 2C illustrates the second hybrid formed by annealing of 63 from the denatured nucleic acid molecule shown in FIG. 2B to the second probe denoted SEQ ID NO:64 (64). An arrow points to the interrogation position in 63.

FIG. 2D illustrates the extended second hybrid formed by the annealing of 63 and the extended 64 strand denoted SEQ ID NO:65 (65).

FIG. 2E illustrates the 65 strand denatured from FIG. 2D and forming a hairpin structure. An arrow points to the interrogation position at the 3'-terminus of the hybrid.

DEFINITIONS

To facilitate understanding of the invention, a number of terms are defined below. "Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "dNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest," as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type," as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a variation from the most frequently occurring base at a particular nucleic acid position.

Homologous genes or alleles from different species are also known to vary in sequence. Regions of homologous genes or alleles from different species can be essentially identical in sequence. Such regions are referred to herein as "regions of identity." It is contemplated herein that a "region of substantial identity" can contain some "mismatches," where bases at the same position in the region of identity are different. This base position is referred to herein as "mismatch position." DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'- ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides may contain some modified linkages such as a phosphorothioate bond.

As used herein, the terms "complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The $T_m$ of a hybrid nucleic acid is often estimated using a formula adopted from hybridization assays in 1 M salt, and commonly used for calculating $T_m$ for PCR primers: $T_m$=[(number of A+T)×2° C.+(number of G+C)×4° C.]. C. R. Newton et al. *PCR*, $2^{nd}$ Ed., Springer-Verlag (New York: 1997), p. 24. This formula was found to be inaccurate for primers longer that 20 nucleotides. Id. Other more sophisticated computations exist in the art which take structural as well as sequence characteristics into account for the calculation of $T_m$. A calculated $T_m$ is merely an estimate; the optimum temperature is commonly determined empirically.

The term "homology", as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous."

When used in reference to a double-stranded nucleic acid sequence such as a cDNA or genomic clone, the term "substantially homologous", as used herein, refers to a probe that can hybridize to a strand of the double-stranded nucleic acid sequence under conditions of low stringency.

When used in reference to a single-stranded nucleic acid sequence, the term "substantially homologous", as used herein, refers to a probe that can hybridize to (i.e., is the complement of) the single-stranded nucleic acid template sequence under conditions of low stringency.

The term "interrogation position", as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide", as used herein, refers to a nucleotide whose presence is to be detected in a process of the invention to identify that a depolymerization reaction has occurred. The particular application of a method of the invention affects which residues are considered an identifier nucleotide. For a method using ATP detection (e.g. luciferase/luciferin or NADH) wherein, during analysis, all nucleotides released in the depolymerization are "converted" to ATP with an enzyme such as NDPK, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide may be labeled prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

The term "sample", as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection", as used herein, refers to quantitatively or qualitatively identifying a nucleotide or nucleic acid within a sample.

The term "depolymerization", as used herein, refers to the removal of a nucleotide from the 3' end of a nucleic acid.

The term "allele", as used herein, refers to an alternative form of a gene and the term "locus," as used herein, refers to a particular place on a nucleic acid molecule.

DETAILED DESCRIPTION OF THE INVENTION

A multiplex method of this invention is used to determine the presence or absence of a plurality of predetermined (known) nucleic acid target sequences in a nucleic acid sample. A nucleic acid target is "predetermined" in that its sequence must be known to design a probe that hybridizes with that target. However, it should be noted that a nucleic acid target sequence, as used with respect to a process of this invention can merely act as a reporter to signal the presence of a different nucleic acid whose presence is desired to be determined. That other nucleic acid of interest does not have to have a predetermined sequence. Furthermore, a process of the invention is useful in determining the identity of a base within a target where only enough of the sequence is known to design a probe that hybridizes to that target with partial complementarity at the 3'-terminal region of the probe.

Such a method utilizes an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

A nucleic acid target sequence is predetermined in that a nucleic acid probe is provided to be partially or totally complementary to that nucleic acid target sequence. A nucleic acid target sequence is a portion of nucleic acid sample with which the probe hybridizes if that target sequence is present in the sample.

A first step of the method is admixing a sample to be assayed with a plurality of nucleic acid probes. The admixing of the first step is typically carried out under low stringency hybridizing conditions to form a hybridization composition. In such a hybridization composition, the 3'-terminal region of the nucleic acid probes (i) hybridize with partial or total complementarity to a nucleic acid target sequence that may be present in the sample; and (ii) include an identifier nucleotide in the 3'-terminal region.

Preferably, a nucleic acid probe is designed to not hybridize with itself to form a hairpin structure in such a way as to interfere with hybridization of the 3'-terminal region of the probe to the target nucleic acid. Parameters guiding probe design are well known in the art.

The hybridization composition is maintained under hybridizing conditions for a time period sufficient to form a treated sample that may contain a plurality of predetermined nucleic acid target sequences hybridized with their respective nucleic acid probes.

In the event that the sample to be assayed does not contain a target sequence to which a probe hybridizes, no hybridization takes place for that probe. When a method of the present invention is used to determine whether a particular target sequence is present or absent in a sample to be assayed, the resulting treated sample may not contain a substrate for the enzymes of the present invention. As a result, a 3' terminal region identifier nucleotide is not released and the analytical output is at or near background levels.

The contemplated method is a multiplex assay in which a plurality of probes is utilized to determine whether one or more of a plurality of predetermined nucleic acid target sequences is present or absent in a sample. A particularly useful area for such multiplex assays is in screening assays where the usual analytical output indicates that the sought-after nucleic acid is absent.

In one illustrative embodiment, a nucleic acid sample is screened for the presence of a plurality of predetermined mutant nucleic acid. In this embodiment, the mutants usually are not present and the analytical output is, for example, at about background levels except where a mutation is present. In another embodiment, a plurality of samples is examined for the presence or absence of microbe-specific nucleic acid. Here, again, where a population of healthy individuals, animals, or presumably sterile food is sampled, the absence of the sought-after nucleic acid provides an analytical output that is about background levels, and only in the rare instance does a greater than the background output appear.

In a multiplexed embodiment of the above process, the sample is admixed with a plurality of different nucleic acid probes, preferably after amplification of the multiple nucleic acid targets as needed. In this embodiment of the invention, the analytical output for a certain result with one of the probes is distinguishable from the analytical output from the opposite result with all of the probes.

In preferred embodiments, the ATP produced via NDPK conversion of released nucleotides in the presence of ADP is detected by a luciferase detection system or an NADH detection system. In still another embodiment of the present invention, the pyrophosphate transferring step and the phosphate transferring step are performed in a single pot reaction. In other preferred embodiments, if increased sensitivity is required, the ATP molecules can be amplified.

In a contemplated multiplex embodiment, information about the presence or absence of a plurality of nucleic acid target sequences is determined using a process of the invention on a single nucleic acid sample, by admixing the sample with a plurality of nucleic acid probes for various nucleic acid targets.

In a first multiplex embodiment of the invention, the analytical output obtained when at least one of the nucleic acid probes hybridizes with partial complementarity to its target nucleic acid sequence is greater than the analytical output when all of the nucleic acid probes hybridize with total complementarity to their respective nucleic acid target sequences. Preferably, in such an embodiment, the enzyme whose activity is to depolymerize hybridized nucleic acid to release nucleotides exhibits a 3'→5'-exonuclease activity, depolymerizing hybridized nucleic acids having one or more mismatched bases at the 3'-terminus of the hybridized probe.

In a second multiplex embodiment of the invention, the analytical output obtained when at least one of said nucleic acid probes hybridizes with partial complementarity to its target nucleic acid sequence is less than the analytical output when all of the nucleic acid probes hybridize with total complementarity to their respective nucleic acid target sequences. Preferably, in such an embodiment, the enzyme whose activity is to depolymerize hybridized nucleic acid to release nucleotides is a template-dependent polymerase.

In a third multiplex embodiment of the invention, the analytical output obtained when at least one of said nucleic acid probes hybridizes with total complementarity to its nucleic acid target sequence is greater than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides is a template-dependent polymerase.

In a fourth multiplex embodiment of the invention, the analytical output obtained when at least one of said nucleic acid probes hybridizes with total complementarity to its target nucleic acid sequence is less than the analytical output when all of the nucleic acid probes hybridize with partial complementarity to their respective nucleic acid target sequences. Preferably, in such an embodiment, the enzyme whose activity is to depolymerize hybridized nucleic acid to release nucleotides exhibits a 3'→5-40 -exonuclease activity, depolymerizing hybridized nucleic acids having one or more mismatched bases at the 3'-terminus of the hybridized probe.

The treated sample is admixed with a depolymerizing amount of an enzyme whose activity is to release one or more identifier nucleotides from the 3'-terminus of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzyme reaction conditions is discussed in detail hereinafter.

The depolymerization reaction mixture is maintained under depolymerizing conditions for a time period sufficient to permit the enzyme to depolymerize hybridized nucleic acid and release identifier nucleotides therefrom to form a treated reaction mixture.

The presence or absence of released identifier nucleotides is then determined to obtain an analytical output. The analytical output indicates the presence or absence of a nucleic acid target sequence in the sample.

Processes of the invention can also be concerned with the degree of hybridization of the target to the $3^1$-terminal region of the probe. Examples hereinafter show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

In particular embodiments of the invention, it is desirable to include a destabilizing mismatch in or near the 3'-terminal region of the probe. In an example of such an embodiment, the goal is to determine whether a nucleotide at an interrogation position is a match or a mismatch with the target. Better discrimination between match and mismatch at the interrogation position is observed when an intentional mismatch is introduced about 2 to about 10 nucleotides from the interrogation position or preferably about 2 to about 6 nucleotides from the interrogation position.

The distinction of the analytical output between matched and mismatched nucleotides when there is more than a single base that is mismatched within the 3'-terminal region can be evident even if mismatches are beyond position 10 from the terminus, for example at position 11 and 12 upstream of the 3'-terminal nucleotide. Thus, the phrases "about 10" and "3'-terminal region" are used above. The 3'-terminal region therefore comprises the approximately 10 residues from the 3'-terminal nucleotide (or 3' terminus) position of a nucleic acid.

Hybridization conditions can be empirically ascertained for a control sample for various time periods, pH values, temperatures, nucleic acid probe/target combinations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

In one contemplated embodiment of the invention, the enzyme whose activity is to depolymerize hybridized nucleic acid to release nucleotides from the probe 3'-terminal end is a template-dependent polymerase. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

In an embodiment that uses a 3'→5' exonuclease activity of a polymerase, such as Klenow or T4 DNA polymerase (but not limited to those two enzymes), to depolymerize a nucleic acid probe, an identifier nucleotide is released when the 3'-terminal residue of the nucleic acid probe is mismatched and therefore there is only partial complementarity of the 3'-terminus of the nucleic acid probe to its nucleic acid target sequence. In this embodiment, to minimize background, the hybrid is typically purified from the un-annealed nucleic acid prior to the enzyme reaction, which releases identifier nucleotides. A signal confirms the presence of a nucleic acid target sequence that is not totally complementary to the nucleic acid probe.

In an embodiment that uses a 3'→5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide.

It is thus seen that hybridization and depolymerization can lead to the release of an identifier nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires for depolymerization activity.

The magnitude of a contemplated analytical output under defined conditions is dependent upon the amount of released nucleotides. Where an identifier nucleotide is released, an analytical output can be provided that has a value greater than background. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level Depolymerization reactions and enzymes useful in such reactions are discussed in more detail in the parental applications recited hereinbefore and incorporated herein by reference.

Template-dependent nucleic acid polymerases capable of pyrophosphorolysis include, but are not limited to, DNA polymerase α, DNA polymerase β, T4 DNA polymerase, Taq polymerase, Tne polymerase, Tne triple mutant polymerase, Tth polymerase, Tvu polymerase, Ath polymerase, Bst polymerase, *E. coli* DNA polymerase I, Klenow fragment, Klenow exo minus (exo-), AMV reverse transcriptase, RNA polymerase and MMLV reverse transcriptase. Most preferably, Klenow exo minus (Klenow exo-) or Tne triple mutant polymerase is utilized for DNA pyrophosphorolysis reactions because of their efficient utilization of 5' overhanging DNA ends.

In a preferred embodiment in the case of the reverse of polymerase activity (pyrophosphorolysis), a preferred substrate is a DNA probe hybridized to a nucleic acid target sequence with total complementarity at its 3'-terminus, including an identifier residue at the 3'-terminal region.

A depolymerization reaction can be catalyzed by bacteriophage T4 polymerase in the absence of NTPs depolymerizes a mismatched hybrid. In preferred embodiments, the released nucleotides, XMPs, are produced by nuclease digestion.

Nuclease digestion can be accomplished by a variety of nucleases that release a nucleotide with a 5' phosphate, including S1 nuclease, nuclease BAL 31, mung bean nuclease, exonuclease III and ribonuclease H. Nuclease digestion conditions and buffers are known in the art. Nucleases and buffers for their use are available from commercial sources.

In an embodiment of the invention where the enzyme's activity is a 3'→5' exonuclease activity, the hybridized nucleic acid probe is depolymerized from its 3'-terminal nucleotide. In a preferred embodiment in the case of a 3'→5' exonuclease activity of a polymerase, the preferred substrate is a nucleic acid probe hybridized to a nucleic acid target sequence with partial complementarity at its 3'-terminal region, most preferably with a mismatch at its 3'-terminal residue that is an identifier nucleotide.

Preferred reaction mixtures for depolymerization, including suitable buffers for each enzyme, are described in greater detail in the parent application and the Examples. Typically, under these conditions, sufficient NTP or DNTP is released to accurately detect or assay extremely low amounts of nucleic acids (e.g., about 5–1000 picograms).

In some preferred embodiments, oligonucleotide probes are typically utilized at about 100 ng to about 1 µg per 20 µL depolymerization reaction. That amount provides a probe to target weight ratio of about 200:1 to about 1,000:1.

In a preferred embodiment of the present invention, nucleic acid polymerase and pyrophosphate ($PP_i$) or an analogue thereof, are added to a hybridized sample containing from less than about 100 µg of target nucleic acid, to less than about 10 µg of nucleic acid. Typical target nucleic acids are present at about 1 to about 5 ng in the sample to be assayed, with a target nucleic acid length of about 30 to about 1000 bp being preferred.

A depolymerizing enzyme is preferably present in an amount sufficient to depolymerize a hybridized target:probe. That amount can vary with the enzyme used, the depolymerization temperature, the buffer, and the like, as are well-known in the art. For a typical reaction carried out in a 20 µL volume, about 0.25 to about 1 unit (U) of an enzyme such as Klenow exo- is used. About 1 to about 5 U of the thermostable enzymes are used for depolymerization at elevated temperatures.

Other conditions affecting the depolymerization reactions are discussed in the parent applications cited hereinabove, which are incorporated by reference.

Analytical Output

The analytical output is obtained by detection of the released identifier products, either the released nucleotides or the remainder of the probe. Exemplary detection systems include the light emitting luciferase detection system, the NADH light adsorption detection system (NADH detection system), fluorescence emissions and mass spectrometry. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods. Mass spectrometry of oligonucleotides is also becoming more common.

As is illustrated in the Examples that follow, it can be beneficial to carry out a contemplated method at elevated temperatures, e.g., about 50° C. to about 90° C. The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A,D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

A. Detection of ATP

Luciferase detection systems are particularly useful for detecting ATP. In the presence of ATP and oxygen, luciferase catalyzes the oxidation of luciferin, producing light that can then be quantified using a luminometer. Additional products of the reaction are AMP, pyrophosphate and oxyluciferin.

In particularly preferred embodiments, ATP detection buffer referred to as L/L reagent (Promega, FF2021) is utilized. Preferably, about 5 to 10 ng of luciferase are used in the reaction. Although it is not intended that the present invention be limited to a specific concentration of luciferase, greater amounts of luciferase have a tendency to increase non-specific background.

It is contemplated that in some embodiments, the dNTPs or NTPs produced by pyrophosphorolysis or nuclease digestion are converted to XTP, which can then be used directly as substrate for luciferase, permitting detection of the nucleic acid. However, the preferred substrate for luciferase is ATP, as demonstrated by Moyer and Henderson, *Anal. Biochem.*, 131:187–89 (1983). When DNA is the initial substrate, NDPK is conveniently utilized to catalyze the conversion of dNTPs to ATP by the following general reaction:

Reaction 4: dNTP*+ADP→dNDP+ATP* wherein dNTP is a mixture of deoxyribonucleoside triphosphates and dNDP is the corresponding deoxyribonucleoside diphosphate. In Reaction 4, the terminal 5'-triphosphate (P*) of the dNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPK, see Parks and Agarwal, in *The Enzymes*, Volume 8, P. Boyer Ed. (1973).

The conversion of NTPs or dNTPs to ATP by NDPK is preferably accomplished by adding NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice. Although yeast, bovine or another NDPK can be used in these reactions, it is preferred to utilize a thermostable NDPK such as the Pfu NDPK along with a thermostable depolymerizing enzyme such as the Tne triple mutant DNA polymerase (discussed below), Bst DNA polymerase, Ath DNA polymerase, Taq DNA polymerase and Tvu DNA polymerase along with a reaction temperature of about 50° C. to about 90° C. The use of these thermostable enzymes at an above temperature can enhance the sensitivity of the method. The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A,D389A).

B. Mass Spectrometric Analysis

In one method of the invention, the presence of released nucleotides is analyzed via mass spectrometry. In an embodiment of a method using mass spectrometry, the treated reaction mixture is ionized in a manner such that all components of the treated reaction mixture in the molecular weight range of the released identifier nucleotides are measured. Very small differences in molecular weight can be detected using mass spectrographic methods (different isotopes of the same atom are detectable), so any variation from a natural nucleic acid, including a single atom substitution (e.g. a fluorine in place of a hydrogen atom or a replacement of a hydrogen by a deuterium atom) in the identifier nucleotide gives rise to a detectable difference. Nucleic acid analogs used in methods of the invention should not interfere with either the hybridization of the nucleic acid probe or depolymerization of the hybridized probe.

Additionally, mass spectrometry can discriminate between individual nucleotides or nucleosides. For example, if the 3'-identifier nucleotide used in the instant invention was a G nucleotide, mass spectrometry can be used to detect the release of that G nucleotide in a method of the present invention. Similarly, mass spectrometry can detect the release of an A, T or C nucleotide, based on the differences in atomic weight of these compounds. Thus, in a multiplexing embodiment of the present invention, mass spectrometry can be used to resolve the presence of one or more of these 3'-identifier nucleotides.

In a particularly useful aspect of this embodiment, a mass spectral technique referred to as DIOS (desorption/ionization on silicon) was recently reported by Wei et al., *Nature*, 399:243(1999) that can accurately perform one or multiple assays on picogram or attagram amounts using commercially available mass spectrographs adapted with a specialized porous silicon sample well. The older, well known, MALDI mass spectrographic assay techniques can also be utilized.

In an embodiment of a multiplex method using mass spectrometry, multiple different identifier nucleotides can be used in the various nucleic acid probes. Using such a technique the presence of the different identifier nucleotides is direct evidence of the presence of the nucleic acid target sequences.

C. Fluorescence Spectroscopic Analysis

A wide variety of fluorescence detection methods can be used herein. In one exemplary contemplated method, an identifier nucleotide includes a fluorescent label. An identifier nucleotide can be fluorescently labeled prior to, or after, release of the identifier nucleotide. In an alternative embodiment when the nucleotide is fluorescently labeled, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN™ Life Science Products (Boston, Mass.), who offer dideoxy-, deoxy-, and ribonucleotide analogs a labeled with fluorescein, coumarin, tetramethylrhodamine, naphthofluorescein, pyrene, Texas Red®, and Lissamine™. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels. Such different labels would be particularly useful in a multiplex embodiment of the invention. Different fluorescent labels would be used in different probes, so that the detection of a particular fluorescently-labeled nucleotide analog as a released identifier nucleotide could be used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a released identifier nucleotide could be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include Nature, 193:167 (1962), *Methods Enzymol.* 26:28 (1972), *Anal. Biochem.*, 57:227 (1974), *Proc. Natl. Acad. Sci., U.S.*, 72:459 (1975).

It is contemplated that for many embodiments of the invention, it is useful to separate released fluorescent identifier nucleotides from those bound to an oligonucleotide, such as a probe. Thus, the separation techniques well known in the art and discussed above are useful with such an embodiment, including HPLC fitted with a fluorescence detector. The enhanced sensitivity of fluorescence relative to other spectroscopic techniques can be used to increase the sensitivity of a detection or quantification process of the invention.

In the NADH detection system, a combination of two enzymes, phosphoglycerate kinase and glyceraldehyde phosphate dehydrogenase, is used to catalyze the formation of NAD from NADH in the presence of ATP. Because NADH is fluorescent whereas NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB 2,055,200, all of which are herein incorporated by reference.

D. Absorbance Spectroscopic Analysis

An absorbance spectrographic analysis step is contemplated to provide an analytical output, thereby provide for the determination of the presence or absence released identifier nucleotide, and indicate the presence or absence of said nucleic acid target sequence. This embodiment contemplates the chromatographic separation of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo-, releasing the labeled nucleotides and other nucleotides from the 3'-termini of probes hybridized to target sequences when the 3' terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80$T_M$ or ODS-120T TSK-GEL by Toso-Haas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 5 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., *J. Chromatography*, 317:283–300 (1984), and Perrone & Brown, *J. Chromatography*, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions (as determined by continually monitoring the absorbance of the column effluent) can be determined by other standard analytical methods, such as nuclear magnetic resonance or atomic analysis (H,C,N).

In this illustrative example using depolymerization with Klenow exo-, the presence of a released identifier nucleotide from a particular probe indicates the presence of the target sequence that hybridize with that probe.

In an alternative embodiment, the released nucleotides from a depolymerization reaction mixture are separated on a gas chromatograph fitted with an absorbance detector to monitor column effluent.

Probe-Mediated Specific Nucleic Acid Detection

Depolymerization reactions can be used to interrogate the identity of a specific base in a nucleic acid. For example, the identity of single base point mutations, deletions, or insertions in a nucleic acid can be determined as follows.

In one embodiment, each nucleic acid probe synthesized is substantially complementary to a target nucleic acid containing or suspected of containing a point mutation. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid.

A nucleic acid probe comprises single-stranded nucleic acid (e.g., DNA or RNA). A probe can be of varying lengths, preferably from about 10 to 100 bases, most preferably about 10 to 30 bases. In particularly preferred embodiments, a probe is complementary to the target at all bases between an interrogation position and 3' end of the nucleic acid probe.

In preferred embodiments, a probe is designed to have a predetermined nucleotide at an interrogation position. When a complementary probe base pairs or hybridizes to a target nucleic acid, the base at an interrogation position aligns with the base in the nucleic acid target whose identity is to be determined under conditions such that base pairing can occur. It is contemplated that an interrogation position can be varied within the probe. For example, in some preferred embodiments, an interrogation position is preferably within 10 bases of the 3' end of the nucleic acid probe. In still other preferred embodiments, an interrogation position is within 6 bases of the 3' end of the nucleic acid probe. In particularly preferred embodiments, an interrogation position is at the next to last or last base at the 3' end of the nucleic acid probe.

In an interrogation embodiment wherein the identity of a base at the interrogation position is desired, four different probes, preferably of equal length, are synthesized, each having a different nucleotide at an interrogation position. Accordingly, it is contemplated that in some embodiments, a set of DNA probes includes a first probe with a deoxyadenosine residue at an interrogation position, a second probe with a deoxythymidine residue at an interrogation position, a third probe with a deoxyguanosine residue at an interrogation position, and a fourth probe with a deoxycytosine residue at an interrogation position. Likewise, it is also contemplated that a set of RNA probes includes a first probe with an adenosine residue at an interrogation position, a second probe with a uridine residue at an interrogation position, a third probe with a guanosine residue at an interrogation position, and a fourth probe with a cytosine residue at an interrogation position.

In the next step of that interrogation embodiment, the probes are hybridized to the target nucleic acid, if the target nucleic acid is present in the sample, so that a probe nucleic acid-target nucleic acid complex is formed. It is contemplated that hybridization conditions can vary depending on the length and base composition of the probes. In the probe-target nucleic acid complex, the nucleotide at an interrogation position is aligned with the specific base to be identified in the nucleic acid. In the contemplated multiplex embodiment, a set of probes can be used simultaneously. Because the probes differ at an interrogation position, only one of the probes is complementary to the specific base in the target nucleic acid that is aligned with an interrogation position. Preferably, the probes are distinguishable, most preferably the identifier nucleotides are different between the four probes, for example using mass spectrometry or different fluorescent labels.

In the next step of that interrogation embodiment, the nucleic acid probe-target nucleic acid complexes are reacted under conditions permitting depolymerization of the probe. The preferred reaction conditions for depolymerization are described in the parent applications and in the following Examples. The released nucleotides are then detected.

In particularly preferred embodiments, the identity of a specific base is determined by comparing the amount of signal produced from each probe. Depolymerization of a hybridized probe proceeds from its 3' end. When the base at an interrogation position is not complementary to the specific base in the nucleic acid, very little or no signal is produced.

In yet another preferred embodiment, the probe-mediated specific nucleic acid detection method of the present invention can be used to simply identify or detect a nucleic acid of interest. For this method, nucleic acid probes (e.g., DNA or RNA) are utilized, each of which is substantially complementary to its respective target nucleic acid, which can be RNA or DNA. In a particularly preferred embodiment, each nucleic acid probe is entirely complementary to its target nucleic acid. A nucleic acid probe comprises single-stranded nucleic acid (e.g., DNA or RNA). The probe can be of varying lengths, preferably from about 10 to about 1000 bases, most preferably about 10 to 100 bases.

Detection is carried out as described above. The nucleic acid probe-nucleic acid target complex is exposed to conditions permitting depolymerization of the probe, which results in the production of XTPs. Detection of the nucleic acid of interest is characterized by a difference in the signal generated by the XTPs produced when compared to control sample reactions. For probes completely complementary to their target nucleic acid in the presence of a depolymerizing enzyme which removes matched identifier nucleotides, a signal greater than background would indicate the presence of at least one of the target nucleic acids in the original sample. In a preferred embodiment, each probe contains a distinguishing identifier nucleotide and the detection of an identifier nucleotide released from the target/probe hybrid would determine the presence of a specific target nucleic acid in the original sample.

The ability to interrogate the identity of a specific base in a nucleic acid also permits discrimination between nucleic acids from different species, or even from different alleles. The ability to detect and discriminate between nucleic acids of related or unrelated species also permits the identification of species contained within a given nucleic acid-containing sample. For example, the method can be used to determine which species of several related bacteria or virus are contained within a sample (e.g., clinical samples, environmental samples, food samples, or samples from non-human animals).

In preferred embodiments of this method, nucleic acids with substantially identical sequences from at least two species or alleles are detected. The region of identity (target nucleic acid sequence) contains at least a single nucleotide mismatch between the species or alleles in at least one predetermined position and also contains a 3' end and a 5' end or the identification of a nucleic acid sequence unique to each species to be identified.

Next, in some embodiments, an RNA or DNA probe that is substantially complementary to the region of identity is synthesized. The probe can be of varying lengths, preferably from about 10 to 1000 bases, most preferably about 10 to 100 bases. As above, this complementary probe includes an interrogation position.

An interrogation position can be varied within the probe. For example, an interrogation position is preferably within 10 bases of the 3' end of the nucleic acid probe. More preferably, an interrogation position is within 6 bases of the 3' end of the nucleic acid probe. Most preferably, an interrogation position is at the next to last or last base of the 3' end of the nucleic acid probe.

The nucleic acid probes are designed so that the base at an interrogation position is complementary to the nucleotide at the predetermined position of one species or allele, but not another due to the mismatch. Likewise, a second probe can be synthesized that is complementary at an interrogation position to the nucleotide at the predetermined position of a second species or allele.

A contemplated procedure is employed to identify the presence or absence of multiple species within a given sample. In these embodiments, all that is required is the identification of substantially identical sequences between species that contain base mismatches or the identification of a nucleic acid sequence unique to each species to be identified.

A method contemplated by the present invention has wide applicability in assaying nucleic acids. In some aspects, an endogenous nucleic acid is assayed to determine whether a particular native or mutant sequence is present or absent. This type of analysis is sometimes referred to as genotyping because the genetic makeup of the subject from which the nucleic acid sample is obtained is determined. Speciation, the identity of an organism, such as the identification of a human, dog, chicken, bovine or the like can be determined by use of species-specific nucleic acid probes such as probes to selected regions of the gene encoding cytochrome B.

Using a contemplated method, one can illustratively determine whether a human patient, for example, has the Leiden V mutation, a mutant β-globin gene, the cystic fibrosis-related gene in the region of the delta 508 allele, a mutation in a prothrombin gene, congenital adrenal hyperplasia, a translocation that takes place in the region of the bcr gene along with involvement of a segment of the abl gene, the number of repeated sequences in a gene such as are present in THO 1 alleles or the TPOX alleles, as well as the loss of heterozygosity of the locus of certain alleles as is found in certain cancers and also allelic trisomy. Genomic typing can also be used to assay plant genomes such as that of rice, soy or maize to determine if they contain non-native sequences. The presence or absence in a sample of the genomes of microbes such as *Campylobacter jejuni,* Listeria, and *E. coli* OH157 can be determined, and viral genomes such as that of cytomegalovirus (CMV) or human immunodeficiency virus (HIV) can be analyzed to determine whether a drug-resistant strain is present in a sample.

A contemplated method can also be utilized to assay for the presence or absence of nucleic acid that is exogenous to the source of the sample. For example, a contemplated method can be used to assay for the presence of viruses such as hepatitis C virus (HCV), cytomegalovirus (CMV), human immunodeficiency virus (HIV), as well as to determine the viral load in an organism with a disease, such as a human or a plant. A contemplated method can also be used to identify the presence of an exogenous nucleic acid sequence in a plant such as maize, soy or rice. A contemplated method can also be used to assay for the presence of microorganisms such as *Listeria monocytogenes,* Campylobacter spp., Salmonella spp., Shigella spp. or *Escherichia coli* (including *E. coli* E0157) in foodstuffs such as meats, dairy products, and fruit juices.

The determination of an appropriate nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing PCR primers can be used to assist in the design of probes for use in the invention.

In one illustrative embodiment, the predetermined nucleic acid target sequences are associated with blood coagulation, and the nucleic acid probes comprise sequences complementary to nucleic acid sequences associated with blood coagulation. Exemplary sequences associated with blood coagulation comprise (a) a sequence of at least ten nucleotides of the Factor V gene in the region of the Leiden mutation or the corresponding wild type sequence of the Factor V gene; and (b) a sequence of at least ten nucleotides of a prothrombin gene. Preferred exemplary sequences are selected from the group consisting of SEQ ID NO:14, SEQ ID NO:15, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:47, SEQ ID NO:44, SEQ ID NO:45 and SEQ ID NO:46 and their complementary sequences.

| FV5 | 5' CTGCTGCCCTCTGTATTCCTCG 3' | SEQ ID NO:14 |
|---|---|---|
| FV6 | 5' CTGCTGCCCTCTGTATTCCTTG 3' | SEQ ID NO:15 |
| PT7 | 5' GTGACTCTCAGCG 3' | SEQ ID NO:87 |
| PT8 | 5' GTGACTCTCAGCA 3' | SEQ ID NO:88 |
| PT9 | 5' GTGATTCTCAGCG 3' | SEQ ID NO:89 |
| PT10 | 5' GTGATTCTCAGCA 3' | SEQ ID NO:90 |
| FV7 | 5' GACAAAATACCTGTATTCCTCG 3' | SEQ ID NO:91 |
| FV8 | 5' GACAAAATACCTGTATTCCTTG 3' | SEQ ID NO:92 |
| PT3 | 5' GGAGCATTGAGGCTCG 3' | SEQ ID NO:93 |
| PT4 | 5' GGAGCATTGAGGCTTG 3' | SEQ ID NO:94 |
| 11432 | 5' GACAAAATACCTGTATTCCTTG 3' | SEQ ID NO:47 |
| 11265 | 5' GTGATTCTCAGCA 3' | SEQ ID NO:44 |
| 11266 | 5' GTGATTCTCAGCG 3' | SEQ ID NO:45 |
| 9919 | 5' GACAAAATACCTGTATTCCTCG 3' | SEQ ID NO:46 |

In another contemplated embodiment, the speciation of a nucleic acid sample is determined using a suite of species probes in a single assay. Kits containing probes for such an assay are also contemplated. Exemplary probes shown to be specific for human mitochondrial DNA are SEQ ID NO:50)) and 11583 (SEQ ID NO:51)). An exemplary common probe, 11582 (SEQ ID NO:52), gives a positive reaction with bovine, chicken, dog and human species. An exemplary chicken-specific probe, 11577 (SEQ ID NO:53), is specific for chicken mitochondrial DNA, while another chicken-specific probe, 11584 (SEQ ID NO:54), gives a signal with bovine and human in addition to chicken genomic DNA. An exemplary cow-specific probe, 11588 (SEQ ID NO:55), provides a strong signal with cow target DNA, but also gives a signal with human, chicken and dog nucleic acid. An exemplary dog-specific probe, 11586 (SEQ ID NO:56), provides a stronger signal with dog DNA than it does with cow DNA. The sequences complementary to the probes listed below are also contemplated as probe sequences.

| 11576 | huzoo1 | 5' CCAGACGCCTCA 3' | SEQ ID NO:50 |
|---|---|---|---|
| 11583 | huzoo2 | 5' ACCTTCACGCCA 3' | SEQ ID NO:51 |
| 11582 | comzoo | 5' TGCCGAGACGT 3' | SEQ ID NO:52 |
| 11577 | chzoo1 | 5' GCAGACACATCC 3' | SEQ ID NO:53 |
| 11584 | chzoo2 | 5' GGAATCTCCACG 3' | SEQ ID NO:54 |
| 11588 | cozoo2 | 5' ACATACACGCAA 3' | SEQ ID NO:55 |
| 11586 | dozoo2 | 5' ATATGCACGCAA 3' | SEQ ID NO:56 |

In a further embodiment, genetic screening for a target sequence in a nucleic acid sample is contemplated using a plurality of probes to the various targets in a single assay. Kits containing probes for such genetic testing are also contemplated. In an exemplary embodiment, the steroid 21-hydroxylase gene is screened for mutations correlated with a group of autosomal recessive diseases collectively known as congenital adrenal hyperplasia (CAH). Exemplary CAH probes for use in a method and kit according to the invention are listed below. The complementary sequences to the probes listed below are also contemplated as probe sequences.
11143 5'CGGAGCCTCCACCTCCCG SEQ ID NO:23
CAH interrogator oligo 6 (wild type) for mutation site 1
11085 5'CACCCTCCAGCCCCCAGC 3' SEQ ID NO:24
CAH interrogator oligo 2 (pseudogene/mutant) for mutatuion site 2
11084 5'CGGAGCCTCCACCTCCTG 3' SEQ ID NO:25
CAH interrogator oligo 1 (pseudogene/mutant) for mutation site 1
11086 5'CCTCACCTGCAGCATCAAC 3' SEQ ID NO:26
CAH interrogator oligo 3 (pseudogene/mutant) for mutation site 3
11144 5'CACCCTCCAGCCCCCAAC 3' SEQ ID NO:27
CAH interrogator oligo 7 (wild type) for mutation site 2
11145 5'CCTCACCTGCAGCATCATC 3' SEQ ID NO:28
CAH interrogator oligo 8 (wild type) for mutation site 3
11087 5'CCTGGAAGGGCACTT 3' SEQ ID NO:29
CAH interrogator oligo 4 (pseudogene/mutant) for mutation site 4
11146 5'CCTGGAAGGGCACGT 3' SEQ ID NO:30
CAH interrogator oligo 9 (wild type) for mutation site 4
11088 5' GATTCAGCAGCGACTGTA 3' SEQ ID NO:31
CAH interrogator oligo 5 (pseudogene/mutant) for mutation site 5
11147 5' GATTCAGCAGCGACTGCA 3' SEQ ID NO:32
CAH interrogator oligo 10 (wild type) for mutation site 5
11287 5'CGAGGTGCTGCGCCTGCG 3' SEQ ID NO:33
CAH interrogation oligo 11 (wild type) for mutation site 6
11288 5'CGAGGTGCTGCGCCTGTG 3' SEQ ID NO:34
CAH interrogation oligo 12 (pseudogene/mutant) for mutation site 6
11641 5'GGGATCACATCGTGGAGATG 3' SEQ ID NO:35
CAH interrogation oligo 23 (wild type) for mutation site 7
11642 5'GGGATCACAACGAGGAGAAG 3' SEQ ID NO:36
CAH interrogation oligo 24 (pseudogene/mutant) for mutation site 7

Preferably in an assay of genomic or mitochondrial, or otherwise large, complex nucleic acid sample sources using a multiplex method of the invention, a segment of nucleic acid from the genome or mitochondrial nucleic acid is amplified or otherwise isolated to make a sample for conducting a hybridization assay according to the invention. Alternatively, a method of the invention that results in multiple depolymerizable hybrids in the presence of a single target molecule as discussed in the copending application U.S. Ser. No. 09/358,972, filed on Jul. 21, 1999, is preferred, for example assays forming hairpins (e.g. REAPER™), or using self-annealing primers.

In another exemplary multiplex embodiment, predetermined nucleic acid target sequences are associated with cystic fibrosis, and the nucleic acid probes comprise sequences complementary to nucleic acid sequences associated with cystic fibrosis. In one embodiment of this aspect, the target and probes are associated with the cystic fibrosis delta F508 mutation. Particularly preferred exemplary cystic fibrosis-associated sequences are SEQ ID NO:95 or SEQ ID NO:96 and their complementary sequences.
CF3 5'CATCATAGGAAACACCAAG 3' SEQ ID NO:95
CF4 5'CATCATAGGAAACACCAAT 3' SEQ ID NO:96

Information is currently available and will continue to be made available during the lifetime of this patent as to certain nucleic acid sequences that are associated with various species or diseases. It is contemplated that any of these nucleic acid sequences are useful in a method of the invention and that combinations of probes to the various targets are useful in a multiplex kit according to the present invention.

An exemplary cancer-associated nucleic acid sequence discussed in more detail in the parent application, U.S. Ser. No. 09/358,972, filed on Jul. 21, 1999, is contemplated for use in a multiplex genetic screening kit and method along with other probes. The nucleic acid probes BA3 (SEQ ID NO:97) and BA4 (SEQ ID NO:98) are useful in detecting a particular translocation that takes place in the region of the bcr gene, and a segment of the abl gene that is involved with the translocation.

BA3 5' TGGATTTAAGCAGAGTTCAAGT 3' SEQ ID NO:97
BA4 5' TGGATTTAAGCAGAGTTCAAAA 3' SEQ ID NO:98

Amplification of the Sample Target or a Detection Target

A target nucleic acid sequence is typically amplified prior to use of a contemplated method. However, where a sufficient number of repeated nucleotide sequences are present in the native sample as in the human Alu sequence or the *E. coli* rep sequence, amplification is often not needed prior to carrying out a contemplated method.

Several methods are known in the art to amplify a region of DNA. These include polymerase chain reaction, ligase chain reaction, repair chain reaction, amplification of transcripts, self-sustained sequence replication (3SR), ligation activated transcription (LAT), strand displacement amplification (SDA) and rolling circle replication. A claimed process contemplates prior treatment of a nucleic acid sample using any amplification method known in the art at the time of practicing a claimed process to detect the presence of a nucleic acid target in the sample.

Multiplex Assays Using Hairpin Structures

Although it is preferred that the probes be constructed to be free of hairpin structures, assays in which hairpin structures are constructed are also useful. An embodiment of the invention contemplates use of a hairpin structure for determining the presence or absence of a plurality of nucleic acid target sequences in a nucleic acid sample with a probe that is hybridized to the target and then modified to be able to form a hairpin structure. This embodiment comprises the following steps.

A treated sample is provided that contains a nucleic acid sample that may include a plurality of nucleic acid target sequences having an interrogation position. The target sequences, if present in the nucleic acid sample hybridize with their respective nucleic acid probes. A probe is comprised of at least two sections. The first section contains the probe 3'-terminal about 10 to about 30 nucleotides. These nucleotides are complementary to the target strand sequence at positions beginning about 1 to about 30 nucleotides downstream of the interrogation position. The second section of the probe is located at the 5'-terminal region of the probe and contains about 10 to about 20 nucleotides of the target sequence. This same sequence, therefore, exists in both the target and the probe in the same 5' to 3' orientation. This sequence spans the region in the target from the nucleotide at or just upstream (5') of the interrogation position, to the nucleotide just upstream to where the 3'-terminal nucleotide of the probe anneals to the target. An optional third section of the probe, from zero to about 50, preferably from zero to about 20, nucleotides in length and comprising a sequence that does not hybridize with either the first or second section, is located between the first and second sections of the probe.

The hybridized probes of the treated sample are extended in a template-dependent manner, by admixture with dNTPs and a template-dependent polymerase, at least through the interrogation position, thereby forming an extended probe/target hybrid. In a preferred embodiment, the length of the probe extension is limited by omission from the extension reaction of a DNTP complementary to a nucleotide of the target sequence that is present upstream of the interrogation position and absent between the nucleotide complementary to the 3'-end of the interrogation position.

The extended probe/target hybrid is separated from any unreacted dNTPs; i.e., purified at least to the degree needed to use the extended probe strand to determine the presence or absence of the interrogation region in the sample or the identity of the base at the interrogation position. The extended probe/target hybrid is denatured to separate the strands. The extended probe strands are permitted to form hairpin structures.

It is preferred that the polymerase enzyme utilized for an extension reaction be a template-dependent polymerase that is free of activity that adds a 3'-terminal deoxyadenosine in a template-nonspecific manner. Thus, it is preferred to use other than a polymerase such as Taq for a contemplated extension.

A treated reaction mixture is formed by admixing the hairpin structure-containing composition with a depolymerizing amount of an enzyme whose activity is to release one or more nucleotides from the 3'-terminus of an extended probe hairpin structure. The reaction mixture is maintained under depolymerizing conditions for a time period sufficient for the depolymerizing enzyme to release 3'-terminus nucleotides, and then analyzed for the presence of released identifier nucleotides. The analytical output indicates the presence or absence of the nucleic acid target sequence. That analytical output can be determined as discussed elsewhere herein.

A still further embodiment of the invention, such as that termed REAPER™ and demonstrated in Example 89 and FIG. 2, also contemplates use of hairpin structures in determining the presence or absence of a nucleic acid target sequence, or a specific base within the target sequence, in a nucleic acid sample, and comprises the following steps. A treated sample is provided that contains a nucleic acid sample that may include a plurality of nucleic acid target sequences hybridized with its respective first nucleic acid probe strand (FIG. 2A).

The hybrid is termed the first hybrid. The first probes are comprised of at least two sections. The first section contains the probe 3'-terminal about 10 to about 30 nucleotides that are complementary to the target nucleic acid sequence at a position beginning about 5 to about 30 nucleotides downstream of the target interrogation position. The second section of a first probe contains about 5 to about 30 nucleotides that are a repeat of the target sequence from the interrogation position to about 10 to about 30 nucleotides downstream of the interrogation position, and does not hybridize to the first section of the probe. That is, the second sequence is a repeat of the region in the target sequence from the interrogation position downstream to the position where the 3'-terminal nucleotide of the first probe aligns with the target. An optional third section of the probe, located between the first and second sections of the probe, is zero to about 50, preferably to about 20, nucleotides in length and comprises a sequence that does not hybridize to either the first or second section.

The first hybrid in the treated sample is extended at the 3'-end of the first probes, thereby extending the first probe past the interrogation position and forming an extended first hybrid (FIG. 2B) whose sequence includes an interrogation position. The extended first hybrid is comprised of the original target nucleic acid and extended first probe. The extended first hybrid is then denatured in an aqueous composition to separate the two nucleic acid strands of the hybridized duplex and form an aqueous solution containing separated target nucleic acids and separated extended first probes.

Second probes are about 10 to about 2000, more preferably about 10 to about 200, most preferably about 10 to about 30 nucleotides in length and are complementary to their respective extended first probes at a position beginning about 5 to about 2000, preferably about 5 to about 200, nucleotides downstream of the interrogation position in extended first probe, anneal to the extended first probes, thereby forming the second hybrid (FIG. 2C). The second hybrid is extended at the 3'-end of the second probes until that extension reaches the 5'-end of the extended first probes, thereby forming a second extended hybrid (FIG. 2D) whose 3'-region includes an identifier nucleotide.

An aqueous composition of the extended second hybrid is denatured to separate the two nucleic acid strands; i.e., the extended second probes and the extended first probes. The aqueous composition so formed is cooled to form a "hairpin structure" from the separated extended second probes (FIG. 2E) when the target sequence is present in the original nucleic acid sample. Thus, when the target sequence is present in the original nucleic acid sample, the 3'-terminal sequence of the second extended probes in the second extended hybrid hybridize with the sequence of the second extended probes from a region comprising the interrogation position and nucleotides downstream from the interrogation position of second extended probe to the nucleotide position where the 3'-terminal nucleotide of the original (first-named) probes annealed to the original target.

A treated reaction mixture is formed by admixing the hairpin structure-containing composition with a depolymerizing amount of an enzyme whose activity is to release one or more nucleotides from the 3'-terminus of a nucleic acid hybrid. The reaction mixture is maintained under depolymerizing conditions for a time period sufficient to release 3'-terminal region identifier nucleotides, and then analyzed for the presence of released identifier nucleotides. The analytical output indicates the presence or absence of the various nucleic acid target sequences. Again, the analytical output can be determined by one of the several methods discussed elsewhere herein. In one embodiment of this multiplex hairpin-forming probe method, the analytical outputs from the various nucleic acid target sequences are distinguishable.

As was the case in the previous embodiment, dNTPs are utilized in the extension reactions. It is preferred that the hairpin structures be separated from the dNTPs prior to depolymerization to enhance the analysis for the identifier nucleotide.

Kits

Other embodiments of the invention contemplate a kit for determining the presence or absence of a plurality of predetermined nucleic acid target sequences in a nucleic acid sample. Such a kit comprises an enzyme whose activity is to release one or more nucleotides from the 3' terminus of a hybridized nucleic acid probe and at least one nucleic acid probe, said nucleic acid probe being complementary to a nucleic acid target sequence.

Preferably the enzyme whose activity is to release nucleotides in the kit is a template dependent polymerase that, in the presence of pyrophosphate ions, depolymerizes hybridized nucleic acids whose bases in the 3'-terminal region are matched with total complementarity. Alternatively, the enzyme whose activity is to release nucleotides in the kit exhibits a 3' to 5' exonuclease activity, depolymerizing hybridized nucleic acids having one or more mismatched bases at the 3' terminus of the hybridized probe.

In a preferred embodiment, the enzyme capable of catalyzing pyrophosphorolysis is, but is not limited to Taq polymerase, Tne polymerase, Tne triple mutant polymerase, Tth polymerase, Tvu polymerase, Ath polymerase, T4 DNA polymerase, Klenow fragment, Klenow exo minus, E. coli DNA polymerase I, AMV reverse transcriptase, MMLV reverse transcriptase, or poly(A) polymerase. In another preferred embodiment, the kit contains an exonuclease such as Si nuclease, nuclease BAL 31, mung bean nuclease, exonuclease III and ribonuclease H.

Either of the above enzyme types is utilized in a contemplated method in a depolymerizing effective amount. That is, the enzyme is used in an amount that depolymerizes the hybridized probe to release an identifier nucleotide. This amount can vary with the enzyme used and also with the temperature at which depolymerization is carried out. An enzyme of a kit is typically present in an amount that conveniently permits the distribution of about 0.1 to 100 U per reaction; in particularly preferred embodiments, the concentration is about 0.5 U/reaction. An amount of enzyme sufficient to carry out at least one assay, with its controls is provided.

In an alternative preferred embodiment, the enzyme whose activity in the presence of pyrophosphate is to release identifier nucleotides is a thermostable polymerase. Preferred thermostable polymerases are the Tne triple mutant DNA polymerase, Klenow exo-, Klenow, T4 DNA polymerase, Ath DNA polymerase, Taq DNA polymerase and Tvu DNA polymerase, the Tne triple mutant DNA polymerase and Tvu DNA polymerase are particularly preferred.

It is to be understood that such a kit is useful for any of the methods of the present invention. The choice of particular components is dependent upon the particular method the kit is designed to carry out. Additional components can be provided for detection of the analytical output, as measured by the release of identifier nucleotide, or by detection of the remaining probe after depolymerization.

In one embodiment, a kit has nucleic acid probes that comprise fluorescent labels. In a method using such a kit, either the released identifier nucleotide or the remaining probe is determined using fluorescence spectroscopy, depending on the location of the fluorescent label within the probe. In an alternative embodiment, the released nucleotides are separated from depolymerized probes, and the remaining probe or released nucleotide is fluorescently labeled. Such an embodiment contemplates the provision of fluorescent labels and/or a magnetic nucleic acid separation medium. The above fluorescent embodiments contemplate that the fluorescent labels are distinguishable.

In another embodiment, a kit has nucleic acid probes that comprise a non-natural nucleotide analog as an identifier nucleotide. In a contemplated method using such a kit, the depolymerization is assayed for using mass spectrometry.

The kit optionally further comprises instructions for detecting said nucleic acid by depolymerization. The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In one embodiment, the invention contemplates a kit for determining the presence or absence of a plurality of predetermined nucleic acid target sequences in a nucleic acid sample comprising the following components: an enzyme whose activity in the presence of pyrophosphate is to release identifier nucleotide as a nucleoside triphosphate from hybridized nucleic acid probe; pyrophosphate; and a plurality of nucleic acid probes, wherein the nucleic acid probes are complementary to their respective predetermined nucleic acid target sequence.

The enzyme whose activity in the presence of pyrophosphate is to release identifier nucleotide is as described hereinabove. Preferably, the plurality of nucleic acid probes are for related applications for a useful and convenient multiplex assay. For example, the detection of several genetic disease markers (e.g. Factor V Leiden and prothrombin), a suite of human identity screens, the detection of a series of harmful microorganisms (e.g. certain *E. coli* strains, *camphylobacter jejuni,* and salmonella or HIV-I, HIV-II, drug-resistant HIV-I, Hepatitis C and Hepatitis B), or to check a plant for a series of nucleic acids. Several examples of such probes are discussed hereinabove.

In a contemplated kit for multiplexed probe-mediated specific nucleic acid detection, the kit contains a plurality of nucleic acid probes for nucleic acid targets of interest. Preferably, where the kits contain multiple probes, each of the probes is designed to interrogate a different target DNA sequence.

The invention also contemplates kits containing instructions for use in interrogating the identity of a specific base within a nucleic acid target using a plurality of probes with different bases at the interrogation position and distinguishable probes. The invention also contemplates kits containing instructions for use in simultaneously discriminating between two homologous nucleic acid targets that differ by one or more base pairs by providing a distinguishable probe for each target. Alternatively, the invention contemplates a kit containing instructions for use in the simultaneous discrimination between a suite of nucleic acid targets that differ from a homologous nucleic acid target by one or more base pairs using distinguishable probes. The invention further contemplates a kit containing instructions for use in determining whether a sample contains a plurality of nucleic acid targets having a deletion or insertion mutation. The types of nucleic acid probes that can be included in the kits and their uses are described in greater detail below.

EXAMPLE 1

Multiplex Analysis of Alleles at One Interrogation Site

For a wide variety of genetic disorders, only a very small percentage of samples will have a particular single nucleotide polymorphism (SNP) at any one site. For this reason, it can be much more efficient in these cases to screen for the presence of groups of mutant alleles and to perform secondary, single probe tests only if there is a positive signal for any of the probes designed to detect the mutant sites. Such a form of multiplex analysis will be performed in this example.

Multiple probes designed to detect a mutant form of a gene in the CMV genome are used in one reaction and the signal from this reaction is compared to that from a probe that is specific for the non-mutated sequence. In this example, the SNP sites are separated by only one base and the alleles are provided as pure nucleic acid target species.

Oligonucleotides CV19 (SEQ ID NO:1) and CV20 (SEQ ID NO:2) encode a segment of the CMV genome around position 1784 of the viral genome and these probes encode the non-mutant form of a gene.

Oligonucleotides CV21 (SEQ ID NO:3) and CV22 (SEQ ID NO:4) encode the same genome segment as CV19 and CV20 but encode a form of the gene where a Leu codon in the encoded protein is altered to encode a Ser codon.

Oligonucleotides CV23 (SEQ ID NO:5) and CV24 (SEQ ID NO:6) also encode the same genome segment as CV19 and CV20, but these oligonucleotides encode a form of the genome where the same Leu codon mutated in CV21 and CV22 is altered to a Phe codon. These oligonucleotides are used here as target nucleic acids for interrogation in this example.

Oligonucleotide probe CV25 (SEQ ID NO:7) exactly matches a region of CV19 and is designed to detect the non-mutated form of the gene. oligonucleotide probe CV26 (SEQ ID NO:8) exactly matches a segment within CV21 and is designed to detect the version of the gene where the Leu codon has been mutated to a Ser codon. oligonucleotide probe CV27 (SEQ ID NO:9) exactly matches a segment within CV24 and is designed to detect the version of the target where the Leu codon has been mutated to a Phe codon.

The target nucleic acid pairs CV19 and CV20, CV21 and CV22, and CV23 and CV24 were dissolved at 1 mg/mL in water, annealed by heating the solutions 95° C. for 5 minutes and permitting to cool at room temperature for 10 minutes. Subsequently, the solutions were diluted to 3.3 µg/mL with water. The probes CV25, CV26 and CV27 were dissolved at 1 mg/mL in water.

The following solutions were assembled.

| Solution | CV (19 + 20) | CV (21 + 22) | CV (23 + 24) | CV25 | CV26 | CV27 | Water |
|---|---|---|---|---|---|---|---|
| #1 and #2 | 1 µL | — | — | 1 µL | — | — | 18 µL |
| #3 and #4 | 1 µL | — | — | — | 1 µL | 1 µL | 17 µL |
| #5 and #6 | — | 1 µL | — | 1 µL | — | — | 18 µL |
| #7 and #8 | — | 1 µL | — | — | 1 µL | 1 µL | 17 µL |
| #9 and #10 | — | — | 1 µL | 1 µL | — | — | 18 µL |
| #11 and #12 | — | — | 1 µL | — | 1 µL | 1 µL | 17 µL |

These solutions were heated at 95° C. for three minutes then cooled at room temperature for 10 minutes.
The following master mix was assembled and mixed.

| Component | Volume |
| --- | --- |
| 10X DNA Polymerase Buffer (Promega, M195A) | 60 μL |
| 40 mM Sodium Pyrophosphate (Promega, C350B) | 7.5 μL |
| Klenow exo- (10 U/μL) (Promega, M218B) | 7.5 μL |
| NDPK (1 U/μL) | 3 μL |
| 10 μM ADP | 6 μL |
| Water | 216 μL |

After solutions 1–12 had cooled at room temperature, 20 μL of this master mix were added to each solution, and the solutions were heated to 37° C. for 15 minutes. After this heating step, a 4 μL sample of each solution was added to 100 μL L/L reagent (Promega, F202A) and the light produced by the resulting reaction was read immediately using a Turner® TD 20/20 luminometer. The following results were obtained.

| Solution samples | Relative Light Units |
| --- | --- |
| #1 | 115.7 |
| #2 | 120.9 |
| #3 | 20.85 |
| #4 | 20.10 |
| #5 | 9.99 |
| #6 | 9.41 |
| #7 | 102.4 |
| #8 | 95.2 |
| #9 | 12.56 |
| #10 | 12.54 |
| #11 | 240.3 |
| #12 | 238.9 |

The results from the duplicate solutions were averaged and are presented in the table below.

| | Average Signal from Probe Types | | |
| --- | --- | --- | --- |
| Nucleic Acid Target | Wild Type Probe | Mutant Probes Multiplexed | Ratio* |
| Wild Type Target | 118.3 | 20.48 | 5.78 |
| Leu to Ser Target | 9.7 | 98.8 | 0.10 |
| Leu to Phe Target | 12.6 | 239.6 | 0.05 |

*Ratio is determined by dividing the signal from the wild type probe by the signal from the multiplexed mutant probes.

These data show that the use of both mutant probes in one reaction permits either probe to give a signal if the appropriate target is added to the reaction. The signal ratios produced by the probes designed to detect the mutant target when either probe matches the target are significantly different than from when the wild type target is used with the wild type probe. Thus, comparison of the signals as described above permits the user to know that a mutation is present in the tested target at either of the interrogation sites.

CV19
5' CTCTTTAAGCACGCCGGCGCGGCCTGC-CGCGCGTTGGAGAACGGCAAGCTCACGCA 3' SEQ ID NO:1

CV20
5'CAGCAGTGCGTGAGCTTGCCGTTCTC-CAACGCGCGGCAGGCCGCGCCGGCGTGCTT 3' SEQ ID NO:2

CV21
5'CTCTTTAAGCACGCCGGCGCGGCCTGC-CGCGCGTCGGAGAACGGCAAGCTCACGCA 3' SEQ ID NO:3

CV22
5'CAGCAGTGCGTGAGCTTGCCGTTCTC-CGCGCGCGGCAGGCCGCGCCGGCGTGCTT 3' SEQ ID NO:4

CV23
5'CTCTTTAAGCACGCCGGCGCGGCCTGC-CGCGCGTTTGAGAACGGCAAGCTCACGCA 3' SEQ ID NO:5

CV24
5'CAGCAGTGCGTGAGCTTGCCGTTCT-CAAACGCGCGGCAGGCCGCGCCGGCGTGCTT 3' SEQ ID NO:6

CV25 5' GGCGCGGCCTGCCGCGCGTTG 3' SEQ ID NO:7

CV26 5' GGCGCGGCCTGCCGCGCGTCG 3' SEQ ID NO:8

CV27 5' GCGTGAGCTTGCCGTTCTCCG 3' SEQ ID NO:9

EXAMPLE 2

Multiplexed Genome Analysis on Multiple Templates

For a wide variety of genetic disorders, only a very small percentage of samples exhibit a particular single nucleotide polymorphism at any one site. For this reason, it can be more efficient in these cases to screen for the presence of groups of mutant alleles and to perform secondary, single probe tests only if there is a positive signal for any of the probes designed to detect the mutant sites. Such a form of multiplex analysis will be performed in this example.

Multiple probes designed to detect a mutant form of two different target genes are used in one reaction, and the signal from this reaction is compared to that from a probe that is specific for one of the non-mutated sequences. Thus, in this example, multiple SNP sites on multiple targets are interrogated in one reaction.

The targets and probes used in this study are: FV(1+2) (SEQ ID NO:10 and SEQ ID NO:11, respectively) FV(3+4) (SEQ ID NO:12 and SEQ ID NO:13, respectively), FV5 (SEQ ID NO:14), FV6 (SEQ ID NO:15), 9162 (SEQ ID NO:16), 9165 (SEQ ID NO:17), 9163 (SEQ ID NO:18), 9166 (SEQ ID NO:19), and CV2 (SEQ ID NO:20). A synthetic first nucleic acid target of the Factor V gene was designed to have the wild type sequence that contains a G at position 32 of FV1 (SEQ ID NO:10). The complementary strand, FV2, (SEQ ID NO:11) has 4 additional bases at its 3' terminus. A second synthetic nucleic acid target of Factor V was designed to have the Leiden mutation, an A residue at position 32 of FV3. The mutant complementary strand, FV4, also had 4 additional bases at its 3' terminus. The nucleic acid target oligonucleotides, FV1 to FV4, were separately dissolved at a concentration of one mg/mL in water. Oligonucleotides 9162 and 9163 are complementary and have a segment of the wild type CMV genome. Oligonucleotides 9163 and 9166 are complementary and have the same segment of the viral genome, but they contain a single base change present in a known drug resistant form of the virus. Equal volumes of one mg/mL 9162 and 9165 were combined to serve as wild type target for CMV. Equal volumes of one mg/mL 9163 and 9166 were combined to serve as the mutant target for CMV. Oligonucleotide CV2 represents an oligonucleotide designed to detect the drug resistant form of the CMV sequence.

All the target DNAs [FV(1+2), FV(3+4), 9162+9165, 9163+9166] were diluted to 0.3 μg/mL with water. The other oligonucleotides were dissolved to 1 mg/mL with water. These compositions were used to assemble the following solutions.

| Soln | FV5 | FV6 | CV2 | 9162 + 9165 | 9163 + 9166 | FV(1 + 2) | FV(3 + 4) | Water |
|---|---|---|---|---|---|---|---|---|
| 1  | —    | —    | —    | —    | —    | —    | —    | 20 μL |
| 2  | —    | 1 μL | —    | —    | —    | —    | —    | 19 μL |
| 3  | —    | —    | 1 μL | —    | —    | —    | —    | 19 μL |
| 4  | —    | 1 μL | 1 μL | —    | —    | —    | —    | 18 μL |
| 5  | —    | —    | —    | 1 μL | —    | —    | —    | 19 μL |
| 6  | —    | —    | —    | —    | 1 μL | —    | —    | 19 μL |
| 7  | —    | —    | —    | —    | —    | 1 μL | —    | 19 μL |
| 8  | —    | —    | —    | —    | —    | —    | 1 μL | 19 μL |
| 9  | —    | —    | —    | 1 μL | —    | 1 μL | —    | 18 μL |
| 10 | —    | —    | —    | 1 μL | —    | —    | 1 μL | 18 μL |
| 11 | —    | —    | —    | —    | 1 μL | 1 μL | —    | 18 μL |
| 12 | —    | —    | —    | —    | 1 μL | —    | 1 μL | 18 μL |
| 13 | —    | —    | —    | —    | —    | —    | —    | 20 μL |
| 14 | 1 μL | —    | —    | 1 μL | —    | 1 μL | —    | 17 μL |
| 15 | 1 μL | —    | —    | —    | 1 μL | 1 μL | —    | 17 μL |
| 16 | 1 μL | —    | —    | 1 μL | —    | —    | 1 μL | 17 μL |
| 17 | 1 μL | —    | —    | —    | 1 μL | —    | 1 μL | 17 μL |
| 18 | —    | 1 μL | 1 μL | 1 μL | —    | 1 μL | —    | 16 μL |
| 19 | —    | 1 μL | 1 μL | —    | 1 μL | 1 μL | —    | 16 μL |
| 20 | —    | 1 μL | 1 μL | 1 μL | —    | —    | 1 μL | 16 μL |
| 21 | —    | 1 μL | 1 μL | —    | 1 μL | —    | 1 μL | 16 μL |

These 21 solutions, in triplicate, were heated to 92° C. for 11 minutes, then cooled approximately 1 hour at room temperature.

The following master mix was assembled and mixed.

| Component | Volume |
|---|---|
| Water | 1008 μL |
| 10X DNA Polymerase Buffer (Promega, M195A) | 280 μL |
| Klenow exo- (1 U/μL) (Promega, M218B) | 35 μL |
| 40 mM Sodium Pyrophosphate (Promega, C350B) | 35 μL |
| 10 μM ADP | 28 μL |
| NDPK (1 U/μL) | 14 μL |

After cooling at room temperature, 20 μL of the master mix were added to each of the 21 solutions, in triplicate, and they were heated at 37° C. for 15 minutes then placed on ice.

Five microliter samples of the solutions were placed in wells of a microtiter plate such that a 5 μL sample of each solution, in triplicate, was present within each plate and three such plates were prepared. The plates were placed into a Luminoskan® microtiter plate reading luminometer and this instrument was programmed to add 100 μL of L/L reagent (Promega, F120B) to each well and immediately read the light produced by the reaction in the well. The individual readings for each solution within each plate were averaged and these averages are given below.

| | | Relative Light Units | | | |
|---|---|---|---|---|---|
| Target | Probe(s) | Plate 1 | Plate 2 | Plate 3 | Average of Plates |
| none | FV5 | 5.08 | 2.81 | 2.99 | 3.63 |
| none | FV6 | 2.85 | 2.72 | 3.59 | 3.05 |
| none | CV2 | 2.91 | 2.73 | 2.60 | 2.75 |
| none | FV6 and CV2 | 2.56 | 2.75 | 2.68 | 2.66 |
| 9162 + 9165 | none | 2.67 | 2.59 | 2.50 | 2.59 |
| 9163 + 9166 | none | 2.72 | 2.59 | 2.51 | 2.61 |
| FV(1 + 2) | none | 2.80 | 2.52 | 2.55 | 2.62 |
| FV(3 + 4) | none | 2.75 | 2.41 | 2.51 | 2.56 |
| 9162 + 9165 + FV(1 + 2) | none | 2.57 | 2.53 | 2.34 | 2.48 |
| 9162 + 9165 + FV(3 + 4) | none | 2.54 | 2.46 | 2.40 | 2.47 |
| 9163 + 9166 + FV(1 + 2) | none | 2.40 | 2.39 | 2.45 | 2.41 |
| 9163 + 9166 + FV(3 + 4) | none | 2.48 | 2.35 | 2.42 | 2.42 |
| none | none | 2.53 | 2.34 | 2.22 | 2.36 |
| 9162 + 9165 + FV(1 + 2) | FV5 | 25.61 | 28.23 | 24.08 | 25.97 |
| 9162 + 9165 + FV(1 + 2) | FV6 and CV2 | 4.75 | 4.53 | 4.32 | 4.53 |
| 9163 + 9166 + FV(1 + 2) | FV5 | 25.36 | 27.72 | 28.98 | 27.35 |
| 9163 + 9166 + FV(1 + 2) | FV6 and CV2 | 44.69 | 41.14 | 45.29 | 43.71 |
| 9162 + 9165 + FV(3 + 4) | FV5 | 3.91 | 3.93 | 4.16 | 4.00 |
| 9162 + 9165 + FV(3 + 4) | FV6 and CV2 | 32.23 | 30.57 | 36.55 | 33.12 |
| 9163 + 9166 + FV(3 + 4) | FV5 | 3.54 | 3.64 | 3.52 | 3.57 |

-continued

Relative Light Units

| Target | Probe(s) | Plate 1 | Plate 2 | Plate 3 | Average of Plates |
|---|---|---|---|---|---|
| 9163 + 9166 + FV(3 + 4) | FV6 and CV2 | 58.61 | 59.14 | 71.77 | 63.17 |

The light values for the reactions were adjusted from the averaged plate values above by subtracting the average No-DNA signal value and target-alone averages and probe-alone values from the total light value measured for the various target and probe combinations. Reactions involving combinations of Target/Probe were further corrected by subtracting the appropriate adjusted probe-alone and target-alone values to yield a net light value. The resulting values are shown in the table below.

| Targets | FV5 Probes | Mutant Probes |
|---|---|---|
| WT CMV, WT Factor V | 22.22 | 1.76 |
| Mutant CMV, WT Factor V | 23.68 | 41.00 |
| WT CMV, Mutant Factor V | 0.27 | 30.35 |
| Mutant CMV, Mutant Factor V | (−.12) | 60.46 |

As in the previous example, a very distinctive signal pattern is seen with the various target combinations that were studied. This indicates that using multiple mutant probes in a multiplex manner can reduce the number of reactions needed to determine if a mutant site is present within the sample. These data show for this assay system that when the signal from the mutant probe reactions approaches or is greater than that seen with the corresponding wild type probe, the sample contains a target with a mutation in at least one of the sites. In addition, if the signal for the wild type (WT) probe is far lower than that for the multiplexed mutant probes, it is likely that at least the target interrogated by the wild type probe is in the mutant form.

FV1 5'CTAATCTGTAAGAGCAGATCCTGGA-CAGGCGAGGAATACAGAGGGCAGCAGA-CATCGAAGAGCT 3' SEQ ID NO:10
FV2 5'AGCTCTTCGATGTCTGCTGCCCTCTG-TATTCCTCGCCTGTCCAGGGATCT-GCTCTTACAGATTAGAGCT 3' SEQ ID NO:11
FV3 5'CTAATCTGTAAGAGCAGATCCTGGA-CAGGCAAGGAATACAGAGGGCAGCAGA-CATCGAAGAGCT 3' SEQ ID NO:12
FV4 5'AGCTCTTCGATGTCTGCTGCCCTCTG-TATTCCTTGCCTGTCCAGGGATCT-GCTCTTACAGATTAGAGCT 3' SEQ ID NO:13
FV5 'CTGCTGCCCTCTGTATTCCTCG 3' SEQ ID NO:14
FV6 'CTGCTGCCCTCTGTATTCCTTG 3' SEQ ID NO:15
9162 5'CGTGTATGCCACTTTGATATTACAC-CCATGAACGTGCTCATCGACGTCAAC-CCGCACAACGAGCT 3' SEQ ID NO:16
9165 5'CGTTGTGCGGGTTCACGTCGATGAG-CACGTTCATGGGTGTAATATCAAAGTG-GCATACACGAGCT 3' SEQ ID NO:17
9163 5'CGTGTATGCCACTTTGATATTACAC-CCGTGAACGTGCTCATCGACGTCAAC-CCGCACAACGAGCT 3' SEQ ID NO:18
9166 5'CGTTGTGCGGGTTCACGTCGATGAG-CACGTTCACGGGTGTAATATCAAAGTG-GCATACACGAGCT 3' SEQ ID NO:19
CV2 5'CACTTTGATATTACACCCGTG 3' SEQ ID NO:20

EXAMPLE 3

Specific Detection of RNA:

Comparison of Signals from RNA Species that Match Probe Sequences in Reactions With and Without Added Extraneous Target RNA For the pyrophosphorylation reaction using DNA probes that match RNA sequences to be used to detect specific target sequences, the system should give a very similar signal in the presence and absence of extraneous RNA. In this Example, the strength of the signal of probes designed to detect target globin mRNA in the presence of a large amount of yeast RNA is compared to the signal seen in the absence of added yeast RNA. Hybridization solutions containing various levels of yeast RNA, Probe 6 (SEQ ID NO:21) or Probe 8 (SEQ ID NO:22) and target globin MRNA (Gibco BRL, 18103-028) were assembled by adding 5 μL of a 500 ng/μL solution of either probe 6 or probe 8 to 5 μL of a 40 ng/μL solution of target globin MRNA and 10 μL yeast RNA (Sigma Chemical Co. R3629) in 1×TE buffer (10 mM Tris, 1 mM EDTA) to produce solutions containing total amounts of yeast RNA of 0, 2, 20, 200, 400, and 800 ng. The solutions were heated at 50° C. for 15 minutes and then permitted to cool to room temperature for 15.

The following master reaction mixture was assembled:

| | |
|---|---|
| Nanopure water | 346.5 μL |
| MMLV-RT 5X Reaction Buffer (Promega M195A) | 132 μL |
| Sodium pyrophosphate (Promega M531) | 16.5 μL |
| NDPK (1 U/μL) | 33 μL |
| ADP (2 μM) | 33 μL |
| MMLV-RT (adjusted to 100 U/μL) (Promega, M1701) | 33 μL |

The solution above was mixed and 18 μL of the mix were placed in 18 tubes. After cooling 15 minutes, 2 μL of the various hybridization solutions containing probe 6 were added to the tubes and the tubes were placed in a 37° C. heating block.

After 15 minutes of incubation of the hybridization mixture with the reaction master mix, 20 μL of the solution were added to 100 μL of L/L reagent (Promega, F202A) and the light output of the resulting reaction was measured using a Turner® TD-20/20 luminometer.

After the probe 6 data were collected, an identical set of reactions was performed using the hybridization solutions containing probe 8.

The following data were obtained:

| | Probe 6 Reactions | | | |
|---|---|---|---|---|
| Yeast RNA | relative light units | | | Average |
| None | 96 | 109 | 111 | 105.3 |
| 2 ng | 98.4 | 85.0 | 118.5 | 100.7 |
| 20 ng | 117.9 | 110.9 | 82.7 | 103.65 |

-continued

Probe 6 Reactions

| Yeast RNA | relative light units | | | Average |
|---|---|---|---|---|
| 200 ng | 56.4 | 110.1 | 93.2 | 86.6 |
| 400 ng | 115.7 | 110.7 | 124.6 | 117 |
| 800 ng | 127.6 | 128.7 | 143.1 | 133.1 |

Probe 8 Reactions

| Yeast RNA | relative light units | | | Average |
|---|---|---|---|---|
| None | 105.8 | 97.0 | 82.3 | 95.0 |
| 2 ng | 84.5 | 84.6 | 93.7 | 87.6 |
| 20 ng | 99.6 | 111.7 | 104.9 | 105.4 |
| 200 ng | 83.6 | 75.9 | 95.6 | 85.1 |
| 400 ng | 94.7 | 97.2 | 81.9 | 91.2 |
| 800 ng | 50.7 | 89.0 | 82.1 | 73.9 |

These data indicate that addition of very large amounts of yeast RNA to the hybridization reaction does not greatly lower the signal from hybridized probes for specific target RNA species.

| Probe 6 | SEQ ID NO:21 | 5'AGACTTCTCCTCACTGGACAGATGCACCAT3' |
|---|---|---|
| Probe 8 | SEQ ID NO:22 | 5'GGGTCCATGGGTAGACAACCAGCAGC3' |

EXAMPLE 4

Multiplex Analysis of Congenital Adrenal Hyperplasia (CAH) Gene

The use of thermostable enzymes to interrogate the CAH gene permits the interrogation of up to 6 multiple sites within one reaction. The method used in this Example is illustrative of routine studies carried out in screening laboratories where usual results show the presence of an expected gene (or the absence of a mutant gene) in almost all of the samples, and only rarely shows the presence of a mutant gene. In the case illustrated here, a qualitative result is provided from which the exact mutation present can be determined in a subsequent assay.

Congenital adrenal hyperplasia (CAH) is a group of autosomal recessive diseases resulting from a wide range of mutations in the steroid 21-hydroxylase (CYP21) gene that contains 10 exons. There is a high level of nucleic acid homology (98% in exons, 96% in introns) between CYP21, the functional gene, and CYP21P, the nonfunctional pseudogene. The many types of mutations in this gene that can lead to disease include complete gene deletions, large gene conversions, single point mutations, and a small 8bp deletion [See, White, et al., *Hum. Mutat.*, 3:373–378, (1994)].

The majority of the CAH disease-causing mutations are sequences present in the nonexpressed CY21P pseudogene, and arise in the CYP21 gene through recombination between CYP21P and CYP21. Thus, one mutation detection strategy specifically detects the CYP21 gene, and not the CYP21P pseudogene. The frequency of disease-carrying alleles in the population is about 1 in 50. Both wild type CAH PCR products, mutant synthetic targets, and a pseudogene PCR product amplified from the cloned CYP21P pseudogene were utilized as targets in this assay. They are listed below.

Primer pairs used in PCR amplification and the resulting products are as follows.

| Primers | Size PCR Segment | Segment Amplified |
|---|---|---|
| 10912 + 10909 | 1400 bp | 5' end CYP21 |
| 11461 + 11480 | 918 bp | 5' end CYP21 |
| 10910 + 11286 | 1492 bp | 3' end CYP21 |
| 11535 + 11286 | 1496 bp | 3' end CYP21 |
| 10912 + 10911 | 2680 bp | pseudogene (CYP21P) |

Synthetic targets and interrogation oligos utilized are listed below.

PCR reactions were assembled to amplify regions of the CAH gene with 4 different probe sets, using undigested human genomic DNA (Promega, G3041) as target (25 ng per reaction). For amplification of the pseudogene, human genomic DNA was predigested with the restriction enzyme Bcl I, which specifically cleaves the CYP21 gene upstream of the forward PCR probe, thus permitting only amplification of CYP21P [Krone, *Clinical Chem.* 44(10):2075–2082 (1998)].

The 2680 bp PCR product was amplified from 50 ng of digested DNA and subsequently cloned into the plasmid vector PGEM-T Easy (Promega, A1380) following the manufacturer's protocol. A clone was selected and sequenced (USB Sequenase kit, US70770) to confirm it was indeed the pseudogene. The cloned CYP21P gene in the pGEM-T Easy vector was used in subsequent amplifications to obtain pure pseudogene PCR product for mutation interrogation analysis (100 pg of plasmid per PCR reaction).

All 50 μL amplification reactions contained the following reagents: genomic DNA (as described above), 1×reaction buffer (M1901), 1.0–1.5 mM magnesium chloride (all with 1.0 mM except probe pair 10912+10911 for pseudogene, which contained 1.5 mM MgCl$_2$; Promega, A3511), 200 μM each DNTP (C1141), 50 pmoles each probe, and 2.5 units Taq DNA Polymerase (M1665).

The following cycling profile was utilized for all amplifications: 5 minutes at 95° C.; 40 cycles of 30 seconds at 94° C., 1 minute at 55° C., 1 minute per kbp of product at 72° C.; 8 minutes at 68° C.; soak at 4° C. The products were analyzed on 1% agarose gels and compared to DNA molecular weight standards to confirm product sizes were correct. An aliquot of each PCR reaction (25 μL) was then treated with 50 units T7 Gene6 Exonuclease (USB, E70025Y) for 15 minutes at 37° C., followed by purification using the Wizard™ PCR Prep DNA Purification System (Promega, A7170) with 3×1 mL 80% isopropanol washes. The exonuclease-treated DNA was eluted in 100 μL of nuclease-free water.

Equal volumes of the CAH wild type (WT) 918 bp and 1496 bp PCR products were combined (to thus span the entire CAH gene) and interrogated either separately at each mutation site, or as a multiplexed group.

Each interrogation assay (20 μL total volume) contained 4 μL of purified PCR product or 5 ng of synthetic target, and 1 μg interrogation oligo probe (or water for the no-oligo background control). The reactions were incubated at 95° C. for 3 minutes, followed by 10 minutes at 37° C. for Klenow exo- or 55° C. for Tne polymerase. Twenty microliters of master mix were added (2 mM sodium pyrophosphate, 0.2 μM ADP, 2×polymerase buffer (M195A for Klenow or M41901 for Tne), 5 mM magnesium chloride for Tne only, 1-2 U Klenow exo- and 0.2 U yeast NDPK or 1 U Tne triple mutant polymerase and 0.1 U Pfu NDPK) and the reaction incubated 15 minutes at 37° C. (Klenow exo-) or 55° C. (Tne). The entire reaction was then added to 100 μL of L/L reagent (Promega FF202A) and light output read in a Turner® TD20/20 luminometer.

The discrimination ratio was good both in the separate reactions for the combined PCR products, as well as the multiplexed reaction. In addition, the multiplexed reaction using the CAH wild type PCR products and either 6 wild type interrogation oligo probes or 6 mutant interrogation oligo probes was combined with an equimolar amount of synthetic target (mutant synthetic target for each mutation site; 0.2 pmoles either PCR product or synthetic target), to simulate a heterozygote sample.

| Target DNA | Tne/Pfu NDPK, No Oligo | Tne/Pfu NDPK, WT Oligo | Tne/Pfu NDPK Mutant Oligo | Probe for Mutation Site | Mutant Synthetic Target Added |
|---|---|---|---|---|---|
| CAH WT 918 bp + 1496 bp | 172.7 | 553.0 | 180.2 | 1 | |
| Same | 172.7 | 535.7 | 184.0 | 2 | |
| Same | 172.7 | 494.8 | 182.0 | 3 | |
| Same | 172.7 | 486.7 | 148.7 | 4 | |
| Same | 172.7 | 471.7 | 187.9 | 5 | |
| Same | 172.7 | 317.5 | 179.7 | 6 | |
| Same | 172.7 | 297.5 | 246.4 | 7 | |
| Same | 523.7 | 1929.0 | 499.5 | 1, 2, 3, 4, 5 and 6 | |
| Same | 506.0 | 1882.0 | 2234.0 | 1 | 1 |
| Same | 525.4 | 1848.0 | 1505.0 | 2 | 2 |
| Same | 535.9 | 1735.0 | 2877.0 | 3 | 3 |
| Same | 547.5 | 1880.0 | 4879.0 | 4 | 4 |
| Same | 552.4 | 2000.0 | 3864.0 | 5 | 5 |
| Same | 482.9 | 1938.0 | 2189.0 | 6 | 6 |
| Same | 514.5 | 1791.0 | 4192.0 | 2 + 4 | 2 + 4 |
| Same | 537.6 | 1752.0 | 3427.0 | 5 + 6 | 5 + 6 |

Because of the large size of the CAH gene and the large number of different mutations that may be present, the use of the thermostable enzymes, and thus the increased stringency of the detection procedure, was found to be highly advantageous with this complex target. Mutation sites that interrogated poorly using Klenow exo- and yeast NDPK at 37° C., were more successfully interrogated when using the Tne triple mutant polymerase and Pfu NDPK at elevated temperatures. In addition, use of the thermostable enzymes permitted the multiplexing of numerous wild type or mutant interrogation oligos in the same interrogation assay, to obtain the rapid screening for mutations that may be present.
PCR PRIMERS UTILIZED:
10909 5'CCAGAGCAGGGAGTAGTCTC 3' SEQ ID NO:66
CAH reverse primer; 5' most 3 linkages phosphorothioate (CYP21 only)
10912 5' GCATATAGAGCATGGCTGTG 3' SEQ ID NO:67
CAH forward primer
10910 5'CCTGTCCTTGGGAGACTAC 3' SEQ ID NO:68
CAH forward primer (CYP21 only)
10911 5'CCCAGTTCGTGGTCTAGC 3' SEQ ID NO:69
CAH reverse primer; 5' most 3 linkages phosphorothioate
11286 5' TCCTCACTCATCCCCAAC 3' SEQ ID NO:70
CAH reverse primer; 5' most 3 linkages phosphorothioate
11461 5'GAAATACGGACGTCCCAAGGC SEQ ID NO:71
CAH forward primer
11480 5'CTTTCCAGAGCAGGGAGTAG SEQ ID NO:72
CAH reverse primer; 5' most 3 linkages phosphorothioate (CYP21 only)
11535 5'CCGGACCTGTCCTTGGGAGA SEQ ID NO:73
CAH forward primer (CYP21 only)
SYNTHETIC TARGETS UTILIZED:
11293 5' AGAAGCCCGGGGCAAGAGGCAGGAGGTG-GAGGCTCCGGAG 3' SEQ ID NO:74
CAH Synthetic Target 1 for Interrogator oligo 1 (pseudogene/mutant—exon 1)
Mutation site 1
11294 5' AGCTTGTCTGCAGGAG-GAGCTGGGGGCTGGAGGGTGGGAA 3' SEQ ID NO:75
CAH Synthetic Target 2 for Interrogator oligo 2 (pseudogene/mutant—intron 2)
Mutation site 2
11295 5' TCCGAAGGTGAGGTAACAGTTGATGCTG-CAGGTGAGGAGA 3' SEQ ID NO:76
CAH Synthetic Target 3 for Interrogator oligo 3 (pseudogene/mutant—exon 4)
Mutation site 3
11296 5' TCCACTGCAGCCATGTGCAAGTGCCCT-TCCAGGAGCTGTC 3' SEQ ID NO:77
CAH Synthetic Target 4 for Interrogator oligo 4 (pseudogene/mutant—exon 7)
Mutation site 4
11297 5' TCGTGGTCTAGCTCCTCCTACAGTCGCT-GCTGAATCTGGG 3' SEQ ID NO:78
CAH Synthetic Target 5 for Interrogator oligo 5 (pseudogene/mutant—exon 8)
Mutation site 5
11298 5' GCTAAGGGCACAACGGGCCACAGGCG-CAGCACCTCGGCGA 3' SEQ ID NO:79
CAH Synthetic Target 6 for Interrogator oligo 12 (pseudogene/mutant—exon 8)
Mutation site 6
11484 5'CAGCTTGTCTGCAGGAGGAGT-TGGGGGCTGGAGGGTGGGA 3' SEQ ID NO:80
CAH Synthetic Target 7 for Interrogator oligo 7 (wild type—intron 2)
Mutation site 2
11485 5'GGCTAAGGGCACAACGGGCCGCAGGCG-CAGCACCTCGGCG 3' SEQ ID NO:81
CAH Synthetic Target 8 for Interrogator oligo 11 (wild type—exon 8)
Mutation site 6
INTERROGATION OLIGOS PROBES UTILIZED:
11143 5'CGGAGCCTCCACCTCCCG 3' SEQ ID NO:23
CAH interrogator oligo 6 (wild type) for mutation site 1
11085 5'CACCCTCCAGCCCCCAGC 3' SEQ ID NO:24
CAH interrogator oligo 2 (pseudogene/mutant) for mutation site 2
11084 5'CGGAGCCTCCACCTCCTG 3' SEQ ID NO:25
CAH interrogator oligo 1 (pseudogene/mutant) for mutation site 1
11086 5'CCTCACCTGCAGCATCAAC 3' SEQ ID NO:26
CAH interrogator oligo 3 (pseudogene/mutant) for mutation site 3
11144 5'CACCCTCCAGCCCCCAAC 3' SEQ ID NO:27
CAH interrogator oligo 7 (wild type) for mutation site 2
11145 5'CCTCACCTGCAGCATCATC 3' SEQ ID NO:28
CAH interrogator oligo 8 (wild type) for mutation site 3

11087 5'CCTGGAAGGGCACTT 3' SEQ ID NO:29
CAH interrogator oligo 4 (pseudogene/mutant) for mutation site 4
11146 5'CCTGGAAGGGCACGT 3' SEQ ID NO:30
CAH interrogator oligo 9 (wild type) for mutation site 4
11088 5' GATTCAGCAGCGACTGTA 3' SEQ ID NO:31
CAH interrogator oligo 5 (pseudogene/mutant) for mutation site 5
11147 5' GATTCAGCAGCGACTGCA 3' SEQ ID NO:32
CAH interrogator oligo 10 (wild type) for mutation site 5
11287 5'CGAGGTGCTGCGCCTGCG 3' SEQ ID NO:33
CAH interrogation oligo 11 (wild type) for mutation site 6
11288 5'CGAGGTGCTGCGCCTGTG 3' SEQ ID NO:34
CAH interrogation oligo 12 (pseudogene/mutant) for mutation site 6
11641 5'GGGATCACATCGTGGAGATG 3' SEQ ID NO:35
CAH interrogation oligo 23 (wild type) for mutation site 7
11642 5'GGGATCACAACGAGGAGAAG 3' SEQ ID NO:36
CAH interrogation oligo 24 (pseudogene/mutant) for mutation site 7

EXAMPLE 5

HPLC Separation of dNTPs
After Interrogation Assay, but Prior to Phosphate Transfer and Light Production Large-volume pyrophosphorylation assays were performed on matched and mismatched probe/target hybrids. The released nucleotides were separated by high performance liquid chromatography (HPLC) and their fractions collected. NDPK terminal phosphate transfer reactions were performed on these concentrated fractions and luciferase assays conducted to illustrate discrimination between the original matched and mismatched hybrid treated samples.

Target/probe hybrids were formed by combining 315 ng of the synthetic wild type CMV target oligonucleotide with either 10.5 µg wild type CMV probe for a matched hybrid, or 10.5 µg mutant CMV probe for a mismatched hybrid, and adding water to a final volume of 200 µL. The oligonucleotides were CV 12 (SEQ ID NO:37), CV 15 (SEQ ID NO:38), and CV 16 (SEQ ID NO:39). CV12 (SEQ ID NO:37) is a single-stranded DNA segment of the genome of cytomegalovirus (CMV) in a form sensitive to the drug gancyclovir. CV 15 (SEQ ID NO:38) is a probe that hybridizes with total complementarity to the non-resistant CMV. CV 16 (SEQ ID NO:39) is identical to CV 15 (SEQ ID NO:38) except that it contains a one base change from the CV15 sequence at the site of the SNP that confers drug resistance to the virus. These solutions were heated to 95° C. for at least 5 minutes, then cooled at room temperature for at least 10 minutes.

The following master mix was prepared.

| | |
|---|---|
| 337.5 µL | Nanopure water (Promega, AA399) |
| 90.0 µL | 10X DNA Polymerase buffer (Promega, M195A) |
| 11.25 µL | 40 mM NaPPi (Promega, C113) |

Master mix (210 µL) was added to each of the above hybrid solutions and 5.8 units of Klenow exo- (Promega, M218A) were added to each. The solutions were then incubated at 37° C. for 15 minutes and stored on ice. HPLC separation of the dNTPs was performed.

HPLC separation of DATP, dCTP, dGTP and TTP was performed on a 100×4.6 mm, 3 g Luna C18 column [Perrone and Brown, *J. Chromatography*, 317:301–310 (1984)] from Phenomenex. The column was eluted with a linear gradient of 97 percent buffer A (100 mM triethylammonium acetate, pH 7) to 92 percent buffer A over a period of 12 minutes. The composition of buffer B is 80:20 acetonitrile:35 mM triethylammonium acetate. Detection was monitored by absorbance at 250, 260 and 280 nm. Under these conditions, dCTP was found to elute between 4 and 4.5 minutes, TTP and dGTP eluted as two peaks between 7 and 7.5 minutes, and DATP eluted from 9 to 9.5 minutes.

The fractions containing the free dNTPs were collected and lyophilized. Fraction one contained dCTP, fraction two contained dGTP and TTP, and fraction three contained DATP.

Each fraction was reconstituted in 100 µL of nanopure water. Ten microliters of each fraction, or 10 µL of water as a control, were added to a 10 µL mixture of water, 10×DNA Polymerase Buffer, and ADP so that the final concentration was 1×DNA pol buffer and 0.1 µM ADP. NDPK (0.005 units) was added to each tube in one set of the tubes and an equal amount of water was added to each tube in the other set of tubes. Samples and controls were incubated at 37° C. for 15 minutes, 10 µL added to 100 µL of L/L reagent and the light output was measured on a Turner® TD10/20 luminometer. The relative light units (rlu) results obtained are shown below:

| Sample | Trial 1 | Trial 2 | Trial 3 | Avg rlu |
|---|---|---|---|---|
| Matched hybrid with NDPK | | | | |
| Fraction 1 | 206.6 | 200.6 | 205.9 | 204.4 |
| Fraction 2 | 839.4 | 851.6 | 833.9 | 841.6 |
| Fraction 3 | 1149.0 | 1150.0 | 1169.0 | 1156 |
| Mismatched hybrid with NDPK | | | | |
| Fraction 1 | 101.8 | 97.0 | 98.9 | 99.9 |
| Fraction 2 | 386.1 | 387.3 | 382.2 | 385.2 |
| Fraction 3 | 412.4 | 409.9 | 416.5 | 412.9 |
| Match hybrid without NDPK | | | | |
| Fraction 1 | 6.8 | 6.5 | — | 6.6 |
| Fraction 2 | 10.9 | 11.5 | — | 11.2 |
| Fraction 3 | 33.0 | 37.8 | — | 35.4 |
| Mismatched hybrid without NDPK | | | | |
| Fraction 1 | 6.2 | 6.7 | — | 6.4 |
| Fraction 2 | 8.3 | 8.4 | — | 8.4 |
| Fraction 3 | 13.4 | 13.5 | — | 13.4 |
| No dNTP | 7.9 | 7.5 | — | 7.7 |

As is seen from the above data, the fraction one match:mismatch ratio is 2.1, fraction 2 match:mismatch ratio is 2.2 and fraction 3 match:mismatch ratio is 2.8. The data therefore demonstrate the utility of using HPLC separation of individual nucleotides followed by NDPK conversion to ATP, the preferred substrate of luciferase. Fraction 3 provides a slightly higher match:mismatch ratio owing to the presence of DATP in the nucleotide HPLC fraction. Nevertheless, HPLC separation of identifier nucleotides is useful in the interrogation assays of the present invention.

CV12
5'CCAACAGACGCTCCACGTTCTTTCT-GACGTATTCGTGCAGCATGGTCTGCGAG-CATTCGTGGTAGAAGCGAGCT 3' SEQ ID NO:37
CV15 5'CTACCACGAATGCTCGCAGAC 3' SEQ ID NO:38
CV16 5'CTACCACGAATGCTCGCAGAT 3' SEQ ID NO:39

EXAMPLE 6

Multiplex Determination of Nucleotide Sequences Associated with Factor V Leiden and with a Prothrombin SNP in the Same Reaction A assay is performed in this Example to determine if a human DNA sample contains the Leiden mutatuion of the Factor V gene, as well as a particular Prothrombin single nucleotide polymorphism (SNP). The assay for these two characteristics is performed simultaneously in the same reaction.

Probes PT5 (SEQ ID NO:40) and PT6 (SEQ ID NO:41) were used to PCR-amplify a region of human genomic DNA spanning about 500 base pairs encoding the prothrombin gene. Probes 10861 (SEQ ID NO:42) and 9828 (SEQ ID NO:43) were used to PCR amplify a region of human genomic DNA spanning about 300 base pairs encoding the Factor V gene. Probes PT5 and 10861 have phosphorothioate linkages between the first five bases at the 5' end.

The Factor V and Prothrombin fragments were co-amplified in one PCR reaction under the following conditions:

| | |
|---|---|
| 5 µL | 10X PCR buffer |
| 5 µL | 25 mM MgCl$_2$ |
| 1 µL | 10 mM dNTPs |
| 1 µL | probe PT5 (50 pmol) |
| 1 µL | probe PT6 (50 pmol) |
| 1 µL | probe 10861 (50 pmol) |
| 1 µL | probe 9828 (50 pmol) |
| 1 µL | Human genomic DNA (40 ng) |
| 36 µL | water |
| 1.25 U | Taq |

The PCR cycling parameters were as follows: 94° C., 2 minutes; (94° C., 30 seconds; 60° C., 1 minutes; 70° C., 1 minutes)×40; 70° C., 5 minutes. Fifty units of T7 gene 6 Exonuclease (USB Amersham) were added to 25 µL of the PCR reaction and the solution was incubated for 30 minutes at 37° C. Magnetic silica (Promega, A1330) was used to remove free nucleotides from the solution and the remaining DNA was eluted with 100 µL of water.

The Prothrombin interrogation probes used are 11265 (SEQ ID NO:44) that matches mutant prothrombin sequence and 11266 (SEQ ID NO:45) that matches wild type prothrombin sequence. Each of those probes has a destabilizing mutation eight bases from the 3' end. The Factor V interrogation probes used are 9919 (SEQ ID NO:46) that matches wild types Factor V sequence and 11432 (SEQ ID NO:47) that matches Factor V Leiden mutation sequence.

Four microliters of the eluted DNA were interrogated with each interrogation probe independently and also with the Factor V and Prothrombin mutant probes conjointly in one reaction. The interrogation reactions were assembled as follows.

| | |
|---|---|
| 4 µL | DNA (PCR product, Exo6 treated and purified |
| 150 pmol | each interrogation oligo |
| water | added to a final volume of 20 µL |

The reactions were incubated at 95° C. for 3 minutes and then at 37° C. for 10 minutes. Twenty microliters of the standard master mix was then added and the reaction incubated at 37° C. for 15 minutes. One hundred microliters of the L/L reagent were then added and the light output measured in a Turner® TD20/20 luminometer. The master mix contains the following.

| | |
|---|---|
| 71 µL | water |
| 20 µL | 10X DNA pol buffer |
| 5 µL | 40 mM NaPPi |
| 2 µL | 10 µM ADP |
| 1 µL | 1 unit/µL NDPK |
| 1 | 10 unit/µL Klenow exo- |

The light output was as follows.

| Interrogation oligo | Genomic DNA 1 | Genomic DNA 2 |
|---|---|---|
| 9919 (FV wt) | 431 | 424 |
| 11432 (FV mut) | 45 | 57 |
| 11266 (Pt wt) | 902 | 878 |
| 11265 (Pt mut) | 145 | 161 |
| 11432 + 11265 | 77 | 98 |
| no oligo | 44 | 57 |

These data indicate that the both genomic DNAs are from individuals wild type for Factor V and for wild type Prothrombin.

An additional 96 clinical genomic DNA samples were interrogated as described above. All the data fit into the following equation for calling the genotype.

rlu both wild type probes/rlu both wild type+rlu both mutant probes>0.75

This equation is the analytical output from the interrogation including both wild type probes divided by the analytical output from both wild type probes added to the analytical output from both mutant probes. If that value is greater than 0.75 then the sample is homozygous wild type at both loci. If that value is less than 0.75 then there is good likelihood that at least one allele at least one of the loci is mutant and the sample should be further analyzed for the genotype at each locus separately.

PT5 5' ATAGCACTGGGAGCATTGAGGC 3' SEQ ID NO:40
PT6 5' GCACAGACGGCTGTTCTCTT 3' SEQ ID NO:41
10861 5' TGCCCAGTGCTTAACAAGACCA 3' SEQ ID NO:42
9828 5' TGTTATCACACTGGTGCTAA 3' SEQ ID NO:43
11265 5' GTGATTCTCAGCA 3' SEQ ID NO:44
11266 5' GTGATTCTCAGCG 3' SEQ ID NO:45
9919 5' GACAAAATACCTGTATTCCTCG 3' SEQ ID NO:46
11432 5' GACAAAATACCTGTATTCCTTG 3' SEQ ID NO:47

EXAMPLE 7

Multiplex Interrogation for Factor V Leiden and Prothrombin Mutation:

Mass Spectroscopy Analysis

This Example demonstrates that nucleotides released from the 3'-terminus of a hybridized probe in a multiplex reaction by a process of the invention can be detected by mass spectroscopy and thereby determine whether a mutant allele exists at one of the loci being studied.

Probes PT5 (SEQ ID NO:40) and PT6 (SEQ ID NO:41) are used to PCR-amplify a region of human genomic DNA spanning about 500 base pairs encoding the prothrombin gene. Probes 10861 (SEQ ID NO:42) and 9828 (SEQ ID NO:43) are used to PCR amplify a region of human genomic DNA spanning about 300 base pairs encoding the Factor V gene. These probes and the PCR reaction conditions are detailed in Example 6. Probes PT5 and 10861 have phosphorothioate linkages between the first five bases at the 5' end. The PCR product is treated with T7 gene 6 Exonuclease (USB Amersham) and separated from free nucleotides as described in Example 6.

The prothrombin interrogation probe, 11265 (SEQ ID NO:44), is totally complementary to a segment of the mutant prothrombin sequence. The Factor V interrogation probe, 11432 (SEQ ID NO:47), is totally complementary to a segment of the mutant Factor V Leiden mutation sequence. Each of these probes has a destabilizing mutation eight bases from the 3'-end.

The PCR products are synthesized, Exo 6 treated, and purified as described in Example 6. The interrogation reactions are assembled with 40 μL of each PCR product and 1.5 nmol of each interrogation probe. Water is added to a final volume of 100 μL. These reactions are assembled in duplicate so that one can be assayed with Klenow exo- polymerase and yeast NDPK at 37° C., while the other is assayed with The triple mutant polymerase and Pfu NDPK at 70° C.

These assembled reactions are incubated at 95° C. for 3 minutes and then at 37° C. for 10 minutes. The assembled reactions may be lyophilized to decrease the volume. The two different master mixes are assembled. Both master mixes have 2 mM sodium pyrophosphate and 0.2 μM ADP. One with 1–2 U Klenow exo- and 0.2 U yeast NDPK, and 2×polymerase buffer (M195A); the other with 1 U Tne triple mutant polymerase and 0.1 U Pfu NDPK, 2×polymerase buffer (M1901), and 5 mM magnesium chloride. An equal volume of each master mix is separately added to the reaction solutions described above. Then the solution containing Klenow exo- as the polymerase is incubated at 37° C. for 15 minutes, while the solution containing Tne triple mutant polymerase is incubated at between 55° C. and 70° C.

The presence or absence of released nucleotides, converted to ATP, is analyzed for by silicon desorption ionization mass spectroscopy (Wei, J. et al. *Nature*. 399:243–246, 1999). This method is sensitive to femtomole and attomole levels of analyte. The samples are prepared as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomol to 100 picomol analyte) of solution are deposited onto the porous surfaces and allowed to dry before mass spectrometry analysis. These experiments are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyzer with a voltage of 20 kV. Other liquid chromatography-mass spectrometry (LC-MS) instrumentation may also be used for analysis (Niessen W. *J. Chromatogra* A 794: (407–435, 1998).

An observance of released nucleotide from either of the reactions containing the two mutant probe, at levels greater than background, indicates the presence of a at least one mutant prothrombin or Factor V Leiden allele in the genomic DNA sample assayed.

| 10861 | 5' TGCCCAGTGCTTAACAAGACCA 3' | SEQ ID NO:42 |
| 9828 | 5' TGTTATCACACTGGTGCTAA 3' | SEQ ID NO:43 |

-continued

| PT5 | 5' ATAGCACTGGGAGCATTGAGGC 3' | SEQ ID NO:40 |
| PT6 | 5' GCACAGACGGCTGTTCTCTT 3' | SEQ ID NO:41 |
| 11265 | 5' GTGATTCTCAGCA 3' | SEQ ID NO:44 |
| 11432 | 5' GACAAAATACCTGTATTCCTTG 3' | SEQ ID NO:47 |

EXAMPLE 8

Multiplex Interrogation using Fluorescent Labels

This example demonstrates that nucleotides released from the 3'-terminus of multiple probes, each hybridized to a target nucleic acid of interest, by a process of the invention can be detected by mass spectrometry or by fluorimetric HPLC and thereby provide evidence of the presence or absence of the target nucleic acid in a nucleic acid sample or of a specific base at an interrogation position of the target.

Each interrogation probe is designed to have a different fluorescent label attached to the 3'-terminal nucleotide in a manner such that the label does not interfere with the ability of the depolymerizing enzyme to remove the nucleotide from the probe. Such fluorescent tags, such as fluorescein or rhodamine, can be incorporated into the probe during synthesis with a fluorescent molecule attached to the phosphoramadite nucleotide with a linker of at least 6 carbons (Glen Research).

Probes PT5 (SEQ ID NO:40) and PT6 (SEQ ID NO:41) are used to PCR-amplify a region of human genomic DNA spanning about 500 base pairs encoding the prothrombin gene. Probes 10861 (SEQ ID NO:42) and 9828 (SEQ ID NO:43) are used to PCR amplify a region of human genomic DNA spannning about 300 base pairs encoding the Factor V gene. These probes and the PCR reaction conditions are detailed in Example 6. The PCR products are treated with T7 gene 6 Exonuclease (USB Amersham) and separated from free nucleotides as described in Example 6.

The prothrombin interrogation probes are 11265 (SEQ ID NO:44), that is totally complementary to a segment of the mutant prothrombin sequence, and 11266 (SEQ ID NO:45), that is totally complementary to a segment of the wild-type prothrombin sequence. Each of these probes has a destabilizing mutation eight bases from the 3'-end. Also, each of these probes is synthesized with a fluorescent nucleotide analog at the 3'-terminal nucleotide position. The prothrombin probes are tagged with fluorescein; the factor V probes are tagged with rhodamine.

The purified PCR products are interrogated in separate reactions with either both wild-type probes or both mutant probes. Interrogation reactions are assembled as follows:
40 μL each of the two PCR products
1.5 nmol each of the wild type or each of the mutant labeled interrogation oligos
water is added to a final volume of 100 μL.

The reactions are incubated at 95° C. for 3 minutes and then at 37° C. for 15 minutes. The reactions are then lyophilized to a final volume of 20 μL.

Twenty microliters of master mix are then added. The composition of the master mix containing Klenow exo- is described in Example 4 with the exception that there is no ADP and no NDPK. The reaction then proceeds at 37° C. for 15 minutes.

The solutions are then split in half and analyzed using two different methods. In one method, the presence or absence of released nucleotides in the solutions is analyzed by silicon desorption ionization mass spectroscopy (Wei, J. et al.

Nature. 399:243–246, 1999). This method is sensitive to femtomole and attomole levels of analyte. The samples are prepared for spectrometry as described in that paper. Essentially, analytes are dissolved in a deionized water/methanol mixture (1:1) at concentrations typically ranging from 0.001 to 10.0 μM. Aliquots (at least 0.5 to 1.0 μL, corresponding to at least 0.5 femtomol to 100 picomol analyte) of solution are deposited onto the porous surfaces and permitted to dry before mass spectrometry analysis.

These studies are performed on a Voyager DE-STR, time-of-flight mass spectrometer (PerSeptive Biosystems) using a pulsed nitrogen laser (Laser Science) operated at 337 nm. Once formed, ions are accelerated into the time-of-flight mass analyser with a voltage of 20 kV. Other liquid chromatography-mass spectrometry (LC-MS) instrumentation may be used for analysis (Niessen W. *J. Chromatogra A* 794:407–435, 1998)

In a second method, the presence or absence of released nucleotides in the solutions is analyzed by HPLC using a fluorescence detector as described in Jain, et al. *Biochem Biophys Res Commun* 200:1239–1244, 1994 or Levitt, B. et al. Anal Biochem 137:93–100, 1984.

An observance of released nucleotide from the reactions containing the mutant probes, at levels greater than background (control reactions that contain no enzyme), is indicative of the presence of at least one mutant prothrombin or Factor V Leiden allele in the genomic DNA sample assayed. An observance of released nucleotide from the reaction containing the wild-type probes, at levels greater than background, is indicative of the presence of at least one wild-type prothrombin or Factor V allele in the genomic DNA sample assayed.

| PT5 | 5' ATAGCACTGGGAGCATTGAGGC 3' | SEQ ID NO:40 |
| PT6 | 5' GCACAGACGGCTGTTCTCTT 3' | SEQ ID NO:41 |
| 10861 | 5' TGCCCAGTGCTTAACAAGACCA 3' | SEQ ID NO:42 |
| 9828 | 5' TGTTATCACACTGGTGCTAA 3' | SEQ ID NO:43 |

86:6196–6200). These PCR primers were diluted in 10 mM Tris, pH 7.5, to a final concentration of 0.22 μg/μL. The genomic DNAs used were bovine (Clontech, 6850-1), chicken (Clontech, 6852-1), dog (Clontech, 6950-1) and human (Promega, G1521).

The PCR reactions were assembled to include 5 μL 10×buffer with 15 mM MgCl$_2$ (Promega, M188J), 1 μL dNTPs 10 mM (Promega, C144G), 2 μL primer 11590, 2 μL primer 11589, 0.5 μL Taq polymerase 5 U/μL (Promega, M186E), and 38.5 μL water. To each tube was then added 1 μL (100 ng) of genomic DNA. The PCR cycling parameters were (15 seconds, 94° C.; 15 seconds, 55° C.; 30 seconds, 72° C.)×30. The size of PCR products was confirmed by running an aliquot on an agarose gel and visualizing with ethidium bromide (EtBr) staining. The PCR products were then separated from free nucleotides (Promega, A7170) and an aliquot run on an agarose gel. All samples produced a PCR product of the same size.

Each PCR DNA was then used in an assay to determine if it could be specifically identified with a species-specific probe. One microliter of interrogation probe (1 g/μL) and 17 μL water were combined with 2 μL of the appropriate PCR product and heated at 91° C. for 3 minutes, then cooled at room temperature for 15 minutes. Twenty microliters of master mix (described below) were added to each tube and each was further incubated at 37° C. for 15 minutes. Four microliters of the solutions were then added to 100 μL L/L reagent (Promega F120B), and the relative light output (rlu) measured on a Turner® TD20/20 luminometer. The rlu average values from two reactions, minus the DNA background values, along with the standard deviation values are listed below.

Master mix:

| 312 μL | 10X DNA pol buffer (Promega M195A) |
| 39 μL | NaPPi 40 mM (Promega E350B) |
| 39 μL | Klenow exo minus (Promega M128B) |
| 15.6 μL | NDPK 1 U/μL |
| 31.2 μL | ADP 10 μM (Sigma) |
| 1123 μL | water (Promega AA399) |

Averages from 2 reactions. Net light units are calculated by subtracting the DNA background

| | | | | | | Standard Deviations | | | | |
|---|---|---|---|---|---|---|---|---|---|---|
| Probe | No DNA | Human DNA | Chicken DNA | Cow DNA | Dog DNA | No DNA | Human DNA | Chicken DNA | Cow DNA | Dog DNA |
| comzoo | −0.096 | 44.5 | 14.25 | 119.7 | 124.6 | 0.654 | 7.000 | 23.33 | 3.465 | 8.63 |
| huzoo1 | 1.771 | 38 | −40 | −51.85 | −63.55 | 0.137 | 38.96 | 31.74 | 6.505 | 12.52 |
| huzoo2 | −0.889 | 101.6 | −23.35 | −0.05 | −48.75 | 0.761 | 3.959 | 0.141 | 8.768 | 2.19 |
| chzoo1 | 43.07 | −30.4 | 34.05 | −2.75 | −31.15 | 7.078 | 1.909 | 6.364 | 2.687 | 8.70 |
| chzoo2 | −0.361 | 57.6 | 50.7 | 33.05 | −3.25 | 0.075 | 43.77 | 29.34 | 12.59 | 21.43 |
| cozoo2 | 1.925 | 90.95 | 125.1 | 202.6 | 132.5 | 0.208 | 20.08 | 13.22 | 8.627 | 19.30 |
| dozoo2 | 0.966 | | | 71.8 | 158.7 | 0.180 | | | 9.546 | 1.98 |

EXAMPLE 9

Speciation—Detection of Mitochondrial DNA Specific to Various Animals

In this example, a segment of mitochondrial DNA comprising a segment of the cytochrome B gene was amplified from a variety of animal species using PCR primers 11590 (SEQ ID NO:48) and 11589 (SEQ ID NO:49) (PNAS The data demonstrate that the primers detect the mitochondrial PCR product. Both of the human-specific probes (11576 (SEQ ID NO:50) and 11583 (SEQ ID NO:51) were shown to be specific for human mitochondrial DNA. The common probe, 11582 (SEQ ID NO:52), detected all of the species, but was less efficient with chicken DNA. The chicken-specific probe, 11577 (SEQ ID NO:53), was specific for chicken mitochondrial DNA, but the other chicken-specific prove, 11584 (SEQ ID NO:54), detected all the species except dog. The cow-specific probe, 11588 (SEQ ID NO:55) gave the best detection signal for cow DNA, but also detected the other species. The dog-specific probe, 11586 (SEQ ID NO:56), was assayed only with dog and cow DNA, but detected the dog DNA better than cow DNA. A cleaner PCR product provides DNA with less background.

11590 zooamp2
5' AAACTGCAGCCCCTCAGAATGATATTTGTCCTCA 3' SEQ ID NO:48

11589 zooamp1
5' AAAAAGCTTCCATCCAACATCTCAGCAT-GATGAAA 3' SEQ ID NO:49

| 11576 | huzoo1 | 5' CCAGACGCCTCA 3' | SEQ ID NO:50 |
| 11583 | huzoo2 | 5' ACCTTCACGCCA 3' | SEQ ID NO:51 |
| 11582 | comzoo | 5' TGCCGAGACGT 3' | SEQ ID NO:52 |
| 11577 | chzoo1 | 5' GCAGACACATCC 3' | SEQ ID NO:53 |
| 11584 | chzoo2 | 5' GGAATCTCCACG 3' | SEQ ID NO:54 |
| 11588 | cozoo2 | 5' ACATACACGCAA 3' | SEQ ID NO:55 |
| 11586 | dozoo2 | 5' ATATGCACGCAA 3' | SEQ ID NO:56 |

EXAMPLE 10

Self-annealing Interrogation Probe

This Example illustrates use of a different type of oligonucleotide probe that is used to form a hairpin structure in the interrogation technology of this invention. This study demonstrates a method for eliminating the need for adding a probe specific to the interrogation site to the interrogation reaction.

Here, the oligonucleotide probe anneals to the target strand downstream of (3' to) the interrogation position in the target strand. The oligonucleotide has at its 5' end an unannealed region of nucleotides followed by about 5 to about 20 nucleotides that are identical to the interrogation region on the target strand. The annealed 3' end of the oligonucleotide is then extended through the interrogation position of the target strand creating what is referred to as extended probe. The hybrid is denatured and a hairpin structure formed between the extended probe strand and the 5' end of the oligonucleotide probe. This region is then assayed in a standard interrogation reaction to determine if a mismatch is present or not.

Four probes were designed to represent different types of hairpin formations that an extended probe strands may assume. These probes are 10207 (SEQ ID NO:57), 10208 (SEQ ID NO:58), 10209 (SEQ ID NO:59), and 10212 (SEQ ID NO:60).

These probes are predicted to form the following self-hybridized secondary structures when allowed to self-anneal:

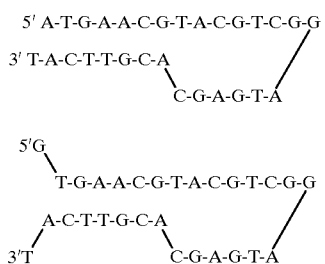

10207

10208

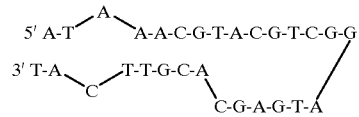

10209

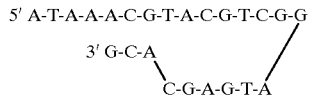

10212

A 5 μL (5 μg) aliquot of each of the four probes was diluted to 100 μL with nanopure water. They were then sequentially diluted 1:10 to a final dilution factor of 1:100,000. Twenty microliters of the diluted probes were heated, in separate tubes, at 95° C. for 3 minutes and cooled to room temperature for 10 minutes to permit self-annealing. The following master mix was assembled and mixed.

| Component | Amount |
| --- | --- |
| 10X DNA Pol Buffer (Promega, M195A) | 200 μL |
| Klenow exo- (1 U/μL) (Promega M218B) | 12.5 μL |
| 40 mM Sodium Pyrophosphate (Promega C350B) | 25 μL |
| NDPK (1 U/μL) | 10 μL |
| 10 μM ADP (Sigma A5285) | 20 μL |
| Water | 732.5 μL |

Twenty microliters of the above Master Mix, were then added to each tube and the tubes were incubated at 37° C. for 15 minutes. Ten microliters of the solutions were added to 100 μL of L/L reagent (Promega, F202A) and relative light units measured immediately with a Turner® TD20/20 luminometer. The no-probe control resulted in 57.24 relative light units and the remaining probe results are reported below in relative light units (rlu).

| Log dilution | Probe | | | |
| --- | --- | --- | --- | --- |
| | 10207 | 10208 | 10209 | 10212 |
| −5 | 44.89 | 56.22 | 57.57 | 57.80 |
| −4 | 85.21 | 64.56 | 58.26 | 63.15 |
| −3 | 297.7 | 70.53 | 79.12 | 82.65 |
| −2 | 970.5 | 108.4 | 80.06 | 106.7 |

Probe 10207 worked as an efficient target for interrogation as expected, with probe 10208 providing the anticipated negative results. Probe 10212 has only a three base match so it may be un-extended, thus resulting in the low values. Probe 10209 likely has the 3' terminal nucleotide unannealed when the hairpin forms due to the mismatch at the third nucleotide in from the 3' end. Such an unannealed 3' terminal nucleotide would account for the low rlu values.

10207 5' ATGAACGTACGTCGGATGAGCACGTTCAT 3' SEQ ID NO:57

10208 5' GTGAACGTACGTCGGATGAGCACGTTCAT 3' SEQ ID NO:58

10209 5' ATAAACGTACGTCGGATGAGCACGTTCAT 3' SEQ ID NO:59

10212 5' ATAAACGTACGTCGGATGAGCACG 3' NO:60

EXAMPLE 11

Interrogation with a Self-Annealing Primer II

This example and FIG. 2 illustrate use of a different type of oligonucleotide probe, a "REAPER™" probe in a process of this invention. This example demonstrates a method for eliminating the need for adding a probe specific to the interrogation site to the interrogation reaction.

Here, the oligonucleotide first probe (SEQ ID NO:62), at its 3'-end, anneals to the target strand (SEQ ID NO:61) at a position downstream of (3' to) the interrogation position in the target strand (FIG. 2A). The probe has at its 5'-end an unannealed region of nucleotides including about 5 to about 20 nucleotides that are identical to a region on the target strand including the interrogation position. This region of identity is present in the same orientation on both the target and the probe strands.

The annealed 3'-end of the probe is then extended through the interrogation position of the target strand forming what is referred to as a first extended probe and an extended first hybrid as is illustrated in FIG. 2B (SEQ ID NO:63). The extended first hybrid is denatured and a second probe (SEQ ID NO:64) is annealed to the first extended probe to form a second hybrid. This second probe is complementary to the first extended probe strand at a region downstream of the interrogation position on the first extended probe strand (FIG. 2C).

The second probe is then extended and a second extended hybrid is formed as illustrated in FIG. 2D. The second extended hybrid is comprised of the first extended probe and second extended probe (SEQ ID NO:65).

The strands of the second extended hybrid are denatured and permitted to renature to form a hairpin structure. Upon hairpin formation, the first extended probe forms a hairpin structure that has a 3'-overhang, whereas the second extended probe forms a hairpin structure that contains a 5'-overhang that provides a substrate for depolymerization. The second extended probe strand is then depolymerized and the analytical output obtained as described elsewhere herein. The analytical output determines the presence or absence of the original target strand or of a particular base in the original target strand as is also discussed elsewhere herein.

SEQ ID NO:61 oligonucleotide is diluted to 1 mg/mL in water. This solution is labeled 286. SEQ ID NO:62 oligonucleotide is diluted to 1 mg/mL in water and this solution is labeled 287. One microliter of each solution 286 and 287 is combined with 18 μL water. The solution is heated to 95° C. for 5 minutes then is cooled at room temperature for 10 minutes to permit oligonucleotides of SEQ ID NOs:61 and 62 to anneal.

To this solution are added dNTP mixture to a final concentration of 0.25 mM for each dNTP, 10×Klenow buffer to a final concentration of 1×, and 5 U of Klenow enzyme. The tube with these components is incubated at 37° C. for 30 minutes. The extended first hybrid DNA so formed (containing SEQ ID NO:63) is purified (Qiagen, Mermaid system) and eluted into 50 μl of water.

To this solution of the purified extended first hybrid is added 1 μl SEQ ID NO:64 oligonucleotide (1 mg/mL) as second probe. The solution is then heated to 95° C. for 5 minutes and is cooled at room temperature to permit 289 and 288 to anneal as illustrated in FIG. 2C to form the second hybrid. To this solution are added a DNTP mixture to a final concentration of 0.25 mM for each DNTP, 10×Klenow buffer to a final concentration of 1×, and 5 U of Klenow enzyme. The tube with these components is incubated at 37° C. for 30 minutes to form a second extended hybrid that contains a second extended probe (oligonucleotide SEQ ID NO:65).

The SEQ ID NO:65/63 second extended hybrid DNA (FIG. 2D) formed is purified (Qiagen, Mermaid system) to separate the extended hybrid from the unreacted dNTPs and eluted into 50 μl water. (Alternatively, the original 287 oligo is biotinylated at it's 5-end and this biotin is then also present in strand of SEQ ID NO:63. This biotinylated strand 288 is then denatured from strand 290 and removed from the solution with streptavidin coated paramagnetic particles according to the manufacturer's instructions (Promega, Z5481) and the 290 hairpin structure is allowed to form as below).

This hybrid solution is then heated to 95C for 5 minutes diluted to 100 μl with water and is cooled on ice for 10 minutes to permit hairpin structure formation.

A master mix is assembled and mixed according to the following table.

| Component | Amount |
| --- | --- |
| 10X DNA Pol Buffer (Promega, M195A) | 200 μL |
| Klenow exo- (1 U/μL) (Promega M218B) | 12.5 μL |
| 40 mM Sodium Pyrophosphate (Promega C350B) | 25 μL |
| NDPK (1 U/μL) | 10 μL |
| 10 uM ADP (Sigma A5285) | 20 μL |
| Water | 732.5 μL |

Twenty microliters of this master mix are added to 20 μL of the above hairpin-containing solutions after cooling, and the resulting mixtures are heated at 37° C. for 15 minutes. After this incubation, duplicate 4 μL samples of the solution are removed, added to 100 μL of L/L Reagent (Promega, F202A) and the light produced by the reaction is measured immediately using a Turner ® TD20/20 luminometer. A positive analytical output at levels over background (no enzyme) indicates that a matched base was present at the 3'-terminus of the hairpin structure and this further indicates the presence of the target strand, and for this particular example, it also indicates the presence of a G base at the interrogation position of the target.

5'CCCGGAGAGACCTCCTTAAGGGGC-CATATTATTTCGTCGATTCCAGTGTTG-GCCAAACGGAT 3' SEQ ID NO:61

5' GGGGCCATATTATTTCGCCGTTTGGC-CAACACTGGAATCGA 3' SEQ ID NO:62

5' GGGGCCATATTATTTCGCCGTTTGGC-CAACACTGGAATCGACGAAATAATATG-GCCCCTTAAGGAGGTCTCTCCGGG 3' SEQ ID NO:63

5'CCCGGAGAGACCTCCT 3' SEQ ID NO:64

5'CCCGGAGAGACCTCCTTAAGGGGC-CATATTATTTCGTCGATTCCAGTGTTG-GCCAAACGGCGAAATAATATGGCCCC 3' SEQ ID NO:65

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for determining the presence or absence of a plurality of predetermined nucleic acid target sequences in a nucleic acid sample that comprises the steps of:
   (A) providing a treated sample that may contain said plurality of predetermined nucleic acid target sequences hybridized with their respective nucleic acid probes, said probes each including an identifier nucleotide in the 3'-terminal region;
   (B) admixing the treated sample with a depolymerizing amount of an enzyme whose activity is to release one or more nucleotides from the 3'-terminus of a hybridized nucleic acid probe to form a treated reaction mixture, wherein said enzyme catalyzes (i) pyrophosphorolysis;
   (C) maintaining the treated reaction mixture for a time period sufficient to permit the enzyme to depolymerize hybridized nucleic acid and release identifier nucleotides therefrom; and
   (D) analyzing for the presence of released identifier nucleotides to obtain an analytical output, the analytical output indicating the presence or absence of said nucleic acid target sequences.

2. The method according to claim 1 wherein said analytical output is obtained by luminescence spectroscopy.

3. The method according to claim 1 wherein said analytical output is obtained by fluorescence spectroscopy.

4. The method according to claim 1 wherein said analytical output is obtained by mass spectrometry.

5. The method according to claim 1 wherein said analytical output is obtained by absorbance spectroscopy.

6. The method according to claim 1 wherein said predetermined nucleic acid target sequences are associated with blood coagulation.

7. The method according to claim 6 wherein said nucleic acid probes comprise a plurality of the following sequences:
   5' CTGCTGCCCTCTGTATTCCTCG 3' SEQ ID NO:14;
   5' CTGCTGCCCTCTGTATTCCTTG 3' SEQ ID NO:15;
   5' GTGACTCTCAGCG 3' SEQ ID NO:87;
   5' GTGACTCTCAGCA 3' SEQ ID NO:88;
   5' GTGATTCTCAGCG 3' SEQ ID NO:89;
   5' GTGATTCTCAGCA 3' SEQ ID NO:90;
   5' GACAAAATACCTGTATTCCTCG 3' SEQ ID NO:91;
   5' GACAAAATACCTGTATTCCTTG 3' SEQ ID NO:92;
   5' GGAGCATTGAGGCTCG 3' SEQ ID NO:93;
   5' GGAGCATTGAGGCTTG 3' SEQ ID NO:94;
   5' GACAAAATACCTGTATTCCTTG 3' SEQ ID NO:47;
   5' GTGATTCTCAGCA 3' SEQ ID NO:44;
   5' GTGATTCTCAGCG 3' SEQ ID NO:45; and
   5' GACAAAATACCTGTATTCCTCG 3' SEQ ID NO:46.

8. The method according to claim 1 wherein said predetermined nucleic acid target sequences are useful for speciation.

9. The method according to claim 8 wherein said nucleic acid probes comprise a plurality of the following sequences:
   5' CCAGACGCCTCA 3' SEQ ID NO:50;
   5' ACCTTCACGCCA 3' SEQ ID NO:51;
   5' TGCCGAGACGT 3' SEQ ID NO:52;
   5' GCAGACACATCC 3' SEQ ID NO:53;
   5' GGAATCTCCACG 3' SEQ ID NO:54;
   5' ACATACACGCAA 3' SEQ ID NO:55; and
   5' ATATGCACGCAA 3' SEQ ID NO:56.

10. The method according to claim 1 wherein said predetermined nucleic acid target sequences are associated with congenital adrenal hyperplasia.

11. The method according to claim 10 wherein said nucleic acid probes comprise a plurality of the following sequences:
   5' CGGAGCCTCCACCTCCCG SEQ ID NO:23;
   5' CACCCTCCAGCCCCCAGC 3' SEQ ID NO:24;
   5' CGGAGCCTCCACCTCCTG 3' SEQ ID NO:25;
   5' CCTCACCTGCAGCATCAAC 3' SEQ ID NO:26;
   5' CACCCTCCAGCCCCCAAC 3' SEQ ID NO:27;
   5' CCTCACCTGCAGCATCATC 3' SEQ ID NO:28;
   5' CCTGGAAGGGCACTT 3' SEQ ID NO:29;
   5' CCTGGAAGGGCACGT 3' SEQ ID NO:30;
   5' GATTCAGCAGCGACTGTA 3' SEQ ID NO:31;
   5' GATTCAGCAGCGACTGCA 3' SEQ ID NO:32;
   5' CGAGGTGCTGCGCCTGCG 3' SEQ ID NO:33;
   5' CGAGGTGCTGCGCCTGTG 3' SEQ ID NO:34;
   5' GGGATCACATCGTGGAGATG 3' SEQ ID NO:35; and
   5' GGGATCACAACGAGGAGAAG 3' SEQ ID NO:36.

12. The method according to claim 1 including the further steps of forming said treated sample by
   (a) admixing a sample to be assayed with a plurality of nucleic acid probes to form a hybridization composition, wherein the 3'-terminal region of each of said nucleic acid probes (i) hybridize with partial or total complementarity to said nucleic acid target sequence when that sequence is present in the sample and (ii) include an identifier nucleotide;

(b) maintaining said hybridization composition for a time period sufficient to form a treated sample that may contain said predetermined nucleic acid target sequences hybridized with their respective nucleic acid probes.

13. The method according to claim 1 wherein nucleic acid sample is obtained from a biological sample.

14. The method according to claim 13 wherein a predetermined nucleic acid target sequence is a microbial or viral nucleic acid.

15. A method for determining the presence or absence of a plurality of predetermined nucleic acid target sequences in a nucleic acid sample that comprises the steps of:
(A) admixing a sample to be assayed with a plurality of nucleic acid probes to form a hybridization composition, wherein the 3'-terminal region of each of said nucleic acid probes (i) hybridizes with partial or total complementarity to at least one said predetermined nucleic acid target sequence when that sequence is present in the sample and (ii) includes an identifier nucleotide;
(B) maintaining said hybridization composition for a time period sufficient to form a treated sample that may contain said predetermined nucleic acid target sequence hybridized with a nucleic acid probe;
(C) admixing the treated sample with a depolymerizing amount of an enzyme whose activity is to release one or more nucleotides from the 3'-terminus of a hybridized nucleic acid probe to form a treated reaction mixture, wherein said enzyme catalyzes (i) pyrophosphorolysis;
(D) maintaining the treated reaction mixture for a time period sufficient to permit the enzyme to depolymerize hybridized nucleic acid and release identifier nucleotides therefrom; and
(E) analyzing for the presence of released identifier nucleotides to obtain an analytical output, the analytical output indicating the presence or absence of at least one of said plurality of nucleic acid target sequences.

16. The method according to claim 15 wherein said analytical output is obtained by luminescence spectroscopy.

17. The method according to claim 15 wherein said analytical output is obtained by fluorescence spectroscopy.

18. The method according to claim 15 wherein said analytical output is obtained by mass spectroscopy.

19. The method according to claim 15 wherein said analytical output is obtained by absorbance spectroscopy.

20. The method according to claim 15 wherein the analytical output obtained when one of said nucleic acid probes hybridizes with partial complementarity to one target nucleic acid sequence is greater than the analytical output when all of the nucleic acid probes hybridize with total complementarity to their respective nucleic acid target sequences.

21. The method according to claim 15 wherein the analytical output obtained when one of said nucleic acid probes hybridizes with partial complementarity to one target nucleic acid sequence is less than the analytical output when all of the nucleic acid probes hybridize with total complementarity to their respective nucleic acid target sequences.

22. The method according to claim 15 wherein the analytical output obtained when one of said nucleic acid probes hybridizes with total complementarity to one nucleic acid target sequence is greater than the analytical output when all of the nucleic acid probes hybridize with partial complementarity to their respective nucleic acid target sequences.

23. The method according to claim 15 wherein the analytical output obtained when one of said nucleic acid probes hybridize with total complementarity to one target nucleic acid sequence is less than the analytical output when all of the nucleic acid probes hybridize with partial complementarity to their respective nucleic acid target sequences.

24. The method according to claim 15 wherein said enzyme whose activity is to release nucleotides is a template-dependent polymerase that, in the presence of pyrophosphate ions, depolymerizes hybridized nucleic acids whose bases in the 3'-terminal region are matched with total complementarity.

25. The method according to claim 15 wherein said enzyme whose activity is to release nucleotides exhibits a 3'→5'-exonuclease activity, depolymerizing hybridized nucleic acids having one or more mismatched bases in the 3'-terminal region of the hybridized probe.

26. The method according to claim 15 wherein said nucleic acid probes comprise sequences complementary to nucleic acid sequences associated with blood coagulation.

27. The method according to claim 26 wherein said nucleic acid sequences associated with blood coagulation comprise
(a) a sequence of at least ten nucleotides of the Factor V Leiden mutation; and
(b) a sequence of at least ten nucleotides of prothrombin.

28. The method according to claim 27 wherein said nucleic acid sequences associated with blood coagulation is selected from the group consisting of SEQ ID NO:14, SEQ ID NO:15, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:47, SEQ ID NO:44, SEQ ID NO:45 and SEQ ID NO:46.

29. The method according to claim 15 wherein said nucleic acid probes comprise sequences complementary to nucleic acid sequences associated with cystic fibrosis.

30. The method according to claim 29 wherein said nucleic acid probes comprise sequences complementary to nucleic acid sequences associated with the cystic fibrosis delta F508 mutation.

31. The method according to claim 29 wherein said nucleic acid probes are SEQ ID NO:95 or SEQ ID NO:96.

32. A method for determining the presence or absence of a specific base in a nucleic acid target sequence in a sample to be assayed that comprises the steps of:
(A) admixing a sample to be assayed with a plurality of nucleic acid probes to form a hybridization composition, wherein the 3'-terminal region of at least one of said nucleic acid probes (i) is substantially complementary to said nucleic acid target sequence and comprises at least one predetermined nucleotide at an interrogation position, and (ii) includes an identifier nucleotide, and wherein said nucleic acid target sequence comprises at least one specific base whose presence or absence is to be determined;
(B) maintaining said hybridization composition for a time period sufficient to form a treated sample, wherein said interrogation position of the probe is a nucleotide that is aligned with said specific base to be identified in said target sequence, when present, so that base pairing can occur;
(C) admixing the treated sample with an enzyme whose activity is to release one or more nucleotides from the 3'-terminus of a hybridized nucleic acid probe to depolymerize the hybrid and form a treated reaction mixture, wherein said enzyme catalyzes (i) pyrophosphorolysis or;
(D) maintaining the treated reaction mixture for a time period sufficient to release an identifier nucleotide therefrom; and (E) analyzing for the presence or absence of released identifier nucleotide to obtain an analytical output that indicates the presence or absence of said specific base to be identified.

33. The method according to claim 32 wherein the identifier nucleotide is at the interrogation position.

34. The method according to claim 32 wherein said analytical output is obtained by luminescence spectroscopy.

35. The method according to claim 32 wherein said analytical output is obtained by fluorescence spectroscopy.

36. The method according to claim 32 wherein said analytical output is obtained by mass spectrometry.

37. The method according to claim 32 wherein said nucleic acid target sequence is selected from the group consisting of deoxyribonucleic acid and ribonucleic acid.

38. The method according to claim 37, further comprising a first probe, a second probe, a third probe and a fourth probe.

39. The method according to claim 38 wherein said interrogation position of said first probe comprises a nucleic acid residue that is a deoxyadenosine or adenosine residue, said interrogation position of said second probe comprises a nucleic acid residue that is a deoxythymidine or uridine residue, said interrogation position of said third probe comprises a nucleic acid residue that is a deoxyguanosine or guanosine residue, and said fourth nucleic acid probe comprises a nucleic acid residue that is a deoxycytosine or cytosine residue.

40. The method according to claim 32 wherein the analytical output obtained when one of said nucleic acid probes hybridizes with partial complementarity to one target nucleic acid sequence is greater than the analytical output when all of the nucleic acid probes hybridize with total complementarity to their respective nucleic acid target sequences.

41. The method according to claim 32 wherein the analytical output obtained when one of said nucleic acid probes hybridizes with partial complementarity to one target nucleic acid sequence is less than the analytical output when all of the nucleic acid probes hybridize with total complementarity to their respective nucleic acid target sequences.

42. The method according to claim 32 wherein the analytical output obtained when one of said nucleic acid probes hybridizes with total complementarity to one nucleic acid target sequence is greater than the analytical output when all of the nucleic acid probes hybridize with partial complementarity to their respective nucleic acid target sequences.

43. The method according to claim 32 wherein the analytical output obtained when one of said nucleic acid probes hybridize with total complementarity to one target nucleic acid sequence is less than the analytical output when all of the nucleic acid probes hybridize with partial complementarity to their respective nucleic acid target sequences.

44. The method according to claim 32 wherein said enzyme whose activity is to release nucleotides is a template-dependent polymerase that, in the presence of pyrophosphate ions, depolymerizes hybridized nucleic acid s whose bases in the 3' terminal region of the probe are matched with total complementarity.

45. The method according to claim 32 wherein said enzyme whose activity is to release nucleotides exhibits a 3' to 5' exonuclease activity, depolymerizing hybridized nucleic acids having one or more mismatched bases at the 3'-terminus of the hybridized probe.

46. A method for determining the presence or absence of a plurality of first nucleic acid targets in a nucleic acid sample containing those targets or a plurality of substantially identical second targets that comprises the steps of:

(A) admixing said sample to be assayed with one or more nucleic acid probes to form a hybridization composition, wherein said first and second nucleic acid targets comprise a region of sequence identity except for at least a single nucleotide at a predetermined position that differs between the targets, and wherein said nucleic acid probe (i) is substantially complementary to said nucleic acid target region of sequence identity and comprises at least one nucleotide at an interrogation position, said interrogation position of the probe being aligned with said predetermined position of a target when a target and probe are hybridized and (ii) includes an identifier nucleotide in the 3'-terminal region;

(B) maintaining said hybridization composition for a time period sufficient to form a treated sample wherein the nucleotide at said interrogation position of said probe is aligned with the nucleotide at said predetermined position of said target in said region of identity;

(C) admixing the treated sample with a depolymerizing amount an enzyme whose activity is to release one or more nucleotides from the 3'-terminus of a hybridized nucleic acid probe to form a treated reaction mixture, wherein said enzyme catalyzes (i) pyrophosphorolysis or;

(D) maintaining the treated reaction mixture for a time period sufficient to release identifier nucleotide and depolymerize said hybridized nucleic acid probe; and (E) analyzing for the presence of released identifier nucleotide to obtain an analytical output, said analytical output indicating the presence or absence of said nucleotide at said predetermined region and thereby the presence or absence of a first or second nucleic acid target.

47. The method according to claim 46 wherein said analytical output is obtained by fluorescence spectroscopy.

48. The method according to claim 46 wherein said analytical output is obtained by mass spectrometry.

49. The method according to claim 46 wherein said nucleic acid target sequence is selected from the group consisting of deoxyribonucleic acid and ribonucleic acid.

50. The method according to claim 46 wherein said first probe comprises a nucleotide at said interrogation position that is complementary to a first target nucleic acid at said predetermined position, and said second probe comprises a nucleotide at the interrogation position that is complementary to a second target nucleic acid at said predetermined position.

51. The method according to claim 46 wherein the analytical output obtained when one of said nucleic acid probes hybridizes with partial complementarity to one target nucleic acid sequence is greater than the analytical output when all of the nucleic acid probes hybridize with total complementarity to their respective nucleic acid target sequences.

52. The method according to claim 46 wherein the analytical output obtained when one of said nucleic acid probes hybridizes with partial complementarity to one target nucleic acid sequence is less than the analytical output when all of the nucleic acid probes hybridize with total complementarity to their respective nucleic acid target sequences.

53. The method according to claim 46 wherein the analytical output obtained when one of said nucleic acid probes hybridizes with total complementarity to one nucleic acid target sequence is greater than the analytical output when all of the nucleic acid probes hybridize with partial complementarity to their respective nucleic acid target sequences.

54. The method according to claim 46 wherein the analytical output obtained when one of said nucleic acid probes hybridizes with total complementarity to one target nucleic acid sequence is less than the analytical output when all of the nucleic acid probes hybridize with partial complementarity to their respective nucleic acid target sequences.

55. The method according to claim 46 wherein said enzyme whose activity is to release nucleotides is a template-dependent polymerase that, in the presence of pyrophosphate ions, depolymerizes hybridized nucleic acids whose bases in the 3'-terminal region are matched with total complementarity.

56. The method according to claim 46 wherein said enzyme whose activity is to release nucleotides exhibits a 3'→5'-exonuclease activity, depolymerizing hybridized nucleic acids having one or more mismatched bases in the 3'-terminal region of the hybridized probe.

57. A method for determining the presence or absence of a plurality of nucleic acid target sequences, each containing an interrogation position, in a nucleic acid sample that comprises the steps of:
  (A) providing a treated sample that contains a nucleic acid sample that may include said nucleic acid target sequences hybridized with their respective nucleic acid probes, each probe being comprised of three sections, (i) a first section that contains the probe 3'-terminal about 10 to about 30 nucleotides that are complementary to its nucleic acid target sequence at positions beginning about 1 to about 30 nucleic acids downstream of said interrogation position of the target sequence, (ii) a 5'-terminal region of about 10 to about 200 nucleic acids in length and having the identical sequence of said nucleic acid target sequence, and (iii) an optional third section that contains zero to about 50 nucleic acids that are not complementary to said nucleic acid sample;
  (B) extending said nucleic acid probes in a 3' direction to form second probes hybridized to the nucleic acid sample as second hybrids;
  (D) denaturing said second hybrids to separate said second probes from said nucleic acid target sequences;
  (E) renaturing said aqueous composition to form hairpin structures from said second probes;
  (F) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes (i) pyrophosphorolysis or;
  (G) maintaining the treated reaction mixture for a time period sufficient to permit the enzyme to depolymerize hybridized nucleic acid and release one or more nucleotides from the 3'-terminus therefrom; and
  (H) analyzing for the presence of released identifier nucleotide to obtain an analytical output, the analytical output indicating the presence or absence of said nucleic acid target sequences.

58. A method for determining the presence or absence of a plurality of nucleic acid target sequences, or a specific base within the target sequences, in a nucleic acid sample, that comprises the steps of:
  (A) providing a treated sample that contains a nucleic acid sample that may include a plurality of nucleic acid target sequences hybridized with their respective first nucleic acid probes as a first hybrid, said first probes each being comprised of at least two sections, a first section containing the probe 3'-terminal about 10 to about 30 nucleotides that are complementary to the target nucleic acid sequence at a position beginning about 5 to about 30 nucleotides downstream of the target interrogation position, a second section of the first probe containing about 5 to about 30 nucleotides that are a repeat of the target sequence from the interrogation position to about 10 to about 30 nucleotides downstream of the interrogation position that does not hybridize to said first section of the probe, and an optional third section of the probe located between the first and second sections of the probe that is zero to about 50 nucleotides in length and comprises a sequence that does not hybridize to either the first or second section of the probe;
  (B) extending the first hybrid in the treated sample at the 3'-end of the first probes, thereby extending the first probes past the interrogation position and forming an extended first hybrid that includes an interrogation position;
  (C) denaturing an aqueous composition of the extended first hybrid to separate the two nucleic acid strands and form an aqueous composition containing separated target nucleic acids and separated extended first probes;
  (D) annealing to each of the extended first probes second probes that are about 10 to about 30 nucleotides in length and are complementary to the extended first probes at a position beginning about 5 to about 2000 nucleotides downstream of the interrogation position in the extended first probes, thereby forming a second hybrid;
  (E) extending the second hybrid at the 3'-end of the second probes until that extension reaches the 5'-end of the extended first probes, thereby forming a second extended hybrid containing a second extended probe whose 3'-region includes an identifier nucleotide;
  (F) denaturing an aqueous composition of the extended second hybrid to separate the nucleic acid strands and form an aqueous composition containing separated extended first and second probes;
  (G) cooling the aqueous composition to form a hairpin structure from the separated extended second probes to form a hairpin structure-containing composition;
  (H) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes (i) pyrophosphorolysis or;
  (I) maintaining the reaction mixture for a time period sufficient to release 3'-terminal region identifier nucleotides; and
  (J) analyzing for the presence of released identifier nucleotide to obtain an analytical output, the analytical output indicating the presence or absence of said predetermined nucleic acid target sequence or a specific base within the target sequence.

59. The method according to claim 58 wherein said analytical output is obtained by luminescence spectroscopy.

60. The method according to claim 58 wherein said analytical output is obtained by fluorescence spectroscopy.

61. The method according to claim 58 wherein said analytical output is obtained by mass spectrometry.

62. The method according to claim 58 wherein said analytical output is obtained by absorbance spectroscopy.

63. A method for determining the presence or absence of a plurality of nucleic acid target sequences containing an interrogation position in a nucleic acid sample that comprises the steps of;
  (A) providing a treated sample that contains a nucleic acid sample that may include said plurality of nucleic acid target sequences, each hybridized with its respective nucleic acid probe that is comprised of three sections, (i) a first section that contains the probe 3'-terminal about 10 to about 30 nucleotides that are complementary to the nucleic acid target sequence at positions beginning about 1 to about 30 nucleic acids downstream of said interrogation position of the target sequence, (ii) a 5'-terminal region of about 10 to about 200 nucleic acids in length and having the identical sequence of said nucleic acid target sequence, and (iii) an optional third section that contains zero to about 50 nucleic acids that are not complementary to said nucleic acid sample, and;

(B) extending said nucleic acid probes in a 3' direction to form second probes hybridized to the nucleic acid sample as a second hybrid;

(D) denaturing said second hybrid to separate said second probes from said nucleic acid target sequences;

(E) renaturing said aqueous composition to form hairpin structures from said second probes;

(F) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes (i) pyrophosphorolysis or (ii);

(G) maintaining the treated reaction mixture for a time period sufficient to permit the enzyme to depolymerize hybridized nucleic acid and release one or more nucleotides from the 3'-terminus therefrom; and (H) analyzing for the presence of released identifier nucleotide to obtain an analytical output, the analytical output indicating the presence or absence of said nucleic acid target sequences.

64. The method according to claim 63 wherein said analytical output is obtained by luminescence spectroscopy.

65. The method according to claim 63 wherein said analytical output is obtained by fluorescence spectroscopy.

66. The method according to claim 63 wherein said analytical output is obtained by mass spectrometry.

67. The method according to claim 63 wherein said analytical output is obtained by absorbance spectroscopy.

68. The method according to claim 63 wherein the analytical output is distinguishable for the different nucleic acid target sequences.

69. A method for determining the presence or absence of a plurality of nucleic acid target sequences, or a specific base within a target sequence, in a nucleic acid sample, that comprises the steps of:

(A) providing a treated sample that contains a nucleic acid sample that may include a plurality of nucleic acid target sequences, each hybridized with its respective first nucleic acid probe as a first hybrid, said first probes being comprised of at least two sections, a first section containing the probe 3'-terminal about 10 to about 30 nucleotides that are complementary to the target nucleic acid sequence at a position beginning about 5 to about 30 nucleotides downstream of the target interrogation position, a second section of the first probe containing about 5 to about 30 nucleotides that are a repeat of the target sequence from the interrogation position to about 10 to about 30 nucleotides downstream of the interrogation position that does not hybridize to said first section of the probe, and an optional third section of the probe located between the first and second sections of the probe that is zero to about 50 nucleotides in length and comprises a sequence that does not hybridize to either the first or second section of the probe;

(B) extending the first hybrid in the treated sample at the 3'-end of the first probes, thereby extending the first probes past the interrogation position and forming an extended first hybrid that includes an interrogation position;

(C) denaturing an aqueous composition of the extended first hybrid to separate the two nucleic acid strands and form an aqueous composition containing separated target nucleic acids and a separated extended first probes;

(D) annealing to the extended first probes a second probe that is about 10 to about 30 nucleotides in length and is complementary to the extended first probe at a position beginning about 5 to about 2000 nucleotides downstream of the interrogation position in the extended first probes, thereby forming a second hybrid;

(E) extending the second hybrid at the 3'-end of the second probes until that extension reaches the 5'-end of the extended first probe, thereby forming a second extended hybrid containing a second extended probe whose 3'-region includes an identifier nucleotide;

(F) denaturing an aqueous composition of the extended second hybrid to separate the two nucleic acid strands and form an aqueous composition containing separated extended first and second probes;

(G) cooling the aqueous composition to form a hairpin structure from the separated extended second probe to form a hairpin structure-containing composition;

(H) admixing the hairpin structure-containing composition with a depolymerizing amount of an enzyme whose activity is to release one or more nucleotides from the 3'-terminus of a nucleic acid hybrid to form a treated reaction mixture, wherein said enzyme catalyzes (i) pyrophosphorolysis or (ii);

(I) maintaining the reaction mixture for a time period sufficient to release 3'-terminal region identifier nucleotides; and (J) analyzing for the presence of released identifier nucleotide to obtain an analytical output, the analytical output indicating the presence or absence of said predetermined nucleic acid target sequences or a specific base within a target sequence.

70. The method according to claim 69 wherein said analytical output is obtained by luminescence spectroscopy.

71. The method according to claim 69 wherein said analytical output is obtained by fluorescence spectroscopy.

72. The method according to claim 69 wherein said analytical output is obtained by mass spectrometry.

73. The method according to claim 69 wherein said analytical output is obtained by absorbance spectroscopy.

74. The method according to claim 69 wherein said analytical output is distinguishable for the various predetermined nucleic acid target sequences.

* * * * *

SEQUENCE LISTING

<160> NUMBER OF SEQ ID NOS: 99

<210> SEQ ID NO: 1
<211> LENGTH: 56
<212> TYPE: DNA
<213> ORGANISM: Cytomegalovirus

<400> SEQUENCE: 1
ctctttaagc acgccggcgc ggcctgccgc gcgttggaga acggcaagct cacgca        56

<210> SEQ ID NO: 2
<211> LENGTH: 56
<212> TYPE: DNA
<213> ORGANISM: Cytomegalovirus

<400> SEQUENCE: 2
cagcagtgcg tgagcttgcc gttctccaac gcgcggcagg ccgcgccggc gtgctt        56

<210> SEQ ID NO: 3
<211> LENGTH: 56
<212> TYPE: DNA
<213> ORGANISM: Cytomegalovirus

<400> SEQUENCE: 3
ctctttaagc acgccggcgc ggcctgccgc gcgtcggaga acggcaagct cacgca        56

<210> SEQ ID NO: 4
<211> LENGTH: 55
<212> TYPE: DNA
<213> ORGANISM: Cytomegalovirus

<400> SEQUENCE: 4
cagcagtgcg tgagcttgcc gttctccgcg cgcggcaggc cgcgccggcg tgctt         55

<210> SEQ ID NO: 5
<211> LENGTH: 56
<212> TYPE: DNA
<213> ORGANISM: Cytomegalovirus

<400> SEQUENCE: 5
ctctttaagc acgccggcgc ggcctgccgc gcgtttgaga acggcaagct cacgca        56

<210> SEQ ID NO: 6
<211> LENGTH: 56
<212> TYPE: DNA
<213> ORGANISM: Cytomegalovirus

<400> SEQUENCE: 6
cagcagtgcg tgagcttgcc gttctcaaac gcgcggcagg ccgcgccggc gtgctt        56

<210> SEQ ID NO: 7
<211> LENGTH: 21
<212> TYPE: DNA
<213> ORGANISM: Cytomegalovirus

<400> SEQUENCE: 7
ggcgcggcct gccgcgcgtt g                                              21

<210> SEQ ID NO: 8
<211> LENGTH: 21
<212> TYPE: DNA
<213> ORGANISM: Cytomegalovirus

<400> SEQUENCE: 8
ggcgcggcct gccgcgcgtc g                                      21

<210> SEQ ID NO: 9
<211> LENGTH: 21
<212> TYPE: DNA
<213> ORGANISM: Cytomegalovirus

<400> SEQUENCE: 9
gcgtgagctt gccgttctcc g                                      21

<210> SEQ ID NO: 10
<211> LENGTH: 65
<212> TYPE: DNA
<213> ORGANISM: Homo sapiens

<400> SEQUENCE: 10
ctaatctgta agagcagatc cctggacagg cgaggaatac agagggcagc agacatcgaa    60
gagct                                                               65

<210> SEQ ID NO: 11
<211> LENGTH: 69
<212> TYPE: DNA
<213> ORGANISM: Homo sapiens

<400> SEQUENCE: 11
agctcttcga tgtctgctgc cctctgtatt cctcgcctgt ccagggatct gctcttacag    60
attagagct                                                           69

<210> SEQ ID NO: 12
<211> LENGTH: 65
<212> TYPE: DNA
<213> ORGANISM: Homo sapiens

<400> SEQUENCE: 12
ctaatctgta agagcagatc cctggacagg caaggaatac agagggcagc agacatcgaa    60
gagct                                                               65

<210> SEQ ID NO: 13
<211> LENGTH: 69
<212> TYPE: DNA
<213> ORGANISM: Homo sapiens

<400> SEQUENCE: 13
agctcttcga tgtctgctgc cctctgtatt ccttgcctgt ccagggatct gctcttacag    60
attagagct                                                           69

<210> SEQ ID NO: 14
<211> LENGTH: 22
<212> TYPE: DNA
<213> ORGANISM: Homo sapiens

<400> SEQUENCE: 14
ctgctgccct ctgtattcct cg                                     22

<210> SEQ ID NO: 15
<211> LENGTH: 22
<212> TYPE: DNA
<213> ORGANISM: Homo sapiens

```
<400> SEQUENCE: 15
ctgctgccct ctgtattcct tg                                              22

<210> SEQ ID NO: 16
<211> LENGTH: 65
<212> TYPE: DNA
<213> ORGANISM: Cytomegalovirus

<400> SEQUENCE: 16
cgtgtatgcc actttgatat tacacccatg aacgtgctca tcgacgtcaa cccgcacaac     60
gagct                                                                 65

<210> SEQ ID NO: 17
<211> LENGTH: 65
<212> TYPE: DNA
<213> ORGANISM: Cytomegalovirus

<400> SEQUENCE: 17
cgttgtgcgg gttcacgtcg atgagcacgt tcatgggtgt aatatcaaag tggcatacac     60
gagct                                                                 65

<210> SEQ ID NO: 18
<211> LENGTH: 65
<212> TYPE: DNA
<213> ORGANISM: Cytomegalovirus

<400> SEQUENCE: 18
cgtgtatgcc actttgatat tacacccgtg aacgtgctca tcgacgtcaa cccgcacaac     60
gagct                                                                 65

<210> SEQ ID NO: 19
<211> LENGTH: 65
<212> TYPE: DNA
<213> ORGANISM: Cytomegalovirus

<400> SEQUENCE: 19
cgttgtgcgg gttcacgtcg atgagcacgt tcacgggtgt aatatcaaag tggcatacac     60
gagct                                                                 65

<210> SEQ ID NO: 20
<211> LENGTH: 21
<212> TYPE: DNA
<213> ORGANISM: Cytomegalovirus

<400> SEQUENCE: 20
cactttgata ttacacccgt g                                               21

<210> SEQ ID NO: 21
<211> LENGTH: 30
<212> TYPE: DNA
<213> ORGANISM: rabbit

<400> SEQUENCE: 21
agacttctcc tcactggaca gatgcaccat                                      30

<210> SEQ ID NO: 22
<211> LENGTH: 26
<212> TYPE: DNA
<213> ORGANISM: rabbit

<400> SEQUENCE: 22
```

-continued gggtccatgg gtagacaacc agcagc    26

<210> SEQ ID NO: 23
<211> LENGTH: 18
<212> TYPE: DNA
<213> ORGANISM: Homo sapiens

<400> SEQUENCE: 23
cggagcctcc acctcccg    18

<210> SEQ ID NO: 24
<211> LENGTH: 18
<212> TYPE: DNA
<213> ORGANISM: Homo sapiens

<400> SEQUENCE: 24
caccctccag cccccagc    18

<210> SEQ ID NO: 25
<211> LENGTH: 18
<212> TYPE: DNA
<213> ORGANISM: Homo sapiens

<400> SEQUENCE: 25
cggagcctcc acctcctg    18

<210> SEQ ID NO: 26
<211> LENGTH: 19
<212> TYPE: DNA
<213> ORGANISM: Homo sapiens

<400> SEQUENCE: 26
cctcacctgc agcatcaac    19

<210> SEQ ID NO: 27
<211> LENGTH: 18
<212> TYPE: DNA
<213> ORGANISM: Homo sapiens

<400> SEQUENCE: 27
caccctccag cccccaac    18

<210> SEQ ID NO: 28
<211> LENGTH: 19
<212> TYPE: DNA
<213> ORGANISM: Homo sapiens

<400> SEQUENCE: 28
cctcacctgc agcatcatc    19

<210> SEQ ID NO: 29
<211> LENGTH: 15
<212> TYPE: DNA
<213> ORGANISM: Homo sapiens

<400> SEQUENCE: 29
cctggaaggg cactt    15

<210> SEQ ID NO: 30
<211> LENGTH: 15
<212> TYPE: DNA
<213> ORGANISM: Homo sapiens -continued

```
<400> SEQUENCE: 30
cctggaaggg cacgt                                                          15

<210> SEQ ID NO: 31
<211> LENGTH: 18
<212> TYPE: DNA
<213> ORGANISM: Homo sapiens

<400> SEQUENCE: 31
gattcagcag cgactgta                                                       18

<210> SEQ ID NO: 32
<211> LENGTH: 18
<212> TYPE: DNA
<213> ORGANISM: Homo sapiens

<400> SEQUENCE: 32
gattcagcag cgactgca                                                       18

<210> SEQ ID NO: 33
<211> LENGTH: 18
<212> TYPE: DNA
<213> ORGANISM: Homo sapiens

<400> SEQUENCE: 33
cgaggtgctg cgcctgcg                                                       18

<210> SEQ ID NO: 34
<211> LENGTH: 18
<212> TYPE: DNA
<213> ORGANISM: Homo sapiens

<400> SEQUENCE: 34
cgaggtgctg cgcctgtg                                                       18

<210> SEQ ID NO: 35
<211> LENGTH: 20
<212> TYPE: DNA
<213> ORGANISM: Homo sapiens

<400> SEQUENCE: 35
gggatcacat cgtggagatg                                                     20

<210> SEQ ID NO: 36
<211> LENGTH: 20
<212> TYPE: DNA
<213> ORGANISM: Homo sapiens

<400> SEQUENCE: 36
gggatcacaa cgaggagaag                                                     20

<210> SEQ ID NO: 37
<211> LENGTH: 74
<212> TYPE: DNA
<213> ORGANISM: Cytomegalovirus

<400> SEQUENCE: 37
ccaacagacg ctccacgttc tttctgacgt attcgtgcag catggtctgc gagcattcgt         60
ggtagaagcg agct                                                           74

<210> SEQ ID NO: 38
<211> LENGTH: 21
```

-continued

```
<212> TYPE: DNA
<213> ORGANISM: Cytomegalovirus

<400> SEQUENCE: 38
ctaccacgaa tgctcgcaga c                                        21

<210> SEQ ID NO: 39
<211> LENGTH: 21
<212> TYPE: DNA
<213> ORGANISM: Cytomegalovirus

<400> SEQUENCE: 39
ctaccacgaa tgctcgcaga t                                        21

<210> SEQ ID NO: 40
<211> LENGTH: 22
<212> TYPE: DNA
<213> ORGANISM: Artificial Sequence
<220> FEATURE:
<223> OTHER INFORMATION: Description of Artificial Sequence: Probe to
      prothrombin per productm, with phosphorothioate
      linkages between the first five bases on the 5'
      end.

<400> SEQUENCE: 40
atagcactgg gagcattgag gc                                       22

<210> SEQ ID NO: 41
<211> LENGTH: 20
<212> TYPE: DNA
<213> ORGANISM: Homo sapiens

<400> SEQUENCE: 41
gcacagacgg ctgttctctt                                          20

<210> SEQ ID NO: 42
<211> LENGTH: 22
<212> TYPE: DNA
<213> ORGANISM: Homo sapiens

<400> SEQUENCE: 42
tgcccagtgc ttaacaagac ca                                       22

<210> SEQ ID NO: 43
<211> LENGTH: 20
<212> TYPE: DNA
<213> ORGANISM: Homo sapiens

<400> SEQUENCE: 43
tgttatcaca ctggtgctaa                                          20

<210> SEQ ID NO: 44
<211> LENGTH: 13
<212> TYPE: DNA
<213> ORGANISM: Homo sapiens

<400> SEQUENCE: 44
gtgattctca gca                                                 13

<210> SEQ ID NO: 45
<211> LENGTH: 13
<212> TYPE: DNA
<213> ORGANISM: Homo sapiens

<400> SEQUENCE: 45
```

-continued gtgattctca gcg                                                        13

<210> SEQ ID NO: 46
<211> LENGTH: 22
<212> TYPE: DNA
<213> ORGANISM: Homo sapiens

<400> SEQUENCE: 46
gacaaaatac ctgtattcct cg                                              22

<210> SEQ ID NO: 47
<211> LENGTH: 22
<212> TYPE: DNA
<213> ORGANISM: Homo sapiens

<400> SEQUENCE: 47
gacaaaatac ctgtattcct tg                                              22

<210> SEQ ID NO: 48
<211> LENGTH: 34
<212> TYPE: DNA
<213> ORGANISM: Artificial Sequence
<220> FEATURE:
<223> OTHER INFORMATION: Description of Artificial Sequence: Probe for
      cytochrome B

<400> SEQUENCE: 48
aaactgcagc ccctcagaat gatatttgtc ctca                                 34

<210> SEQ ID NO: 49
<211> LENGTH: 35
<212> TYPE: DNA
<213> ORGANISM: Artificial Sequence
<220> FEATURE:
<223> OTHER INFORMATION: Description of Artificial Sequence: Probe for
      cytochrome B

<400> SEQUENCE: 49
aaaaagcttc catccaacat ctcagcatga tgaaa                                35

<210> SEQ ID NO: 50
<211> LENGTH: 12
<212> TYPE: DNA
<213> ORGANISM: Homo sapiens

<400> SEQUENCE: 50
ccagacgcct ca                                                         12

<210> SEQ ID NO: 51
<211> LENGTH: 12
<212> TYPE: DNA
<213> ORGANISM: Homo sapiens

<400> SEQUENCE: 51
accttcacgc ca                                                         12

<210> SEQ ID NO: 52
<211> LENGTH: 11
<212> TYPE: DNA
<213> ORGANISM: Unknown
<220> FEATURE:
<223> OTHER INFORMATION: Description of Unknown Organism: Common probe
      to cytochrome B.

<400> SEQUENCE: 52
tgccgagacg t                                                    11

<210> SEQ ID NO: 53
<211> LENGTH: 12
<212> TYPE: DNA
<213> ORGANISM: Artificial Sequence
<220> FEATURE:
<223> OTHER INFORMATION: Description of Artificial Sequence: Chicken
      cytochrome B.

<400> SEQUENCE: 53
gcagacacat cc                                                   12

<210> SEQ ID NO: 54
<211> LENGTH: 12
<212> TYPE: DNA
<213> ORGANISM: Artificial Sequence
<220> FEATURE:
<223> OTHER INFORMATION: Description of Artificial Sequence: Chicken
      cytochrome B.

<400> SEQUENCE: 54
ggaatctcca cg                                                   12

<210> SEQ ID NO: 55
<211> LENGTH: 12
<212> TYPE: DNA
<213> ORGANISM: Artificial Sequence
<220> FEATURE:
<223> OTHER INFORMATION: Description of Artificial Sequence: Bovine
      cytochrome B.

<400> SEQUENCE: 55
acatacacgc aa                                                   12

<210> SEQ ID NO: 56
<211> LENGTH: 12
<212> TYPE: DNA
<213> ORGANISM: Artificial Sequence
<220> FEATURE:
<223> OTHER INFORMATION: Description of Artificial Sequence: Canine
      cytochrome B.

<400> SEQUENCE: 56
atatgcacgc aa                                                   12

<210> SEQ ID NO: 57
<211> LENGTH: 29
<212> TYPE: DNA
<213> ORGANISM: Artificial Sequence
<220> FEATURE:
<223> OTHER INFORMATION: Description of Artificial Sequence: Probe which
      forms hairpin when allowed to self-anneal.

<400> SEQUENCE: 57
atgaacgtac gtcggatgag cacgttcat                                 29

<210> SEQ ID NO: 58
<211> LENGTH: 29
<212> TYPE: DNA
<213> ORGANISM: Artificial Sequence
<220> FEATURE:
<223> OTHER INFORMATION: Description of Artificial Sequence: Probe which
      forms hairpin when allowed to self-anneal.

<400> SEQUENCE: 58

-continued gtgaacgtac gtcggatgag cacgttcat                                              29

<210> SEQ ID NO: 59
<211> LENGTH: 29
<212> TYPE: DNA
<213> ORGANISM: Artificial Sequence
<220> FEATURE:
<223> OTHER INFORMATION: Description of Artificial Sequence: Probe which
      forms hairpin when allowed to self-anneal.

<400> SEQUENCE: 59
ataaacgtac gtcggatgag cacgttcat                                              29

<210> SEQ ID NO: 60
<211> LENGTH: 24
<212> TYPE: DNA
<213> ORGANISM: Artificial Sequence
<220> FEATURE:
<223> OTHER INFORMATION: Description of Artificial Sequence: Probe which
      forms hairpin when allowed to self-anneal.

<400> SEQUENCE: 60
ataaacgtac gtcggatgag cacg                                                   24

<210> SEQ ID NO: 61
<211> LENGTH: 41
<212> TYPE: DNA
<213> ORGANISM: Artificial Sequence
<220> FEATURE:
<223> OTHER INFORMATION: Description of Artificial Sequence:
      Hypothetical example.

<400> SEQUENCE: 61
agctaaggtc acaaccggtt tgccgcttta ttataccggg g                                41

<210> SEQ ID NO: 62
<211> LENGTH: 62
<212> TYPE: DNA
<213> ORGANISM: Artificial Sequence
<220> FEATURE:
<223> OTHER INFORMATION: Description of Artificial Sequence:
      Hypothetical example.

<400> SEQUENCE: 62
cccggagaga cctccttaag gggccatatt atttcgtcga ttccagtgtt ggccaaacgg            60
at                                                                           62

<210> SEQ ID NO: 63
<211> LENGTH: 77
<212> TYPE: DNA
<213> ORGANISM: Artificial Sequence
<220> FEATURE:
<223> OTHER INFORMATION: Description of Artificial Sequence:
      Hypothetical example.

<400> SEQUENCE: 63
gggcctctct ggaggaattc cccggtataa taaagcagct aaggtcacaa ccggtttgcc            60
gctttattat accgggg                                                           77

<210> SEQ ID NO: 64
<211> LENGTH: 16
<212> TYPE: DNA
<213> ORGANISM: Artificial Sequence
<220> FEATURE:
<223> OTHER INFORMATION: Description of Artificial Sequence:
      Hypothetical example.

<400> SEQUENCE: 64
cccggagaga cctcct                                                          16

<210> SEQ ID NO: 65
<211> LENGTH: 77
<212> TYPE: DNA
<213> ORGANISM: Artificial Sequence
<220> FEATURE:
<223> OTHER INFORMATION: Description of Artificial Sequence:
      Hypothetical example.

<400> SEQUENCE: 65
cccggagaga cctccttaag gggccatatt atttcgtcga ttccagtgtt ggccaaacgg           60
cgaaataata tggcccc                                                         77

<210> SEQ ID NO: 66
<211> LENGTH: 20
<212> TYPE: DNA
<213> ORGANISM: Artificial Sequence
<220> FEATURE:
<223> OTHER INFORMATION: Description of Artificial Sequence: CAH reverse

<400> SEQUENCE: 66
ccagagcagg gagtagtctc                                                      20

<210> SEQ ID NO: 67
<211> LENGTH: 20
<212> TYPE: DNA
<213> ORGANISM: Artificial Sequence
<220> FEATURE:
<223> OTHER INFORMATION: Description of Artificial Sequence: CAH forward
      probe

<400> SEQUENCE: 67
gcatatagag catggctgtg                                                      20

<210> SEQ ID NO: 68
<211> LENGTH: 19
<212> TYPE: DNA
<213> ORGANISM: Artificial Sequence
<220> FEATURE:
<223> OTHER INFORMATION: Description of Artificial Sequence: CAH forward
      probe (CYP21 only)

<400> SEQUENCE: 68
cctgtccttg ggagactac                                                       19

<210> SEQ ID NO: 69
<211> LENGTH: 18
<212> TYPE: DNA
<213> ORGANISM: Artificial Sequence
<220> FEATURE:
<223> OTHER INFORMATION: Description of Artificial Sequence: CAH reverse
      probe

<400> SEQUENCE: 69
cccagttcgt ggtctagc                                                        18

<210> SEQ ID NO: 70
<211> LENGTH: 18
<212> TYPE: DNA
<213> ORGANISM: Artificial Sequence
<220> FEATURE:
<223> OTHER INFORMATION: Description of Artificial Sequence: CAH reverse
      probe

```
<400> SEQUENCE: 70
tcctcactca tccccaac                                                        18

<210> SEQ ID NO: 71
<211> LENGTH: 21
<212> TYPE: DNA
<213> ORGANISM: Artificial Sequence
<220> FEATURE:
<223> OTHER INFORMATION: Description of Artificial Sequence: CAH forward
      probe

<400> SEQUENCE: 71
gaaatacgga cgtcccaagg c                                                    21

<210> SEQ ID NO: 72
<211> LENGTH: 20
<212> TYPE: DNA
<213> ORGANISM: Artificial Sequence
<220> FEATURE:
<223> OTHER INFORMATION: Description of Artificial Sequence: CAH reverse
      probe (CYP21 only)

<400> SEQUENCE: 72
ctttccagag cagggagtag                                                      20

<210> SEQ ID NO: 73
<211> LENGTH: 20
<212> TYPE: DNA
<213> ORGANISM: Artificial Sequence
<220> FEATURE:
<223> OTHER INFORMATION: Description of Artificial Sequence: CAH forward
      probe (CYP21 only)

<400> SEQUENCE: 73
ccggacctgt ccttgggaga                                                      20

<210> SEQ ID NO: 74
<211> LENGTH: 40
<212> TYPE: DNA
<213> ORGANISM: Homo sapiens

<400> SEQUENCE: 74
agaagcccgg ggcaagaggc aggaggtgga ggctccggag                                40

<210> SEQ ID NO: 75
<211> LENGTH: 40
<212> TYPE: DNA
<213> ORGANISM: Homo sapiens

<400> SEQUENCE: 75
agcttgtctg caggaggagc tgggggctgg agggtgggaa                                40

<210> SEQ ID NO: 76
<211> LENGTH: 40
<212> TYPE: DNA
<213> ORGANISM: Homo sapiens

<400> SEQUENCE: 76
tccgaaggtg aggtaacagt tgatgctgca ggtgaggaga                                40

<210> SEQ ID NO: 77
<211> LENGTH: 40
<212> TYPE: DNA
<213> ORGANISM: Homo sapiens
```

<400> SEQUENCE: 77
tccactgcag ccatgtgcaa gtgcccttcc aggagctgtc         40

<210> SEQ ID NO: 78
<211> LENGTH: 40
<212> TYPE: DNA
<213> ORGANISM: Homo sapiens

<400> SEQUENCE: 78
tcgtggtcta gctcctccta cagtcgctgc tgaatctggg         40

<210> SEQ ID NO: 79
<211> LENGTH: 40
<212> TYPE: DNA
<213> ORGANISM: Homo sapiens

<400> SEQUENCE: 79
gctaagggca caacgggcca caggcgcagc acctcggcga         40

<210> SEQ ID NO: 80
<211> LENGTH: 40
<212> TYPE: DNA
<213> ORGANISM: Homo sapiens

<400> SEQUENCE: 80
cagcttgtct gcaggaggag ttgggggctg gagggtggga         40

<210> SEQ ID NO: 81
<211> LENGTH: 40
<212> TYPE: DNA
<213> ORGANISM: Homo sapiens

<400> SEQUENCE: 81
ggctaagggc acaacgggcc gcaggcgcag cacctcggcg         40

<210> SEQ ID NO: 82
<211> LENGTH: 89
<212> TYPE: DNA
<213> ORGANISM: Artificial Sequence
<220> FEATURE:
<223> OTHER INFORMATION: Description of Artificial Sequence: probe to
      wild-type targets 10870 and 10994

<400> SEQUENCE: 82
gaactatatt gtctttctct gattctgact cgtcatgtct cagctttagt ttaatacgac     60
tcactatagg gctcagtgtg attccacct                                       89

<210> SEQ ID NO: 83
<211> LENGTH: 53
<212> TYPE: DNA
<213> ORGANISM: Artificial Sequence
<220> FEATURE:
<223> OTHER INFORMATION: Description of Artificial Sequence: wild-type
      target

<400> SEQUENCE: 83
ttgcagagaa agacaatata gttcttggag aaggtggaat cacactgagt gga            53

<210> SEQ ID NO: 84
<211> LENGTH: 53
<212> TYPE: DNA
<213> ORGANISM: Artificial Sequence
<220> FEATURE:

```
<223> OTHER INFORMATION: Description of Artificial Sequence: mutant
      target

<400> SEQUENCE: 84
ttgcagagaa agacaatata gttctttgag aaggtggaat cacactgagt gga          53

<210> SEQ ID NO: 85
<211> LENGTH: 22
<212> TYPE: DNA
<213> ORGANISM: Artificial Sequence
<220> FEATURE:
<223> OTHER INFORMATION: Description of Artificial Sequence: probe which
      hybridizes only to wild-type target

<400> SEQUENCE: 85
ctcagtgtga ttccacttca cc                                            22

<210> SEQ ID NO: 86
<211> LENGTH: 23
<212> TYPE: DNA
<213> ORGANISM: Artificial Sequence
<220> FEATURE:
<223> OTHER INFORMATION: Description of Artificial Sequence: probe which
      hybridizes only to mutant target

<400> SEQUENCE: 86
ctcagtgtga ttccaccttc aca                                           23

<210> SEQ ID NO: 87
<211> LENGTH: 13
<212> TYPE: DNA
<213> ORGANISM: Homo sapiens

<400> SEQUENCE: 87
gtgactctca gcg                                                      13

<210> SEQ ID NO: 88
<211> LENGTH: 13
<212> TYPE: DNA
<213> ORGANISM: Artificial Sequence
<220> FEATURE:
<223> OTHER INFORMATION: Description of Artificial Sequence:  match to
      mutant prothrombin; complementary to wild-type 9
      from 3'

<400> SEQUENCE: 88
gtgactctca gca                                                      13

<210> SEQ ID NO: 89
<211> LENGTH: 13
<212> TYPE: DNA
<213> ORGANISM: Artificial Sequence
<220> FEATURE:
<223> OTHER INFORMATION: Description of Artificial Sequence:  match to
      wild-type prothrombin; mismatch 9 from 3'

<400> SEQUENCE: 89
gtgattctca gcg                                                      13

<210> SEQ ID NO: 90
<211> LENGTH: 13
<212> TYPE: DNA
<213> ORGANISM: Artificial Sequence
<220> FEATURE:
<223> OTHER INFORMATION: Description of Artificial Sequence: match to
      mutant prothrombin; mismatch 9 from 3'
```

```
<400> SEQUENCE: 90
gtgattctca gca                                                          13

<210> SEQ ID NO: 91
<211> LENGTH: 22
<212> TYPE: DNA
<213> ORGANISM: Homo sapiens

<400> SEQUENCE: 91
gacaaaatac ctgtattcct cg                                                22

<210> SEQ ID NO: 92
<211> LENGTH: 22
<212> TYPE: DNA
<213> ORGANISM: Homo sapiens

<400> SEQUENCE: 92
gacaaaatac ctgtattcct tg                                                22

<210> SEQ ID NO: 93
<211> LENGTH: 16
<212> TYPE: DNA
<213> ORGANISM: Homo sapiens

<400> SEQUENCE: 93
ggagcattga ggctcg                                                       16

<210> SEQ ID NO: 94
<211> LENGTH: 16
<212> TYPE: DNA
<213> ORGANISM: Homo sapiens

<400> SEQUENCE: 94
ggagcattga ggcttg                                                       16

<210> SEQ ID NO: 95
<211> LENGTH: 19
<212> TYPE: DNA
<213> ORGANISM: Homo sapiens

<400> SEQUENCE: 95
catcatagga aacaccaag                                                    19

<210> SEQ ID NO: 96
<211> LENGTH: 19
<212> TYPE: DNA
<213> ORGANISM: Homo sapiens

<400> SEQUENCE: 96
catcatagga aacaccaat                                                    19

<210> SEQ ID NO: 97
<211> LENGTH: 22
<212> TYPE: DNA
<213> ORGANISM: Homo sapiens

<400> SEQUENCE: 97
tggatttaag cagagttcaa gt                                                22

<210> SEQ ID NO: 98
<211> LENGTH: 22
<212> TYPE: DNA
<213> ORGANISM: Homo sapiens
```

-continued

```
<400> SEQUENCE: 98
tggatttaag cagagttcaa aa                                        22

<210> SEQ ID NO: 99
<211> LENGTH: 23
<212> TYPE: DNA
<213> ORGANISM: Artificial Sequence
<220> FEATURE:
<223> OTHER INFORMATION: Description of Artificial Sequence: probe which
      hybridizes to 10870 and 10994

<400> SEQUENCE: 99
ctaaagctga gacatgacga gtc                                       23
```